(12) United States Patent
Classon et al.

(10) Patent No.: US 9,228,014 B2
(45) Date of Patent: Jan. 5, 2016

(54) ANTIBODIES CAPABLE OF BLOCKING THE INTERACTION BETWEEN CD48 AND A CD48 RECEPTOR

(75) Inventors: Brendan J. Classon, Ridgefield, CT (US); Ana Kostic, New York, NY (US); Xunbao Duan, Horsham, PA (US)

(73) Assignee: Regeneron Pharmaceuticals, Inc., Tarrytown, NY (US)

( * ) Notice: Subject to any disclaimer, the term of this patent is extended or adjusted under 35 U.S.C. 154(b) by 69 days.

(21) Appl. No.: 13/244,960

(22) Filed: Sep. 26, 2011

(65) Prior Publication Data

US 2012/0076790 A1 Mar. 29, 2012

Related U.S. Application Data

(60) Provisional application No. 61/386,746, filed on Sep. 27, 2010, provisional application No. 61/475,280, filed on Apr. 14, 2011, provisional application No. 61/515,490, filed on Aug. 5, 2011.

(51) Int. Cl.
*A61K 39/395* (2006.01)
*C07K 16/28* (2006.01)
*A61K 39/00* (2006.01)

(52) U.S. Cl.
CPC ....... *C07K 16/2803* (2013.01); *A61K 2039/505* (2013.01); *C07K 2317/21* (2013.01); *C07K 2317/33* (2013.01); *C07K 2317/34* (2013.01); *C07K 2317/35* (2013.01); *C07K 2317/76* (2013.01); *C07K 2317/92* (2013.01)

(58) Field of Classification Search
None
See application file for complete search history.

(56) References Cited

U.S. PATENT DOCUMENTS

| 4,692,405 | A | 9/1987 | Freedman et al. |
|---|---|---|---|
| 5,576,423 | A | 11/1996 | Aversa et al. |
| 2007/0178072 | A1 | 8/2007 | Watanabe |
| 2007/0212353 | A1 | 9/2007 | Levi-Schaffer et al. |

FOREIGN PATENT DOCUMENTS

| EP | 2418222 A1 | 2/2012 |
|---|---|---|
| JP | 2009-539349 A | 11/2009 |
| WO | 97/35614 A1 | 10/1997 |
| WO | 2007/143168 A2 | 12/2007 |

OTHER PUBLICATIONS

Evans et al., J. Biological Chemistry 281: 29309-29320, 2006.*
Clarkson et al., J. Biol. Chem 284: 24725-24734, 2009.*
Detre et al , "SLAM family receptors and the SLAM-associated protein (SAP) modulate T cell functions," Semin. Immunopathol.; Jun. 2010, 32(2):157-171.
Evans et al., "Crystal Structure and Binding Properties of the CD2 and CD244 (2B4)-binding Protein, CD48," J. Biol. Chem., Sep. 29, 2006, 281(39):29309-29320.
Mami-Chouaib et al., "T Cell Target 1 (TCT.1): a Novel Target Molecule for Human Non-Major Histocompatibility Complex-restricted T Lymphocytes," J. Exp. Med., Oct. 1990, 172:1071-1082.
Munitz et al., "2B4 (CD244) is Expressed and Functional on Human Eosinaphils," J. Immunol., 2005, 174:110-118.
Munitz et al., "CD48 Is an Allergen and IL-3-Induced Activation Molecule on Eosinophils," J. Immunol., 2006, 177:77-83.
Munitz et al., "CD48 is Critically Involved in Allergic Eosinophilic Airway Inflammation," Am. J. Respir. Crit. Care Med., 2007, 175:911-918.
Thorley-Lawson et al., "Epstein-Barr Virus Superinduces a New Human B Cell Differentiation Antigen (B-LAST 1) Expressed on Transformed Lymphoblasts," Cell, Sep. 1982, 30:415-425.
Velikovsky et al., "Structure of Natural Killer Receptor 2B4 Bound to CD48 Reveals Basis for Heterophilic Recognition in Signaling Lymphocyte Activation Molecule Family," Immunity, Oct. 2007, 27:572-584.
Abadia-Molina et al., "CD48 Controls T-Cell and Antigen-Presenting Cell Functions in Experimental Colitis," Gastroenterology, Feb. 2006, 130:424-434.
Kato et al., "CD48 Is a Counter-Receptor for Mouse CD2 and Is Involved in T Cell Activation," J. Exp. Med., Nov. 1992, 176:1241-1249.
Qin et al., "Anti-CD2 Receptor and Anti-CD2 Ligand (CD48) Antibodies Synergize to Prolong Allograft Survival," J. Exp. Med., Jan. 1994, 179:341-346.
Andrade et al., "Engraftment of Peripheral Blood Mononuclear Cells From Systemic Lupus Erythematosus and Antiphospholipid Syndrome Patient Donors Into BALB-RAG-2-/-IL-2Rγ-/- Mice"; Arthritis & Rheumatism; 63(9):2764-2773 (2011).
Balada et al., "Enhanced transcript levels of CD48 in CD4+ T cells from Systemic Lupus Erythematosus patients"; Immunobiology; 216(9):1034-1037 (2010), doi: 10.1016/j.imbio.2011.03.004.
Balada et al., Abstract only, "Enhanced transcript levels of CD48 in CD4+ T cells from Systemic Lupus Erythematosus patients"; Immunobiology; 216(9):1034-1037 (Sep. 2011) (e pub Mar. 12, 2011).
Chan et al., "The role of SAP and the SLAM family in autoimmunity"; Current Opinion in Immunology; 18:656-664 (2006).
Crispín et al., "T cells as therapeutic targets in SLE"; Nat. Rev. Rheumatol; 6:317-325 (2010).
International Search Report from corresponding to PCT/US2011/053193, mailed Jan. 18, 2012.
Januchowski et al., "Prevalence of ZAP-70, LAT, SLP-76, and DNA methyltransferase 1 expression in CD4+ T cells of patients with systemic lupus erythematosus"; Clin. Rheumatol; 27:21-27 (2008).

(Continued)

*Primary Examiner* — Phillip Gambel
(74) *Attorney, Agent, or Firm* — Merchant & Gould, P.C.

(57) ABSTRACT

The present invention provides antibodies that bind to CD48 and methods of using same. According to certain embodiments of the invention, the antibodies are fully human antibodies that bind to human CD48. In certain embodiments, the antibodies of the present invention block the binding of CD48 to one or more CD48 receptor. The antibodies of the invention are useful, inter alia, for the treatment of diseases and disorders associated with one or more CD48 biological activities, including the treatment of allergic conditions and other inflammatory conditions.

21 Claims, 2 Drawing Sheets

(56) References Cited

OTHER PUBLICATIONS

Keszei et al., "Auto-antibody production and glomerulonephritis in congenic Slamf1-/- and Slamf2-/- [B6.129] but not in Slamf1-/- and Slamf2-/- [BALB/c.129] mice"; International Immunology; 23(2):149-158 (2011).

Kim et al., "Altered expression of signalling lymphocyte activation molecule (SLAM) family receptors CS1 (CD319) and 2B4 (CD244) in patients with systemic lupus erythematosus"; Clinical and Experimental Immunology; 160(3):348-358 (Jun. 2010).

Kim et al., "IL-7Rα low memory CD8+ T cells are significantly elevated in patients with systemic lupus erythematosus"; Rheumatology; 51:1587-1594 (2012).

Koh et al., "The SLAM family member CD48 (Slamf2) protects lupus-prone mice from autoimmune nephritis"; Journal of Autoimmunity; 37:48-57 (2011).

Lyons et al., "Novel expression signatures identified by transcriptional analysis of separated leucocyte subsets in systemic lupus erythematosus and vasculitis"; Ann. Rheum. Dis.; 69:1208-1213 (2010).

Ota et al., "Single nucleotide polymorphisms of CD244 gene predispose to renal and neuropsychiatric manifestations with systemic lupus erythematosus," Modern Rheumatology; 20(5):427-431 (Oct. 2010).

Brown et al., "2B4, the Natural Killer and T Cell Immunoglobulin Superfamily Surface Protein, Is a Ligand for CD48"; J Exp. Med.; 188(11):2083-2090 (Dec. 7, 1998).

Japanese Office Action mailed Sep. 7, 2015, for corresponding Japanese Patent Application No. 2013-530383.

Japanese Office Action mailed Sep. 7, 2015, for corresponding Japanese Patent Application No. 2013-530383 (English Translation).

Wei et al., "Expression and characterisation of recombinant human CD48 and isolation of a human anti-CD48 monoclonal antibody by phage display"; J of Chem Technol and Biotechnol; 80(7):782-795 (2005).

\* cited by examiner

SEQUENCE LISTING

```
<160> NUMBER OF SEQ ID NOS: 392

<210> SEQ ID NO 1
<211> LENGTH: 354
<212> TYPE: DNA
<213> ORGANISM: Artificial Sequence
```

<220> FEATURE:
<223> OTHER INFORMATION: Synthetic

<400> SEQUENCE: 1

```
gaggggcagc tgttggaatc tggggggaggc ttggcacagc cggggggggtc cctgagactc    60
tcctgtgcag cctctggaat cacctttggc agatatgcca tgagctgggt ccgccaggct   120
ccagggaagg ggctggagtg ggtctcactt ataagtggca gtggtggtag cacataccac   180
gcagactccg tgaagggccg gttcaccatc tccagagaca attccaagaa cacactatat   240
ctgcaaatga acagcctgag agccgaggac acggccgtat attactgtgc gatctacaat   300
aactacaact ggttcgaccc ctggggccag ggaaccctgg tcaccgtctc ctca          354
```

<210> SEQ ID NO 2
<211> LENGTH: 118
<212> TYPE: PRT
<213> ORGANISM: Artificial Sequence
<220> FEATURE:
<223> OTHER INFORMATION: Synthetic

<400> SEQUENCE: 2

```
Glu Gly Gln Leu Leu Glu Ser Gly Gly Gly Leu Ala Gln Pro Gly Gly
  1               5                  10                  15

Ser Leu Arg Leu Ser Cys Ala Ala Ser Gly Ile Thr Phe Gly Arg Tyr
             20                  25                  30

Ala Met Ser Trp Val Arg Gln Ala Pro Gly Lys Gly Leu Glu Trp Val
         35                  40                  45

Ser Leu Ile Ser Gly Ser Gly Gly Ser Thr Tyr His Ala Asp Ser Val
     50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Ile Tyr Asn Asn Tyr Asn Trp Phe Asp Pro Trp Gly Gln Gly Thr
            100                 105                 110

Leu Val Thr Val Ser Ser
        115
```

<210> SEQ ID NO 3
<211> LENGTH: 24
<212> TYPE: DNA
<213> ORGANISM: Artificial Sequence
<220> FEATURE:
<223> OTHER INFORMATION: Synthetic

<400> SEQUENCE: 3

```
ggaatcacct ttggcagata tgcc                                            24
```

<210> SEQ ID NO 4
<211> LENGTH: 8
<212> TYPE: PRT
<213> ORGANISM: Artificial Sequence
<220> FEATURE:
<223> OTHER INFORMATION: Synthetic

<400> SEQUENCE: 4

```
Gly Ile Thr Phe Gly Arg Tyr Ala
  1               5
```

<210> SEQ ID NO 5
<211> LENGTH: 24

<212> TYPE: DNA
<213> ORGANISM: Artificial Sequence
<220> FEATURE:
<223> OTHER INFORMATION: Synthetic

<400> SEQUENCE: 5
ataagtggca gtggtggtag caca                                          24

<210> SEQ ID NO 6
<211> LENGTH: 8
<212> TYPE: PRT
<213> ORGANISM: Artificial Sequence
<220> FEATURE:
<223> OTHER INFORMATION: Synthetic

<400> SEQUENCE: 6

Ile Ser Gly Ser Gly Gly Ser Thr
 1               5

<210> SEQ ID NO 7
<211> LENGTH: 33
<212> TYPE: DNA
<213> ORGANISM: Artificial Sequence
<220> FEATURE:
<223> OTHER INFORMATION: Synthetic

<400> SEQUENCE: 7
gcgatctaca ataactacaa ctggttcgac ccc                                33

<210> SEQ ID NO 8
<211> LENGTH: 11
<212> TYPE: PRT
<213> ORGANISM: Artificial Sequence
<220> FEATURE:
<223> OTHER INFORMATION: Synthetic

<400> SEQUENCE: 8

Ala Ile Tyr Asn Asn Tyr Asn Trp Phe Asp Pro
 1               5                  10

<210> SEQ ID NO 9
<211> LENGTH: 324
<212> TYPE: DNA
<213> ORGANISM: Artificial Sequence
<220> FEATURE:
<223> OTHER INFORMATION: Synthetic

<400> SEQUENCE: 9
gaaattgtgt tgacgcagtc tccaggcacc ttgtctttgt ctccagggga aagagccacc    60
ctctcctgca gggccagtca gagtgttagc agcaactact tagcctggta ccagcagaaa   120
cctggccagg ctcccaggct cctcatctat gatgcatcca gcagggccac tgacatccca   180
gacaggttca gtggcagtgg gtctgggaca gacttcactc tcaccatcag cagactggag   240
cctgaagatt ttgcagtgta ttactgtcag cagtatggta gctcacctcg gacgttcggc   300
caagggacca aggtggaaat caaa                                         324

<210> SEQ ID NO 10
<211> LENGTH: 108
<212> TYPE: PRT
<213> ORGANISM: Artificial Sequence
<220> FEATURE:
<223> OTHER INFORMATION: Synthetic

<400> SEQUENCE: 10

```
Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Asn
            20                  25                  30

Tyr Leu Ala Trp Tyr Gln Gln Lys Pro Gly Gln Ala Pro Arg Leu Leu
        35                  40                  45

Ile Tyr Asp Ala Ser Ser Arg Ala Thr Asp Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Ser Pro
                85                  90                  95

Arg Thr Phe Gly Gln Gly Thr Lys Val Glu Ile Lys
                100                 105
```

<210> SEQ ID NO 11
<211> LENGTH: 21
<212> TYPE: DNA
<213> ORGANISM: Artificial Sequence
<220> FEATURE:
<223> OTHER INFORMATION: Synthetic

<400> SEQUENCE: 11
cagagtgtta gcagcaacta c                                           21

<210> SEQ ID NO 12
<211> LENGTH: 7
<212> TYPE: PRT
<213> ORGANISM: Artificial Sequence
<220> FEATURE:
<223> OTHER INFORMATION: Synthetic

<400> SEQUENCE: 12

```
Gln Ser Val Ser Ser Asn Tyr
1               5
```

<210> SEQ ID NO 13
<211> LENGTH: 9
<212> TYPE: DNA
<213> ORGANISM: Artificial Sequence
<220> FEATURE:
<223> OTHER INFORMATION: Synthetic

<400> SEQUENCE: 13 gatgcatcc                                                          9

<210> SEQ ID NO 14
<211> LENGTH: 3
<212> TYPE: PRT
<213> ORGANISM: Artificial Sequence
<220> FEATURE:
<223> OTHER INFORMATION: Synthetic

<400> SEQUENCE: 14

```
Asp Ala Ser
1
```

<210> SEQ ID NO 15
<211> LENGTH: 27
<212> TYPE: DNA
<213> ORGANISM: Artificial Sequence
<220> FEATURE:
<223> OTHER INFORMATION: Synthetic

<400> SEQUENCE: 15
cagcagtatg gtagctcacc tcggacg                                              27

<210> SEQ ID NO 16
<211> LENGTH: 9
<212> TYPE: PRT
<213> ORGANISM: Artificial Sequence
<220> FEATURE:
<223> OTHER INFORMATION: Synthetic

<400> SEQUENCE: 16

Gln Gln Tyr Gly Ser Ser Pro Arg Thr
 1               5

<210> SEQ ID NO 17
<211> LENGTH: 348
<212> TYPE: DNA
<213> ORGANISM: Artificial Sequence
<220> FEATURE:
<223> OTHER INFORMATION: Synthetic

<400> SEQUENCE: 17
caggtccagc tggtacagtc aggggctgag gtgaagaagc ctggggcctc agtgaaggtc          60
tcctgcaagg tttccggata caccctcact gaattatcca tacactgggt gcgacaggct        120
cctggaaaag ggcttgagtg gatgggaggt tttgatcctg aagatggtga aacaatctac        180
gcacagaagt tccagggcag agtcaacatg accgaggaca catctacaga cacagcctac        240
atggagctga gcagcctgag atctgatgac acgaccgtgt atttctgtgc atcacttctt        300
ccctactttg actactgggg ccagggaacc ctggtcaccg tctcctca                     348

<210> SEQ ID NO 18
<211> LENGTH: 116
<212> TYPE: PRT
<213> ORGANISM: Artificial Sequence
<220> FEATURE:
<223> OTHER INFORMATION: Synthetic

<400> SEQUENCE: 18

Gln Val Gln Leu Val Gln Ser Gly Ala Glu Val Lys Lys Pro Gly Ala
 1               5                  10                  15

Ser Val Lys Val Ser Cys Lys Val Ser Gly Tyr Thr Leu Thr Glu Leu
                20                  25                  30

Ser Ile His Trp Val Arg Gln Ala Pro Gly Lys Gly Leu Glu Trp Met
            35                  40                  45

Gly Gly Phe Asp Pro Glu Asp Gly Glu Thr Ile Tyr Ala Gln Lys Phe
        50                  55                  60

Gln Gly Arg Val Asn Met Thr Glu Asp Thr Ser Thr Asp Thr Ala Tyr
 65                 70                  75                  80

Met Glu Leu Ser Ser Leu Arg Ser Asp Asp Thr Thr Val Tyr Phe Cys
                85                  90                  95

Ala Ser Leu Leu Pro Tyr Phe Asp Tyr Trp Gly Gln Gly Thr Leu Val
                100                 105                 110

Thr Val Ser Ser
        115

<210> SEQ ID NO 19
<211> LENGTH: 24
<212> TYPE: DNA
<213> ORGANISM: Artificial Sequence
<220> FEATURE:

<223> OTHER INFORMATION: Synthetic

<400> SEQUENCE: 19
ggatacaccc tcactgaatt atcc                                           24

<210> SEQ ID NO 20
<211> LENGTH: 8
<212> TYPE: PRT
<213> ORGANISM: Artificial Sequence
<220> FEATURE:
<223> OTHER INFORMATION: Synthetic

<400> SEQUENCE: 20

Gly Tyr Thr Leu Thr Glu Leu Ser
 1               5

<210> SEQ ID NO 21
<211> LENGTH: 24
<212> TYPE: DNA
<213> ORGANISM: Artificial Sequence
<220> FEATURE:
<223> OTHER INFORMATION: Synthetic

<400> SEQUENCE: 21
tttgatcctg aagatggtga aaca                                           24

<210> SEQ ID NO 22
<211> LENGTH: 8
<212> TYPE: PRT
<213> ORGANISM: Artificial Sequence
<220> FEATURE:
<223> OTHER INFORMATION: Synthetic

<400> SEQUENCE: 22

Phe Asp Pro Glu Asp Gly Glu Thr
 1               5

<210> SEQ ID NO 23
<211> LENGTH: 27
<212> TYPE: DNA
<213> ORGANISM: Artificial Sequence
<220> FEATURE:
<223> OTHER INFORMATION: Synthetic

<400> SEQUENCE: 23
gcatcacttc ttccctactt tgactac                                        27

<210> SEQ ID NO 24
<211> LENGTH: 9
<212> TYPE: PRT
<213> ORGANISM: Artificial Sequence
<220> FEATURE:
<223> OTHER INFORMATION: Synthetic

<400> SEQUENCE: 24

Ala Ser Leu Leu Pro Tyr Phe Asp Tyr
 1               5

<210> SEQ ID NO 25
<211> LENGTH: 324
<212> TYPE: DNA
<213> ORGANISM: Artificial Sequence
<220> FEATURE:
<223> OTHER INFORMATION: Synthetic

<400> SEQUENCE: 25

| | |
|---|---|
| gaaattgtgt tgacgcagtc tccaggcacc ctgtctttgt ctccagggga aagagccacc | 60 |
| ctctcctgca gggccagtca gagtgttagc agcagttact tagcctggta ccagcagaaa | 120 |
| cctggccagg ctcccaggct cctcatctat ggtgcatcca gcagggccac tggcatccca | 180 |
| gacaggttca gtggcagtgg gtctgggaca gatttcactc tctccatcag tagactggag | 240 |
| cccgaagatt ttgcagtgta ttttgtcag cagtatggca gctcaatgta cacttttggc | 300 |
| cagggaccaa agctggagat caaa | 324 |

<210> SEQ ID NO 26
<211> LENGTH: 108
<212> TYPE: PRT
<213> ORGANISM: Artificial Sequence
<220> FEATURE:
<223> OTHER INFORMATION: Synthetic

<400> SEQUENCE: 26

```
Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Ser Ile Ser Arg Leu Glu
65                  70                  75                  80

Pro Glu Asp Phe Ala Val Tyr Phe Cys Gln Gln Tyr Gly Ser Ser Met
                85                  90                  95

Tyr Thr Phe Gly Gln Gly Thr Lys Leu Glu Ile Lys
            100                 105
```

<210> SEQ ID NO 27
<211> LENGTH: 21
<212> TYPE: DNA
<213> ORGANISM: Artificial Sequence
<220> FEATURE:
<223> OTHER INFORMATION: Synthetic

<400> SEQUENCE: 27

| | |
|---|---|
| cagagtgtta gcagcagtta c | 21 |

<210> SEQ ID NO 28
<211> LENGTH: 7
<212> TYPE: PRT
<213> ORGANISM: Artificial Sequence
<220> FEATURE:
<223> OTHER INFORMATION: Synthetic

<400> SEQUENCE: 28

```
Gln Ser Val Ser Ser Ser Tyr
1               5
```

<210> SEQ ID NO 29
<211> LENGTH: 9
<212> TYPE: DNA
<213> ORGANISM: Artificial Sequence
<220> FEATURE:
<223> OTHER INFORMATION: Synthetic

<400> SEQUENCE: 29

| | |
|---|---|
| ggtgcatcc | 9 |

<210> SEQ ID NO 30
<211> LENGTH: 3
<212> TYPE: PRT
<213> ORGANISM: Artificial Sequence
<220> FEATURE:
<223> OTHER INFORMATION: Synthetic

<400> SEQUENCE: 30

Gly Ala Ser
 1

<210> SEQ ID NO 31
<211> LENGTH: 27
<212> TYPE: DNA
<213> ORGANISM: Artificial Sequence
<220> FEATURE:
<223> OTHER INFORMATION: Synthetic

<400> SEQUENCE: 31
cagcagtatg gcagctcaat gtacact                                         27

<210> SEQ ID NO 32
<211> LENGTH: 9
<212> TYPE: PRT
<213> ORGANISM: Artificial Sequence
<220> FEATURE:
<223> OTHER INFORMATION: Synthetic

<400> SEQUENCE: 32

Gln Gln Tyr Gly Ser Ser Met Tyr Thr
 1               5

<210> SEQ ID NO 33
<211> LENGTH: 360
<212> TYPE: DNA
<213> ORGANISM: Artificial Sequence
<220> FEATURE:
<223> OTHER INFORMATION: Synthetic

<400> SEQUENCE: 33
caggtgcagc tggtgcagtc tggggctgac atgaagaagc ctggggcctc agtgagggtc      60
tcctgcaagg cttctggata caccttcacc gactacttta ttcactgggt gcgacaggcc     120
cctggacaag acctgaatg gatgggatgg atcaaccctg acagtggtgc cacaaactat      180
gcacagcagt tcagggcag ggtcaccatg accagggaca cgtccatcag cgcaacctac      240
atggagatga gcaggctgag atctgacgac acggccgtgt tttattgtgc gagagataag     300
gatggcagtg gctggtacct tgacgactgg ggccagggaa ccctggtcac cgtctcctca     360

<210> SEQ ID NO 34
<211> LENGTH: 120
<212> TYPE: PRT
<213> ORGANISM: Artificial Sequence
<220> FEATURE:
<223> OTHER INFORMATION: Synthetic

<400> SEQUENCE: 34

Gln Val Gln Leu Val Gln Ser Gly Ala Asp Met Lys Lys Pro Gly Ala
 1               5                  10                  15

Ser Val Arg Val Ser Cys Lys Ala Ser Gly Tyr Thr Phe Thr Asp Tyr
             20                  25                  30

Phe Ile His Trp Val Arg Gln Ala Pro Gly Gln Gly Pro Glu Trp Met
         35                  40                  45

```
Gly Trp Ile Asn Pro Asp Ser Gly Ala Thr Asn Tyr Ala Gln Gln Phe
        50                  55                  60

Gln Gly Arg Val Thr Met Thr Arg Asp Thr Ser Ile Ser Ala Thr Tyr
65                  70                  75                  80

Met Glu Met Ser Arg Leu Arg Ser Asp Asp Thr Ala Val Phe Tyr Cys
                85                  90                  95

Ala Arg Asp Lys Asp Gly Ser Gly Trp Tyr Leu Asp Asp Trp Gly Gln
                100                 105                 110

Gly Thr Leu Val Thr Val Ser Ser
            115                 120
```

<210> SEQ ID NO 35
<211> LENGTH: 24
<212> TYPE: DNA
<213> ORGANISM: Artificial Sequence
<220> FEATURE:
<223> OTHER INFORMATION: Synthetic

<400> SEQUENCE: 35
ggatacacct tcaccgacta cttt                                      24

<210> SEQ ID NO 36
<211> LENGTH: 8
<212> TYPE: PRT
<213> ORGANISM: Artificial Sequence
<220> FEATURE:
<223> OTHER INFORMATION: Synthetic

<400> SEQUENCE: 36

```
Gly Tyr Thr Phe Thr Asp Tyr Phe
1               5
```

<210> SEQ ID NO 37
<211> LENGTH: 24
<212> TYPE: DNA
<213> ORGANISM: Artificial Sequence
<220> FEATURE:
<223> OTHER INFORMATION: Synthetic

<400> SEQUENCE: 37
atcaaccctg acagtggtgc caca                                      24

<210> SEQ ID NO 38
<211> LENGTH: 8
<212> TYPE: PRT
<213> ORGANISM: Artificial Sequence
<220> FEATURE:
<223> OTHER INFORMATION: Synthetic

<400> SEQUENCE: 38

```
Ile Asn Pro Asp Ser Gly Ala Thr
1               5
```

<210> SEQ ID NO 39
<211> LENGTH: 39
<212> TYPE: DNA
<213> ORGANISM: Artificial Sequence
<220> FEATURE:
<223> OTHER INFORMATION: Synthetic

<400> SEQUENCE: 39
gcgagagata aggatggcag tggctggtac cttgacgac                      39

<210> SEQ ID NO 40
<211> LENGTH: 13
<212> TYPE: PRT
<213> ORGANISM: Artificial Sequence
<220> FEATURE:
<223> OTHER INFORMATION: Synthetic

<400> SEQUENCE: 40

Ala Arg Asp Lys Asp Gly Ser Gly Trp Tyr Leu Asp Asp
 1               5                  10

<210> SEQ ID NO 41
<211> LENGTH: 327
<212> TYPE: DNA
<213> ORGANISM: Artificial Sequence
<220> FEATURE:
<223> OTHER INFORMATION: Synthetic

<400> SEQUENCE: 41
gaaattgtgt tgactcagtc tccagccacc ctgtctttgt ctccagggga aagagccacc      60
ctctcctgca gggccagtca gagtgttaac atctacttag cctggtacca acagaaacct    120
ggccaggctc ccaggctcct catctatgat gcatccaaca gggcctctgg catcccagcc    180
aggttcagtg gcagtgggtc tgggacagac ttcactctca ccatcagcag cctagagcct    240
gaagattttg cagtttatta ctgtcagcag cgtagcaact ggcctccatc gatcaccttc    300
ggccaaggga cacgactgga gattaaa                                        327

<210> SEQ ID NO 42
<211> LENGTH: 109
<212> TYPE: PRT
<213> ORGANISM: Artificial Sequence
<220> FEATURE:
<223> OTHER INFORMATION: Synthetic

<400> SEQUENCE: 42

Glu Ile Val Leu Thr Gln Ser Pro Ala Thr Leu Ser Leu Ser Pro Gly
 1               5                  10                  15

Glu Arg Ala Thr Leu Ser Cys Arg Ala Ser Gln Ser Val Asn Ile Tyr
             20                  25                  30

Leu Ala Trp Tyr Gln Gln Lys Pro Gly Gln Ala Pro Arg Leu Leu Ile
         35                  40                  45

Tyr Asp Ala Ser Asn Arg Ala Ser Gly Ile Pro Ala Arg Phe Ser Gly
     50                  55                  60

Ser Gly Ser Gly Thr Asp Phe Thr Leu Thr Ile Ser Ser Leu Glu Pro
 65                  70                  75                  80

Glu Asp Phe Ala Val Tyr Tyr Cys Gln Gln Arg Ser Asn Trp Pro Pro
                 85                  90                  95

Ser Ile Thr Phe Gly Gln Gly Thr Arg Leu Glu Ile Lys
            100                 105

<210> SEQ ID NO 43
<211> LENGTH: 18
<212> TYPE: DNA
<213> ORGANISM: Artificial Sequence
<220> FEATURE:
<223> OTHER INFORMATION: Synthetic

<400> SEQUENCE: 43
cagagtgtta acatctac                                                   18

<210> SEQ ID NO 44

```
<211> LENGTH: 6
<212> TYPE: PRT
<213> ORGANISM: Artificial Sequence
<220> FEATURE:
<223> OTHER INFORMATION: Synthetic

<400> SEQUENCE: 44

Gln Ser Val Asn Ile Tyr
 1               5

<210> SEQ ID NO 45
<211> LENGTH: 9
<212> TYPE: DNA
<213> ORGANISM: Artificial Sequence
<220> FEATURE:
<223> OTHER INFORMATION: Synthetic

<400> SEQUENCE: 45 gatgcatcc                                                                  9

<210> SEQ ID NO 46
<211> LENGTH: 3
<212> TYPE: PRT
<213> ORGANISM: Artificial Sequence
<220> FEATURE:
<223> OTHER INFORMATION: Synthetic

<400> SEQUENCE: 46

Asp Ala Ser
 1

<210> SEQ ID NO 47
<211> LENGTH: 33
<212> TYPE: DNA
<213> ORGANISM: Artificial Sequence
<220> FEATURE:
<223> OTHER INFORMATION: Synthetic

<400> SEQUENCE: 47
cagcagcgta gcaactggcc tccatcgatc acc                                       33

<210> SEQ ID NO 48
<211> LENGTH: 11
<212> TYPE: PRT
<213> ORGANISM: Artificial Sequence
<220> FEATURE:
<223> OTHER INFORMATION: Synthetic

<400> SEQUENCE: 48

Gln Gln Arg Ser Asn Trp Pro Pro Ser Ile Thr
 1               5                  10

<210> SEQ ID NO 49
<211> LENGTH: 369
<212> TYPE: DNA
<213> ORGANISM: Artificial Sequence
<220> FEATURE:
<223> OTHER INFORMATION: Synthetic

<400> SEQUENCE: 49
cagattcaac tggtgcagtc tggagctgag atgaagaggc ctgggacctc agtgaaggtc          60
tcctgcaagg cctctggtta cacctttttcc agctatggta tcaactgggt gcgtcaggcc        120
cctggacaag ggcttgagtg gatgggatgg atcagcgctt acaatggtga cacaaactat        180
gcacagaaac tccagggcag agtcaccatg accacggaca catccacgac cacagcctat        240
```

```
atggaggtga ggagcctgag atctgacgac acggccgttt attactgtgc gagatttta      300 actggaacta aggacctcta ctacggtatg gacgtctggg gccaaggggac cacggtcacc     360 gtctcctca                                                              369
```

<210> SEQ ID NO 50
<211> LENGTH: 123
<212> TYPE: PRT
<213> ORGANISM: Artificial Sequence
<220> FEATURE:
<223> OTHER INFORMATION: Synthetic

<400> SEQUENCE: 50

```
Gln Ile Gln Leu Val Gln Ser Gly Ala Glu Met Lys Arg Pro Gly Thr
 1               5                  10                  15
Ser Val Lys Val Ser Cys Lys Ala Ser Gly Tyr Thr Phe Ser Ser Tyr
            20                  25                  30
Gly Ile Asn Trp Val Arg Gln Ala Pro Gly Gln Gly Leu Glu Trp Met
        35                  40                  45
Gly Trp Ile Ser Ala Tyr Asn Gly Asp Thr Asn Tyr Ala Gln Lys Leu
    50                  55                  60
Gln Gly Arg Val Thr Met Thr Thr Asp Thr Ser Thr Thr Thr Ala Tyr
65                  70                  75                  80
Met Glu Val Arg Ser Leu Arg Ser Asp Asp Thr Ala Val Tyr Tyr Cys
                85                  90                  95
Ala Arg Phe Leu Thr Gly Thr Lys Asp Leu Tyr Tyr Gly Met Asp Val
            100                 105                 110
Trp Gly Gln Gly Thr Thr Val Thr Val Ser Ser
        115                 120
```

<210> SEQ ID NO 51
<211> LENGTH: 24
<212> TYPE: DNA
<213> ORGANISM: Artificial Sequence
<220> FEATURE:
<223> OTHER INFORMATION: Synthetic

<400> SEQUENCE: 51

```
ggttacacct tttccagcta tggt                                              24
```

<210> SEQ ID NO 52
<211> LENGTH: 8
<212> TYPE: PRT
<213> ORGANISM: Artificial Sequence
<220> FEATURE:
<223> OTHER INFORMATION: Synthetic

<400> SEQUENCE: 52

```
Gly Tyr Thr Phe Ser Ser Tyr Gly
 1               5
```

<210> SEQ ID NO 53
<211> LENGTH: 24
<212> TYPE: DNA
<213> ORGANISM: Artificial Sequence
<220> FEATURE:
<223> OTHER INFORMATION: Synthetic

<400> SEQUENCE: 53

```
atcagcgctt acaatggtga caca                                              24
```

<210> SEQ ID NO 54

```
<211> LENGTH: 8
<212> TYPE: PRT
<213> ORGANISM: Artificial Sequence
<220> FEATURE:
<223> OTHER INFORMATION: Synthetic

<400> SEQUENCE: 54

Ile Ser Ala Tyr Asn Gly Asp Thr
 1               5

<210> SEQ ID NO 55
<211> LENGTH: 48
<212> TYPE: DNA
<213> ORGANISM: Artificial Sequence
<220> FEATURE:
<223> OTHER INFORMATION: Synthetic

<400> SEQUENCE: 55
gcgagatttt taactggaac taaggacctc tactacggta tggacgtc                  48

<210> SEQ ID NO 56
<211> LENGTH: 16
<212> TYPE: PRT
<213> ORGANISM: Artificial Sequence
<220> FEATURE:
<223> OTHER INFORMATION: Synthetic

<400> SEQUENCE: 56

Ala Arg Phe Leu Thr Gly Thr Lys Asp Leu Tyr Tyr Gly Met Asp Val
 1               5                  10                  15

<210> SEQ ID NO 57
<211> LENGTH: 321
<212> TYPE: DNA
<213> ORGANISM: Artificial Sequence
<220> FEATURE:
<223> OTHER INFORMATION: Synthetic

<400> SEQUENCE: 57
gacatccaga tgacccagtc tccatcctcc ctgtctgcat ctgtaggaga cagagtcacc      60
atcacttgcc aggcgagtca ggacattagc aacttttaa attggtatca gcagaaacca     120
gggaaagccc ctgatctcct gatcaacgat gcatccattt tggaaacagg ggtcccatca     180
aggttcagtg gcagtggatc tgggacagat tttactctca ccatcaacag cctgcagcct     240
gaagatattg caacatatta ctgtcaacaa tatgataatc tccctctcac tttcggcgga     300
gggaccaagg tggagatcaa a                                               321

<210> SEQ ID NO 58
<211> LENGTH: 107
<212> TYPE: PRT
<213> ORGANISM: Artificial Sequence
<220> FEATURE:
<223> OTHER INFORMATION: Synthetic

<400> SEQUENCE: 58

Asp Ile Gln Met Thr Gln Ser Pro Ser Ser Leu Ser Ala Ser Val Gly
 1               5                  10                  15

Asp Arg Val Thr Ile Thr Cys Gln Ala Ser Gln Asp Ile Ser Asn Phe
                20                  25                  30

Leu Asn Trp Tyr Gln Gln Lys Pro Gly Lys Ala Pro Asp Leu Leu Ile
            35                  40                  45

Asn Asp Ala Ser Ile Leu Glu Thr Gly Val Pro Ser Arg Phe Ser Gly
        50                  55                  60
```

Ser Gly Ser Gly Thr Asp Phe Thr Leu Thr Ile Asn Ser Leu Gln Pro
65                  70                  75                  80

Glu Asp Ile Ala Thr Tyr Tyr Cys Gln Gln Tyr Asp Asn Leu Pro Leu
                85                  90                  95

Thr Phe Gly Gly Gly Thr Lys Val Glu Ile Lys
            100                 105

<210> SEQ ID NO 59
<211> LENGTH: 18
<212> TYPE: DNA
<213> ORGANISM: Artificial Sequence
<220> FEATURE:
<223> OTHER INFORMATION: Synthetic

<400> SEQUENCE: 59
caggacatta gcaactttt                                              18

<210> SEQ ID NO 60
<211> LENGTH: 6
<212> TYPE: PRT
<213> ORGANISM: Artificial Sequence
<220> FEATURE:
<223> OTHER INFORMATION: Synthetic

<400> SEQUENCE: 60

Gln Asp Ile Ser Asn Phe
1               5

<210> SEQ ID NO 61
<211> LENGTH: 9
<212> TYPE: DNA
<213> ORGANISM: Artificial Sequence
<220> FEATURE:
<223> OTHER INFORMATION: Synthetic

<400> SEQUENCE: 61 gatgcatcc                                                          9

<210> SEQ ID NO 62
<211> LENGTH: 3
<212> TYPE: PRT
<213> ORGANISM: Artificial Sequence
<220> FEATURE:
<223> OTHER INFORMATION: Synthetic

<400> SEQUENCE: 62

Asp Ala Ser
1

<210> SEQ ID NO 63
<211> LENGTH: 27
<212> TYPE: DNA
<213> ORGANISM: Artificial Sequence
<220> FEATURE:
<223> OTHER INFORMATION: Synthetic

<400> SEQUENCE: 63
caacaatatg ataatctccc tctcact                                     27

<210> SEQ ID NO 64
<211> LENGTH: 9
<212> TYPE: PRT
<213> ORGANISM: Artificial Sequence
<220> FEATURE:
<223> OTHER INFORMATION: Synthetic -continued

<400> SEQUENCE: 64

Gln Gln Tyr Asp Asn Leu Pro Leu Thr
1               5

<210> SEQ ID NO 65
<211> LENGTH: 351
<212> TYPE: DNA
<213> ORGANISM: Artificial Sequence
<220> FEATURE:
<223> OTHER INFORMATION: Synthetic

<400> SEQUENCE: 65
caggtgcagt tggtgcagtc tggggctgag gtgaagaagc ctggggcctc agtgaaggtt      60
tcctgcaagg catctggaca ccccttcacc aactactaca ttcactgggt gcgacaggcc     120
cctggacaag ggcttgaatg gatgggaata accaacccta atgatggtaa cacaagatac     180
gcacagaagt tccagggcag aatctccatg acctgggaca cgtccacgag cacagtcttc     240
atggaactga gcagcctaaa atctgaggac acggccgtgt attactgtgc gggacttcgc     300
tactggttct tcgatctctg gggccgtggc accccggtca ctgtctcctc a              351

<210> SEQ ID NO 66
<211> LENGTH: 117
<212> TYPE: PRT
<213> ORGANISM: Artificial Sequence
<220> FEATURE:
<223> OTHER INFORMATION: Synthetic

<400> SEQUENCE: 66

Gln Val Gln Leu Val Gln Ser Gly Ala Glu Val Lys Lys Pro Gly Ala
1               5                   10                  15

Ser Val Lys Val Ser Cys Lys Ala Ser Gly His Thr Phe Thr Asn Tyr
                20                  25                  30

Tyr Ile His Trp Val Arg Gln Ala Pro Gly Gln Gly Leu Glu Trp Met
            35                  40                  45

Gly Ile Thr Asn Pro Asn Asp Gly Asn Thr Arg Tyr Ala Gln Lys Phe
        50                  55                  60

Gln Gly Arg Ile Ser Met Thr Trp Asp Thr Ser Thr Ser Thr Val Phe
65                  70                  75                  80

Met Glu Leu Ser Ser Leu Lys Ser Glu Asp Thr Ala Val Tyr Tyr Cys
                85                  90                  95

Ala Gly Leu Arg Tyr Trp Phe Phe Asp Leu Trp Gly Arg Gly Thr Pro
            100                 105                 110

Val Thr Val Ser Ser
        115

<210> SEQ ID NO 67
<211> LENGTH: 24
<212> TYPE: DNA
<213> ORGANISM: Artificial Sequence
<220> FEATURE:
<223> OTHER INFORMATION: Synthetic

<400> SEQUENCE: 67
ggacacacct tcaccaacta ctac                                             24

<210> SEQ ID NO 68
<211> LENGTH: 8
<212> TYPE: PRT
<213> ORGANISM: Artificial Sequence
<220> FEATURE:
<223> OTHER INFORMATION: Synthetic

<400> SEQUENCE: 68

Gly His Thr Phe Thr Asn Tyr Tyr
 1               5

<210> SEQ ID NO 69
<211> LENGTH: 24
<212> TYPE: DNA
<213> ORGANISM: Artificial Sequence
<220> FEATURE:
<223> OTHER INFORMATION: Synthetic

<400> SEQUENCE: 69
accaacccta atgatggtaa caca                                           24

<210> SEQ ID NO 70
<211> LENGTH: 8
<212> TYPE: PRT
<213> ORGANISM: Artificial Sequence
<220> FEATURE:
<223> OTHER INFORMATION: Synthetic

<400> SEQUENCE: 70

Thr Asn Pro Asn Asp Gly Asn Thr
 1               5

<210> SEQ ID NO 71
<211> LENGTH: 30
<212> TYPE: DNA
<213> ORGANISM: Artificial Sequence
<220> FEATURE:
<223> OTHER INFORMATION: Synthetic

<400> SEQUENCE: 71
gcgggacttc gctactggtt cttcgatctc                                     30

<210> SEQ ID NO 72
<211> LENGTH: 10
<212> TYPE: PRT
<213> ORGANISM: Artificial Sequence
<220> FEATURE:
<223> OTHER INFORMATION: Synthetic

<400> SEQUENCE: 72

Ala Gly Leu Arg Tyr Trp Phe Phe Asp Leu
 1               5                  10

<210> SEQ ID NO 73
<211> LENGTH: 321
<212> TYPE: DNA
<213> ORGANISM: Artificial Sequence
<220> FEATURE:
<223> OTHER INFORMATION: Synthetic

<400> SEQUENCE: 73
gacatccaga tgacccagtc tccatcttcc gtgtctgcat ctgtaggaga cagagtcacc     60
atcacttgtc gggcgagcca ggatattagc agctggttag cctggtatca gcagaaacca    120
gggaaagccc ctaacctcct gatctttgct gcatccagtt tgcaaagtgg ggtcccatca    180
aggttcagcg gcagtggatc tgggacagat tcactctca ccatcagcag cctgcagcct    240
gaagattttg aacttactact ttgtcaacag actgacaatt tccctcggac gttcggccaa    300
gggaccaagg tggaaatcaa c                                             321

<210> SEQ ID NO 74
<211> LENGTH: 107
<212> TYPE: PRT
<213> ORGANISM: Artificial Sequence
<220> FEATURE:
<223> OTHER INFORMATION: Synthetic

<400> SEQUENCE: 74

```
Asp Ile Gln Met Thr Gln Ser Pro Ser Ser Val Ser Ala Ser Val Gly
 1               5                  10                  15

Asp Arg Val Thr Ile Thr Cys Arg Ala Ser Gln Asp Ile Ser Ser Trp
            20                  25                  30

Leu Ala Trp Tyr Gln Gln Lys Pro Gly Lys Ala Pro Asn Leu Leu Ile
        35                  40                  45

Phe Ala Ala Ser Ser Leu Gln Ser Gly Val Pro Ser Arg Phe Ser Gly
 50                  55                  60

Ser Gly Ser Gly Thr Asp Phe Thr Leu Thr Ile Ser Ser Leu Gln Pro
 65                  70                  75                  80

Glu Asp Phe Gly Thr Tyr Tyr Cys Gln Gln Thr Asp Asn Phe Pro Arg
                85                  90                  95

Thr Phe Gly Gln Gly Thr Lys Val Glu Ile Asn
            100                 105
```

<210> SEQ ID NO 75
<211> LENGTH: 18
<212> TYPE: DNA
<213> ORGANISM: Artificial Sequence
<220> FEATURE:
<223> OTHER INFORMATION: Synthetic

<400> SEQUENCE: 75
caggatatta gcagctgg                                                   18

<210> SEQ ID NO 76
<211> LENGTH: 6
<212> TYPE: PRT
<213> ORGANISM: Artificial Sequence
<220> FEATURE:
<223> OTHER INFORMATION: Synthetic

<400> SEQUENCE: 76

```
Gln Asp Ile Ser Ser Trp
 1               5
```

<210> SEQ ID NO 77
<211> LENGTH: 9
<212> TYPE: DNA
<213> ORGANISM: Artificial Sequence
<220> FEATURE:
<223> OTHER INFORMATION: Synthetic

<400> SEQUENCE: 77 gctgcatcc                                                              9

<210> SEQ ID NO 78
<211> LENGTH: 3
<212> TYPE: PRT
<213> ORGANISM: Artificial Sequence
<220> FEATURE:
<223> OTHER INFORMATION: Synthetic

<400> SEQUENCE: 78

Ala Ala Ser
1

<210> SEQ ID NO 79
<211> LENGTH: 27
<212> TYPE: DNA
<213> ORGANISM: Artificial Sequence
<220> FEATURE:
<223> OTHER INFORMATION: Synthetic

<400> SEQUENCE: 79
caacagactg acaatttccc tcggacg                                        27

<210> SEQ ID NO 80
<211> LENGTH: 9
<212> TYPE: PRT
<213> ORGANISM: Artificial Sequence
<220> FEATURE:
<223> OTHER INFORMATION: Synthetic

<400> SEQUENCE: 80

Gln Gln Thr Asp Asn Phe Pro Arg Thr
1               5

<210> SEQ ID NO 81
<211> LENGTH: 369
<212> TYPE: DNA
<213> ORGANISM: Artificial Sequence
<220> FEATURE:
<223> OTHER INFORMATION: Synthetic

<400> SEQUENCE: 81
cagattcaac tggtgcagtc tggagctgag atgaagaggc ctgggacctc agtgaaggtc     60
tcctgcaagg cctctggtta cacctttacc agctatggta tcaactgggt gcgtcaggcc    120
cctggacaag ggcttgagtg gatgggatgg atcagcgctt acaatggtga cacaaactat    180
gcacagaaac tccagggcag agtcaccatg accacggaca catccacgac acagcctat    240 atggaggtga ggagcctgag atctgacgac acggccgttt attactgtgc gagattttta    300
actggaacta aggactacta ctacggtatg gacgtctggg gccaagggac cacggtcacc    360
gtctcctca                                                            369

<210> SEQ ID NO 82
<211> LENGTH: 123
<212> TYPE: PRT
<213> ORGANISM: Artificial Sequence
<220> FEATURE:
<223> OTHER INFORMATION: Synthetic

<400> SEQUENCE: 82

Gln Ile Gln Leu Val Gln Ser Gly Ala Glu Met Lys Arg Pro Gly Thr
1               5                   10                  15

Ser Val Lys Val Ser Cys Lys Ala Ser Gly Tyr Thr Phe Thr Ser Tyr
                20                  25                  30

Gly Ile Asn Trp Val Arg Gln Ala Pro Gly Gln Gly Leu Glu Trp Met
            35                  40                  45

Gly Trp Ile Ser Ala Tyr Asn Gly Asp Thr Asn Tyr Ala Gln Lys Leu
        50                  55                  60

Gln Gly Arg Val Thr Met Thr Thr Asp Thr Ser Thr Thr Thr Ala Tyr
65                  70                  75                  80

Met Glu Val Arg Ser Leu Arg Ser Asp Asp Thr Ala Val Tyr Tyr Cys
                85                  90                  95

Ala Arg Phe Leu Thr Gly Thr Lys Asp Tyr Tyr Tyr Gly Met Asp Val
            100                 105                 110

Trp Gly Gln Gly Thr Thr Val Thr Val Ser Ser
        115                 120

<210> SEQ ID NO 83
<211> LENGTH: 24
<212> TYPE: DNA
<213> ORGANISM: Artificial Sequence
<220> FEATURE:
<223> OTHER INFORMATION: Synthetic

<400> SEQUENCE: 83
ggttacacct ttaccagcta tggt                                          24

<210> SEQ ID NO 84
<211> LENGTH: 8
<212> TYPE: PRT
<213> ORGANISM: Artificial Sequence
<220> FEATURE:
<223> OTHER INFORMATION: Synthetic

<400> SEQUENCE: 84

Gly Tyr Thr Phe Thr Ser Tyr Gly
 1               5

<210> SEQ ID NO 85
<211> LENGTH: 24
<212> TYPE: DNA
<213> ORGANISM: Artificial Sequence
<220> FEATURE:
<223> OTHER INFORMATION: Synthetic

<400> SEQUENCE: 85
atcagcgctt acaatggtga caca                                          24

<210> SEQ ID NO 86
<211> LENGTH: 8
<212> TYPE: PRT
<213> ORGANISM: Artificial Sequence
<220> FEATURE:
<223> OTHER INFORMATION: Synthetic

<400> SEQUENCE: 86

Ile Ser Ala Tyr Asn Gly Asp Thr
 1               5

<210> SEQ ID NO 87
<211> LENGTH: 48
<212> TYPE: DNA
<213> ORGANISM: Artificial Sequence
<220> FEATURE:
<223> OTHER INFORMATION: Synthetic

<400> SEQUENCE: 87
gcgagatttt taactggaac taaggactac tactacggta tggacgtc               48

<210> SEQ ID NO 88
<211> LENGTH: 16
<212> TYPE: PRT
<213> ORGANISM: Artificial Sequence
<220> FEATURE:
<223> OTHER INFORMATION: Synthetic

<400> SEQUENCE: 88

```
Ala Arg Phe Leu Thr Gly Thr Lys Asp Tyr Tyr Gly Met Asp Val
1               5                   10                  15
```

<210> SEQ ID NO 89
<211> LENGTH: 321
<212> TYPE: DNA
<213> ORGANISM: Artificial Sequence
<220> FEATURE:
<223> OTHER INFORMATION: Synthetic

<400> SEQUENCE: 89

```
gacatccaga tgacccagtc tccatcctcc ctgtctgcat ctgtaggaga cagagtcacc    60
atcacttgcc aggcgagtca ggacattagc aacttttaa attggtatca gcagaaacca   120
gggaaagccc ctgatctcct gatcaacgat gcatccattt tggaaacagg ggtcccatca   180
aggttcagtg aagtggatc tgggacagat tttactctca ccatcaacaa cctgcagcct   240
gaagatattg caacatatta ctgtcaacaa tatgataatc tccctctcac tttcggcgga   300
gggaccaagg tagagatcaa a                                             321
```

<210> SEQ ID NO 90
<211> LENGTH: 107
<212> TYPE: PRT
<213> ORGANISM: Artificial Sequence
<220> FEATURE:
<223> OTHER INFORMATION: Synthetic

<400> SEQUENCE: 90

```
Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Asp Ile Ser Asn Phe
                20                  25                  30

Leu Asn Trp Tyr Gln Gln Lys Pro Gly Lys Ala Pro Asp Leu Leu Ile
            35                  40                  45

Asn Asp Ala Ser Ile Leu Glu Thr Gly Val Pro Ser Arg Phe Ser Gly
        50                  55                  60

Ser Gly Ser Gly Thr Asp Phe Thr Leu Thr Ile Asn Asn Leu Gln Pro
65                  70                  75                  80

Glu Asp Ile Ala Thr Tyr Tyr Cys Gln Gln Tyr Asp Asn Leu Pro Leu
                85                  90                  95

Thr Phe Gly Gly Gly Thr Lys Val Glu Ile Lys
            100                 105
```

<210> SEQ ID NO 91
<211> LENGTH: 18
<212> TYPE: DNA
<213> ORGANISM: Artificial Sequence
<220> FEATURE:
<223> OTHER INFORMATION: Synthetic

<400> SEQUENCE: 91

```
caggacatta gcaacttt                                                  18
```

<210> SEQ ID NO 92
<211> LENGTH: 6
<212> TYPE: PRT
<213> ORGANISM: Artificial Sequence
<220> FEATURE:
<223> OTHER INFORMATION: Synthetic

<400> SEQUENCE: 92

Gln Asp Ile Ser Asn Phe

<210> SEQ ID NO 93
<211> LENGTH: 9
<212> TYPE: DNA
<213> ORGANISM: Artificial Sequence
<220> FEATURE:
<223> OTHER INFORMATION: Synthetic

<400> SEQUENCE: 93 gatgcatcc                                                                   9

<210> SEQ ID NO 94
<211> LENGTH: 3
<212> TYPE: PRT
<213> ORGANISM: Artificial Sequence
<220> FEATURE:
<223> OTHER INFORMATION: Synthetic

<400> SEQUENCE: 94

Asp Ala Ser
 1

<210> SEQ ID NO 95
<211> LENGTH: 27
<212> TYPE: DNA
<213> ORGANISM: Artificial Sequence
<220> FEATURE:
<223> OTHER INFORMATION: Synthetic

<400> SEQUENCE: 95
caacaatatg ataatctccc tctcact                                              27

<210> SEQ ID NO 96
<211> LENGTH: 9
<212> TYPE: PRT
<213> ORGANISM: Artificial Sequence
<220> FEATURE:
<223> OTHER INFORMATION: Synthetic

<400> SEQUENCE: 96

Gln Gln Tyr Asp Asn Leu Pro Leu Thr
 1               5

<210> SEQ ID NO 97
<211> LENGTH: 363
<212> TYPE: DNA
<213> ORGANISM: Artificial Sequence
<220> FEATURE:
<223> OTHER INFORMATION: Synthetic

<400> SEQUENCE: 97
caggtgcagc tggtggagtc tgggggaggc gtggtccagc ctggggaggtc cctgagactc          60 tcctgtgcag cgtctggatt caccttcagt gactatggca tgcactgggt ccgccaggct         120
ccaggcaagg ggctggagtg ggtggcagtt atatggaatg atggaagtaa taaaaattat         180
gcagactccg tgaagggccg attcagcatc tccagtgaca gttccaagaa cacgctgtat         240
ctacatatga acagcctgag agccgaggac acggctgtgt attactgtgc gagatcgttg         300
tatagtacca gtccctggta tttcgatctc tggggccgtg gcaccctggt cactgtctcc         360
tca                                                                      363

<210> SEQ ID NO 98
<211> LENGTH: 121

<212> TYPE: PRT
<213> ORGANISM: Artificial Sequence
<220> FEATURE:
<223> OTHER INFORMATION: Synthetic

<400> SEQUENCE: 98

```
Gln Val Gln Leu Val Glu Ser Gly Gly Gly Val Val Gln Pro Gly Arg
 1               5                  10                  15

Ser Leu Arg Leu Ser Cys Ala Ala Ser Gly Phe Thr Phe Ser Asp Tyr
            20                  25                  30

Gly Met His Trp Val Arg Gln Ala Pro Gly Lys Gly Leu Glu Trp Val
        35                  40                  45

Ala Val Ile Trp Asn Asp Gly Ser Asn Lys Asn Tyr Ala Asp Ser Val
    50                  55                  60

Lys Gly Arg Phe Ser Ile Ser Ser Asp Ser Lys Asn Thr Leu Tyr
65                  70                  75                  80

Leu His Met Asn Ser Leu Arg Ala Glu Asp Thr Ala Val Tyr Tyr Cys
                85                  90                  95

Ala Arg Ser Leu Tyr Ser Thr Ser Pro Trp Tyr Phe Asp Leu Trp Gly
            100                 105                 110

Arg Gly Thr Leu Val Thr Val Ser Ser
        115                 120
```

<210> SEQ ID NO 99
<211> LENGTH: 24
<212> TYPE: DNA
<213> ORGANISM: Artificial Sequence
<220> FEATURE:
<223> OTHER INFORMATION: Synthetic

<400> SEQUENCE: 99
ggattcacct tcagtgacta tggc                                    24

<210> SEQ ID NO 100
<211> LENGTH: 8
<212> TYPE: PRT
<213> ORGANISM: Artificial Sequence
<220> FEATURE:
<223> OTHER INFORMATION: Synthetic

<400> SEQUENCE: 100

```
Gly Phe Thr Phe Ser Asp Tyr Gly
 1               5
```

<210> SEQ ID NO 101
<211> LENGTH: 24
<212> TYPE: DNA
<213> ORGANISM: Artificial Sequence
<220> FEATURE:
<223> OTHER INFORMATION: Synthetic

<400> SEQUENCE: 101
atatggaatg atggaagtaa taaa                                    24

<210> SEQ ID NO 102
<211> LENGTH: 8
<212> TYPE: PRT
<213> ORGANISM: Artificial Sequence
<220> FEATURE:
<223> OTHER INFORMATION: Synthetic

<400> SEQUENCE: 102

Ile Trp Asn Asp Gly Ser Asn Lys

<210> SEQ ID NO 103
<211> LENGTH: 42
<212> TYPE: DNA
<213> ORGANISM: Artificial Sequence
<220> FEATURE:
<223> OTHER INFORMATION: Synthetic

<400> SEQUENCE: 103
gcgagatcgt tgtatagtac cagtccctgg tatttcgatc tc                    42

<210> SEQ ID NO 104
<211> LENGTH: 14
<212> TYPE: PRT
<213> ORGANISM: Artificial Sequence
<220> FEATURE:
<223> OTHER INFORMATION: Synthetic

<400> SEQUENCE: 104

Ala Arg Ser Leu Tyr Ser Thr Ser Pro Trp Tyr Phe Asp Tyr
 1               5                  10

<210> SEQ ID NO 105
<211> LENGTH: 318
<212> TYPE: DNA
<213> ORGANISM: Artificial Sequence
<220> FEATURE:
<223> OTHER INFORMATION: Synthetic

<400> SEQUENCE: 105
gacatccaga tgacccagtc tccatcctcc ctgtctgcat ctgtaggaga cagagtcacc    60
atcacttgcc gggcaagtca gagcattagc agctatttaa attggtatca ggagaaatca   120
gggaaagccc ctaagctcct gatctatgct gcatccagtt tgcaaagtgg ggtcccatca   180
aggttcagtg gcagtggatc tgggacagat tcactctca ccatcagcag tctgcaacct    240
gaagattttg caacttacta ctgtcaacag agttacagta ccccccacttt cggcggaggg   300 accaaggtgg agatcaaa                                                318

<210> SEQ ID NO 106
<211> LENGTH: 106
<212> TYPE: PRT
<213> ORGANISM: Artificial Sequence
<220> FEATURE:
<223> OTHER INFORMATION: Synthetic

<400> SEQUENCE: 106

Asp Ile Gln Met Thr Gln Ser Pro Ser Ser Leu Ser Ala Ser Val Gly
 1               5                  10                  15

Asp Arg Val Thr Ile Thr Cys Arg Ala Ser Gln Ser Ile Ser Ser Tyr
             20                  25                  30

Leu Asn Trp Tyr Gln Glu Lys Ser Gly Lys Ala Pro Lys Leu Leu Ile
         35                  40                  45

Tyr Ala Ala Ser Ser Leu Gln Ser Gly Val Pro Ser Arg Phe Ser Gly
     50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Ser Tyr Ser Thr Pro Thr
                 85                  90                  95

Phe Gly Gly Gly Thr Lys Val Glu Ile Lys
            100                 105

<210> SEQ ID NO 107
<211> LENGTH: 18
<212> TYPE: DNA
<213> ORGANISM: Artificial Sequence
<220> FEATURE:
<223> OTHER INFORMATION: Synthetic

<400> SEQUENCE: 107
cagagcatta gcagctat                                                   18

<210> SEQ ID NO 108
<211> LENGTH: 6
<212> TYPE: PRT
<213> ORGANISM: Artificial Sequence
<220> FEATURE:
<223> OTHER INFORMATION: Synthetic

<400> SEQUENCE: 108

Gln Ser Ile Ser Ser Tyr
 1               5

<210> SEQ ID NO 109
<211> LENGTH: 9
<212> TYPE: DNA
<213> ORGANISM: Artificial Sequence
<220> FEATURE:
<223> OTHER INFORMATION: Synthetic

<400> SEQUENCE: 109 gctgcatcc                                                              9

<210> SEQ ID NO 110
<211> LENGTH: 3
<212> TYPE: PRT
<213> ORGANISM: Artificial Sequence
<220> FEATURE:
<223> OTHER INFORMATION: Synthetic

<400> SEQUENCE: 110

Ala Ala Ser
 1

<210> SEQ ID NO 111
<211> LENGTH: 24
<212> TYPE: DNA
<213> ORGANISM: Artificial Sequence
<220> FEATURE:
<223> OTHER INFORMATION: Synthetic

<400> SEQUENCE: 111
caacagagtt acagtacccc cact                                            24

<210> SEQ ID NO 112
<211> LENGTH: 8
<212> TYPE: PRT
<213> ORGANISM: Artificial Sequence
<220> FEATURE:
<223> OTHER INFORMATION: Synthetic

<400> SEQUENCE: 112

Gln Gln Ser Tyr Ser Thr Pro Thr
 1               5

<210> SEQ ID NO 113
<211> LENGTH: 360

```
<212> TYPE: DNA
<213> ORGANISM: Artificial Sequence
<220> FEATURE:
<223> OTHER INFORMATION: Synthetic

<400> SEQUENCE: 113
caggtacaac tggtgcagtc tggggctgag gcgagggagc ctggggcctc agtgagggtc      60
tcctgcaagg cctctggata caccttcacc gactacttta ttcactgggt gcgacaggcc     120
cctggacaag gcttgagtg gatgggatgg atcaaccca acagtggtgc cacaaacttt       180
gcacagaagt tcagggcag ggtcaccatg accaggaca cgtccctcat tacagcctac       240
atggacctga gcaggctgaa atctgacgac gcggccgtgt tttactgtgc gagagatgtg     300
gatggcagtg gctggtacct tgacttttgg ggccagggaa ccctggtcac cgtctcctca     360

<210> SEQ ID NO 114
<211> LENGTH: 120
<212> TYPE: PRT
<213> ORGANISM: Artificial Sequence
<220> FEATURE:
<223> OTHER INFORMATION: Synthetic

<400> SEQUENCE: 114

Gln Val Gln Leu Val Gln Ser Gly Ala Glu Ala Arg Glu Pro Gly Ala
1               5                   10                  15

Ser Val Arg Val Ser Cys Lys Ala Ser Gly Tyr Thr Phe Thr Asp Tyr
            20                  25                  30

Phe Ile His Trp Val Arg Gln Ala Pro Gly Gln Gly Leu Glu Trp Met
        35                  40                  45

Gly Trp Ile Asn Pro Asn Ser Gly Ala Thr Asn Phe Ala Gln Lys Phe
    50                  55                  60

Gln Gly Arg Val Thr Met Thr Arg Asp Thr Ser Leu Ile Thr Ala Tyr
65                  70                  75                  80

Met Asp Leu Ser Arg Leu Lys Ser Asp Asp Ala Ala Val Phe Tyr Cys
                85                  90                  95

Ala Arg Asp Val Asp Gly Ser Gly Trp Tyr Leu Asp Phe Trp Gly Gln
            100                 105                 110

Gly Thr Leu Val Thr Val Ser Ser
        115                 120

<210> SEQ ID NO 115
<211> LENGTH: 24
<212> TYPE: DNA
<213> ORGANISM: Artificial Sequence
<220> FEATURE:
<223> OTHER INFORMATION: Synthetic

<400> SEQUENCE: 115
ggatacacct tcaccgacta cttt                                             24

<210> SEQ ID NO 116
<211> LENGTH: 8
<212> TYPE: PRT
<213> ORGANISM: Artificial Sequence
<220> FEATURE:
<223> OTHER INFORMATION: Synthetic

<400> SEQUENCE: 116

Gly Tyr Thr Phe Thr Asp Tyr Phe
1               5
```

```
<210> SEQ ID NO 117
<211> LENGTH: 24
<212> TYPE: DNA
<213> ORGANISM: Artificial Sequence
<220> FEATURE:
<223> OTHER INFORMATION: Synthetic

<400> SEQUENCE: 117 atcaaccctaa acagtggtgc caca                                           24

<210> SEQ ID NO 118
<211> LENGTH: 8
<212> TYPE: PRT
<213> ORGANISM: Artificial Sequence
<220> FEATURE:
<223> OTHER INFORMATION: Synthetic

<400> SEQUENCE: 118

Ile Asn Pro Asn Ser Gly Ala Thr
 1               5

<210> SEQ ID NO 119
<211> LENGTH: 39
<212> TYPE: DNA
<213> ORGANISM: Artificial Sequence
<220> FEATURE:
<223> OTHER INFORMATION: Synthetic

<400> SEQUENCE: 119
gcgagagatg tggatggcag tggctggtac cttgacttt                            39

<210> SEQ ID NO 120
<211> LENGTH: 13
<212> TYPE: PRT
<213> ORGANISM: Artificial Sequence
<220> FEATURE:
<223> OTHER INFORMATION: Synthetic

<400> SEQUENCE: 120

Ala Arg Asp Val Asp Gly Ser Gly Trp Tyr Leu Asp Phe
 1               5                   10

<210> SEQ ID NO 121
<211> LENGTH: 327
<212> TYPE: DNA
<213> ORGANISM: Artificial Sequence
<220> FEATURE:
<223> OTHER INFORMATION: Synthetic

<400> SEQUENCE: 121
gaaattgtgt tgactcagtc tccagccacc ctgtctttgt ctccagggga aagagccacc     60
ctctcctgca gggccagtca gagtgttagc atctacttag cctggtacca acagaaacct    120
ggccaggctc ccaggctcct catctatgat gcatccaaca gggccactgg catcccagcc    180
aggttcagtg gcagtgggtc tgggacagac ttcactctca ccatcagcag gttagagcct    240
gaagattttg cagtttatta ctgtcagcag cgtagcgact ggcctccatc gatcaccttc    300
ggccaaggga cacgactgga gattaaa                                       327

<210> SEQ ID NO 122
<211> LENGTH: 109
<212> TYPE: PRT
<213> ORGANISM: Artificial Sequence
<220> FEATURE:
<223> OTHER INFORMATION: Synthetic
```

<400> SEQUENCE: 122

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ile Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
50                  55                  60

Ser Gly Ser Gly Thr Asp Phe Thr Leu Thr Ile Ser Arg Leu Glu Pro
65                  70                  75                  80

Glu Asp Phe Ala Val Tyr Tyr Cys Gln Gln Arg Ser Asp Trp Pro Pro
                85                  90                  95

Ser Ile Thr Phe Gly Gln Gly Thr Arg Leu Glu Ile Lys
            100                 105

<210> SEQ ID NO 123
<211> LENGTH: 18
<212> TYPE: DNA
<213> ORGANISM: Artificial Sequence
<220> FEATURE:
<223> OTHER INFORMATION: Synthetic

<400> SEQUENCE: 123
cagagtgtta gcatctac                                                        18

<210> SEQ ID NO 124
<211> LENGTH: 6
<212> TYPE: PRT
<213> ORGANISM: Artificial Sequence
<220> FEATURE:
<223> OTHER INFORMATION: Synthetic

<400> SEQUENCE: 124

Gln Ser Val Ser Ile Tyr
1               5

<210> SEQ ID NO 125
<211> LENGTH: 9
<212> TYPE: DNA
<213> ORGANISM: Artificial Sequence
<220> FEATURE:
<223> OTHER INFORMATION: Synthetic

<400> SEQUENCE: 125 gatgcatcc                                                                   9

<210> SEQ ID NO 126
<211> LENGTH: 3
<212> TYPE: PRT
<213> ORGANISM: Artificial Sequence
<220> FEATURE:
<223> OTHER INFORMATION: Synthetic

<400> SEQUENCE: 126

Asp Ala Ser
1

<210> SEQ ID NO 127
<211> LENGTH: 33
<212> TYPE: DNA
<213> ORGANISM: Artificial Sequence
<220> FEATURE:

<223> OTHER INFORMATION: Synthetic

<400> SEQUENCE: 127
cagcagcgta gcgactggcc tccatcgatc acc    33

<210> SEQ ID NO 128
<211> LENGTH: 11
<212> TYPE: PRT
<213> ORGANISM: Artificial Sequence
<220> FEATURE:
<223> OTHER INFORMATION: Synthetic

<400> SEQUENCE: 128

Gln Gln Arg Ser Asp Trp Pro Pro Ser Ile Thr
 1               5                  10

<210> SEQ ID NO 129
<211> LENGTH: 384
<212> TYPE: DNA
<213> ORGANISM: Artificial Sequence
<220> FEATURE:
<223> OTHER INFORMATION: Synthetic

<400> SEQUENCE: 129
gaggtgcagt tggtggagtc tgggggaggc ttggcacagc ctggagggtc cctgagactg    60
tcctgtgcag cctctggatt caccttcagt agttatgaga tgaactgggt ccgccaggct   120
ccagggaagg ggctggagtg ggtttcatac attactacta gtggtagcac catatactac   180
gcagactctg tgaagggccg attcaccatg tccagagaca cgccaagaa gtcactgtat   240 ctggaaatga acagcctgag agccgaggac acggctgttt attactgtgc gagagaagag   300
tgtactaatg gtgtatgtta taaagactac cagtactacg gtatggacgt ctggggccaa   360
gggaccacgg tcaccgtctc ctca    384

<210> SEQ ID NO 130
<211> LENGTH: 128
<212> TYPE: PRT
<213> ORGANISM: Artificial Sequence
<220> FEATURE:
<223> OTHER INFORMATION: Synthetic

<400> SEQUENCE: 130

Glu Val Gln Leu Val Glu Ser Gly Gly Gly Leu Ala Gln Pro Gly Gly
 1               5                  10                  15

Ser Leu Arg Leu Ser Cys Ala Ala Ser Gly Phe Thr Phe Ser Ser Tyr
            20                  25                  30

Glu Met Asn Trp Val Arg Gln Ala Pro Gly Lys Gly Leu Glu Trp Val
        35                  40                  45

Ser Tyr Ile Thr Thr Ser Gly Ser Thr Ile Tyr Tyr Ala Asp Ser Val
    50                  55                  60

Lys Gly Arg Phe Thr Met Ser Arg Asp Asn Ala Lys Lys Ser Leu Tyr
65                  70                  75                  80

Leu Glu Met Asn Ser Leu Arg Ala Glu Asp Thr Ala Val Tyr Tyr Cys
                85                  90                  95

Ala Arg Glu Glu Cys Thr Asn Gly Val Cys Tyr Lys Asp Tyr Gln Tyr
            100                 105                 110

Tyr Gly Met Asp Val Trp Gly Gln Gly Thr Thr Val Thr Val Ser Ser
        115                 120                 125

<210> SEQ ID NO 131

```
<211> LENGTH: 24
<212> TYPE: DNA
<213> ORGANISM: Artificial Sequence
<220> FEATURE:
<223> OTHER INFORMATION: Synthetic

<400> SEQUENCE: 131
ggattcacct tcagtagtta tgag                                          24

<210> SEQ ID NO 132
<211> LENGTH: 8
<212> TYPE: PRT
<213> ORGANISM: Artificial Sequence
<220> FEATURE:
<223> OTHER INFORMATION: Synthetic

<400> SEQUENCE: 132

Gly Phe Thr Phe Ser Ser Tyr Glu
 1               5

<210> SEQ ID NO 133
<211> LENGTH: 24
<212> TYPE: DNA
<213> ORGANISM: Artificial Sequence
<220> FEATURE:
<223> OTHER INFORMATION: Synthetic

<400> SEQUENCE: 133
attactacta gtggtagcac cata                                          24

<210> SEQ ID NO 134
<211> LENGTH: 8
<212> TYPE: PRT
<213> ORGANISM: Artificial Sequence
<220> FEATURE:
<223> OTHER INFORMATION: Synthetic

<400> SEQUENCE: 134

Ile Thr Thr Ser Gly Ser Thr Ile
 1               5

<210> SEQ ID NO 135
<211> LENGTH: 63
<212> TYPE: DNA
<213> ORGANISM: Artificial Sequence
<220> FEATURE:
<223> OTHER INFORMATION: Synthetic

<400> SEQUENCE: 135
gcgagagaag agtgtactaa tggtgtatgt tataaagact accagtacta cggtatggac    60
gtc                                                                 63

<210> SEQ ID NO 136
<211> LENGTH: 21
<212> TYPE: PRT
<213> ORGANISM: Artificial Sequence
<220> FEATURE:
<223> OTHER INFORMATION: Synthetic

<400> SEQUENCE: 136

Ala Arg Glu Glu Cys Thr Asn Gly Val Cys Tyr Lys Asp Tyr Gln Tyr
 1               5                  10                  15

Tyr Gly Met Asp Val
             20
```

<210> SEQ ID NO 137
<211> LENGTH: 321
<212> TYPE: DNA
<213> ORGANISM: Artificial Sequence
<220> FEATURE:
<223> OTHER INFORMATION: Synthetic

<400> SEQUENCE: 137

```
gacatccaga tgacccagtc tccatcttcc gtgtctgcat ctgtaggtga cagagtcacc      60
atcacttgtc gggcgagtca gaatattaac acctggttag cctggtatca gcagaaacca     120
gggaaagtcc ctaagctcct gatctatgct gcatccagtt tgcaaagtgg ggtcccatca     180
agattcagcg gcagtggatc tgggacagat ttcactctca ccatcagcag cctgcagcct     240
gaagattttg caacttacta ttgtcaacag gctaacagtt ccctctcac tttcggcgga     300
gggaccaagg tggagatcaa a                                               321
```

<210> SEQ ID NO 138
<211> LENGTH: 107
<212> TYPE: PRT
<213> ORGANISM: Artificial Sequence
<220> FEATURE:
<223> OTHER INFORMATION: Synthetic

<400> SEQUENCE: 138

Asp Ile Gln Met Thr Gln Ser Pro Ser Ser Val Ser Ala Ser Val Gly
1               5                   10                  15

Asp Arg Val Thr Ile Thr Cys Arg Ala Ser Gln Asn Ile Asn Thr Trp
            20                  25                  30

Leu Ala Trp Tyr Gln Gln Lys Pro Gly Lys Val Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ala Asn Ser Phe Pro Leu
                85                  90                  95

Thr Phe Gly Gly Gly Thr Lys Val Glu Ile Lys
            100                 105

<210> SEQ ID NO 139
<211> LENGTH: 18
<212> TYPE: DNA
<213> ORGANISM: Artificial Sequence
<220> FEATURE:
<223> OTHER INFORMATION: Synthetic

<400> SEQUENCE: 139

```
cagaatatta acacctgg                                                    18
```

<210> SEQ ID NO 140
<211> LENGTH: 6
<212> TYPE: PRT
<213> ORGANISM: Artificial Sequence
<220> FEATURE:
<223> OTHER INFORMATION: Synthetic

<400> SEQUENCE: 140

Gln Asn Ile Asn Thr Trp
1               5

<210> SEQ ID NO 141

<211> LENGTH: 9
<212> TYPE: DNA
<213> ORGANISM: Artificial Sequence
<220> FEATURE:
<223> OTHER INFORMATION: Synthetic

<400> SEQUENCE: 141 gctgcatcc                                                                        9

<210> SEQ ID NO 142
<211> LENGTH: 3
<212> TYPE: PRT
<213> ORGANISM: Artificial Sequence
<220> FEATURE:
<223> OTHER INFORMATION: Synthetic

<400> SEQUENCE: 142

Ala Ala Ser
 1

<210> SEQ ID NO 143
<211> LENGTH: 27
<212> TYPE: DNA
<213> ORGANISM: Artificial Sequence
<220> FEATURE:
<223> OTHER INFORMATION: Synthetic

<400> SEQUENCE: 143
caacaggcta acagtttccc tctcact                                                   27

<210> SEQ ID NO 144
<211> LENGTH: 9
<212> TYPE: PRT
<213> ORGANISM: Artificial Sequence
<220> FEATURE:
<223> OTHER INFORMATION: Synthetic

<400> SEQUENCE: 144

Gln Gln Ala Asn Ser Phe Pro Leu Thr
 1               5

<210> SEQ ID NO 145
<211> LENGTH: 324
<212> TYPE: DNA
<213> ORGANISM: Artificial Sequence
<220> FEATURE:
<223> OTHER INFORMATION: Synthetic

<400> SEQUENCE: 145
gaaattgtat tgacacagtc tccagccacc ctgtctttgt ctccagggga aagagccacc      60
ctctcctgca gggccagtca gagtgttagc aactacttag cctggtacca acagaaacct     120
ggccaggctc ccaggctcct catctatgat gcatccaaca gggccactgg catcccagcc     180
aggttcagtg gcagtgggtc tgggacagac ttcactctca ccatcagcag ccttgaacct     240
gaagattttg ctgtttatta ctgtcagcag cgtgacgact ggcctccgta cacttttggc     300
caggggacca ggctggagat caaa                                           324

<210> SEQ ID NO 146
<211> LENGTH: 108
<212> TYPE: PRT
<213> ORGANISM: Artificial Sequence
<220> FEATURE:
<223> OTHER INFORMATION: Synthetic

<400> SEQUENCE: 146

```
Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Asn Tyr
                20                  25                  30

Leu Ala Trp Tyr Gln Gln Lys Pro Gly Gln Ala Pro Arg Leu Leu Ile
            35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Asp Asp Trp Pro Pro
                85                  90                  95

Tyr Thr Phe Gly Gln Gly Thr Arg Leu Glu Ile Lys
            100                 105
```

<210> SEQ ID NO 147
<211> LENGTH: 18
<212> TYPE: DNA
<213> ORGANISM: Artificial Sequence
<220> FEATURE:
<223> OTHER INFORMATION: Synthetic

<400> SEQUENCE: 147
cagagtgtta gcaactac                                                     18

<210> SEQ ID NO 148
<211> LENGTH: 6
<212> TYPE: PRT
<213> ORGANISM: Artificial Sequence
<220> FEATURE:
<223> OTHER INFORMATION: Synthetic

<400> SEQUENCE: 148

```
Gln Ser Val Ser Asn Tyr
1               5
```

<210> SEQ ID NO 149
<211> LENGTH: 9
<212> TYPE: DNA
<213> ORGANISM: Artificial Sequence
<220> FEATURE:
<223> OTHER INFORMATION: Synthetic

<400> SEQUENCE: 149 gatgcatcc                                                                9

<210> SEQ ID NO 150
<211> LENGTH: 3
<212> TYPE: PRT
<213> ORGANISM: Artificial Sequence
<220> FEATURE:
<223> OTHER INFORMATION: Synthetic

<400> SEQUENCE: 150

```
Asp Ala Ser
1
```

<210> SEQ ID NO 151
<211> LENGTH: 30
<212> TYPE: DNA
<213> ORGANISM: Artificial Sequence
<220> FEATURE:
<223> OTHER INFORMATION: Synthetic

<400> SEQUENCE: 151
cagcagcgtg acgactggcc tccgtacact                                     30

<210> SEQ ID NO 152
<211> LENGTH: 10
<212> TYPE: PRT
<213> ORGANISM: Artificial Sequence
<220> FEATURE:
<223> OTHER INFORMATION: Synthetic

<400> SEQUENCE: 152

Gln Gln Arg Asp Asp Trp Pro Pro Tyr Thr
 1               5                  10

<210> SEQ ID NO 153
<211> LENGTH: 324
<212> TYPE: DNA
<213> ORGANISM: Artificial Sequence
<220> FEATURE:
<223> OTHER INFORMATION: Synthetic

<400> SEQUENCE: 153
gaaatagtga tgacgcagtc tccagccacc ctgtctgtgt ctccagggga aagagtcacc      60
ctctcctgca gggccagtca gagtgttagt agtaacttag cctggtacca gcagaaacct     120
ggccaggctc cccggctcct catctatggt tcatccacca gggccactgg tatcccagcc     180
aggttcagtg gcagtgggtc tgggacagaa ttcactctca ccatcagcag cctgcagtct     240
gaggattttg cagtttatta ctgtcagcag tatgatgact ggcctccgct cactttcggc     300
ggagggacca aggtggatat caaa                                           324

<210> SEQ ID NO 154
<211> LENGTH: 108
<212> TYPE: PRT
<213> ORGANISM: Artificial Sequence
<220> FEATURE:
<223> OTHER INFORMATION: Synthetic

<400> SEQUENCE: 154

Glu Ile Val Met Thr Gln Ser Pro Ala Thr Leu Ser Val Ser Pro Gly
 1               5                  10                  15

Glu Arg Val Thr Leu Ser Cys Arg Ala Ser Gln Ser Val Ser Ser Asn
            20                  25                  30

Leu Ala Trp Tyr Gln Gln Lys Pro Gly Gln Ala Pro Arg Leu Leu Ile
        35                  40                  45

Tyr Gly Ser Ser Thr Arg Ala Thr Gly Ile Pro Ala Arg Phe Ser Gly
    50                  55                  60

Ser Gly Ser Gly Thr Glu Phe Thr Leu Thr Ile Ser Ser Leu Gln Ser
65                  70                  75                  80

Glu Asp Phe Ala Val Tyr Tyr Cys Gln Gln Tyr Asp Asp Trp Pro Pro
                85                  90                  95

Leu Thr Phe Gly Gly Gly Thr Lys Val Asp Ile Lys
            100                 105

<210> SEQ ID NO 155
<211> LENGTH: 18
<212> TYPE: DNA
<213> ORGANISM: Artificial Sequence
<220> FEATURE:
<223> OTHER INFORMATION: Synthetic

```
<400> SEQUENCE: 155
cagagtgtta gtagtaac                                                    18

<210> SEQ ID NO 156
<211> LENGTH: 6
<212> TYPE: PRT
<213> ORGANISM: Artificial Sequence
<220> FEATURE:
<223> OTHER INFORMATION: Synthetic

<400> SEQUENCE: 156

Gln Ser Val Ser Ser Asn
 1               5

<210> SEQ ID NO 157
<211> LENGTH: 9
<212> TYPE: DNA
<213> ORGANISM: Artificial Sequence
<220> FEATURE:
<223> OTHER INFORMATION: Synthetic

<400> SEQUENCE: 157 ggttcatcc                                                               9

<210> SEQ ID NO 158
<211> LENGTH: 3
<212> TYPE: PRT
<213> ORGANISM: Artificial Sequence
<220> FEATURE:
<223> OTHER INFORMATION: Synthetic

<400> SEQUENCE: 158

Gly Ser Ser
 1

<210> SEQ ID NO 159
<211> LENGTH: 30
<212> TYPE: DNA
<213> ORGANISM: Artificial Sequence
<220> FEATURE:
<223> OTHER INFORMATION: Synthetic

<400> SEQUENCE: 159
cagcagtatg atgactggcc tccgctcact                                        30

<210> SEQ ID NO 160
<211> LENGTH: 10
<212> TYPE: PRT
<213> ORGANISM: Artificial Sequence
<220> FEATURE:
<223> OTHER INFORMATION: Synthetic

<400> SEQUENCE: 160

Gln Gln Tyr Asp Asp Trp Pro Pro Leu Thr
 1               5                  10

<210> SEQ ID NO 161
<211> LENGTH: 363
<212> TYPE: DNA
<213> ORGANISM: Artificial Sequence
<220> FEATURE:
<223> OTHER INFORMATION: Synthetic

<400> SEQUENCE: 161
caggtgcgac tggtggagtc tgagctgag gtgaagaagc ctggggcctc agtgaaggtc       60
```

```
tcctgcaaga cttctggtta cacctttgcc ggctatggta tcacttgggt gcgacaggcc    120
cctggacgag gacttgagtg gatgggatgg gtcagcgctt acaatggtga cacagactat    180
gcacagagcc tccagggcag agtcaccatg accacagaca catccacgag cacagcctac    240
atggagctga ggagcctgag atctgacgac acggccatgt attactgtgc gagagatcgg    300
tatagcagct cgtcgggcta ctttgactac tggggccagg gaaccctggt caccgtctcc    360
tca                                                                  363
```

<210> SEQ ID NO 162
<211> LENGTH: 121
<212> TYPE: PRT
<213> ORGANISM: Artificial Sequence
<220> FEATURE:
<223> OTHER INFORMATION: Synthetic

<400> SEQUENCE: 162

```
Gln Val Arg Leu Val Glu Ser Gly Ala Glu Val Lys Lys Pro Gly Ala
 1               5                  10                  15

Ser Val Lys Val Ser Cys Lys Thr Ser Gly Tyr Thr Phe Ala Gly Tyr
            20                  25                  30

Gly Ile Thr Trp Val Arg Gln Ala Pro Gly Arg Gly Leu Glu Trp Met
        35                  40                  45

Gly Trp Val Ser Ala Tyr Asn Gly Asp Thr Asp Tyr Ala Gln Ser Leu
    50                  55                  60

Gln Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Met Tyr Tyr Cys
                85                  90                  95

Ala Arg Asp Arg Tyr Ser Ser Ser Gly Tyr Phe Asp Tyr Trp Gly
            100                 105                 110

Gln Gly Thr Leu Val Thr Val Ser Ser
        115                 120
```

<210> SEQ ID NO 163
<211> LENGTH: 24
<212> TYPE: DNA
<213> ORGANISM: Artificial Sequence
<220> FEATURE:
<223> OTHER INFORMATION: Synthetic

<400> SEQUENCE: 163

```
ggttacacct tgccggcta tggt                                            24
```

<210> SEQ ID NO 164
<211> LENGTH: 8
<212> TYPE: PRT
<213> ORGANISM: Artificial Sequence
<220> FEATURE:
<223> OTHER INFORMATION: Synthetic

<400> SEQUENCE: 164

```
Gly Tyr Thr Phe Ala Gly Tyr Gly
 1               5
```

<210> SEQ ID NO 165
<211> LENGTH: 24
<212> TYPE: DNA
<213> ORGANISM: Artificial Sequence
<220> FEATURE:
<223> OTHER INFORMATION: Synthetic

<400> SEQUENCE: 165
gtcagcgctt acaatggtga caca                                        24

<210> SEQ ID NO 166
<211> LENGTH: 8
<212> TYPE: PRT
<213> ORGANISM: Artificial Sequence
<220> FEATURE:
<223> OTHER INFORMATION: Synthetic

<400> SEQUENCE: 166

Val Ser Ala Tyr Asn Gly Asp Thr
1               5

<210> SEQ ID NO 167
<211> LENGTH: 42
<212> TYPE: DNA
<213> ORGANISM: Artificial Sequence
<220> FEATURE:
<223> OTHER INFORMATION: Synthetic

<400> SEQUENCE: 167
gcgagagatc ggtatagcag ctcgtcgggc tactttgact ac                    42

<210> SEQ ID NO 168
<211> LENGTH: 14
<212> TYPE: PRT
<213> ORGANISM: Artificial Sequence
<220> FEATURE:
<223> OTHER INFORMATION: Synthetic

<400> SEQUENCE: 168

Ala Arg Asp Arg Tyr Ser Ser Ser Ser Gly Tyr Phe Asp Tyr
1               5                   10

<210> SEQ ID NO 169
<211> LENGTH: 324
<212> TYPE: DNA
<213> ORGANISM: Artificial Sequence
<220> FEATURE:
<223> OTHER INFORMATION: Synthetic

<400> SEQUENCE: 169
gacatcgtga tgacccagtc tccatcttcc gtgtctgcat ctgtaggaga cagagtcacc    60
atcacttgtc gggcgagtca gggtattagc agctggttag cctggcatca gcagaaacca   120
gggaaagccc ctaaggtcct gatctatgcg gcatccagtt tgcatagtgg ggtcccctca   180
aggttcagcg gcagtggatc tgggacagaa ttcactctca ccatcagcag cctgcagcct   240
gaagattttg caacttacta ttgtcaacag gctaacactt tcccgtacac ttttggccag   300
gggaccaagg tggagatcaa acga                                          324

<210> SEQ ID NO 170
<211> LENGTH: 108
<212> TYPE: PRT
<213> ORGANISM: Artificial Sequence
<220> FEATURE:
<223> OTHER INFORMATION: Synthetic

<400> SEQUENCE: 170

Asp Ile Val Met Thr Gln Ser Pro Ser Val Ser Ala Ser Val Gly
1               5                   10                  15

Asp Arg Val Thr Ile Thr Cys Arg Ala Ser Gln Gly Ile Ser Ser Trp
            20                  25                  30

Leu Ala Trp His Gln Gln Lys Pro Gly Lys Ala Pro Lys Val Leu Ile
            35                  40                  45

Tyr Ala Ala Ser Ser Leu His Ser Gly Val Pro Ser Arg Phe Ser Gly
        50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Gln Gln Ala Asn Thr Phe Pro Tyr
                85                  90                  95

Thr Phe Gly Gln Gly Thr Lys Val Glu Ile Lys Arg
            100                 105

<210> SEQ ID NO 171
<211> LENGTH: 18
<212> TYPE: DNA
<213> ORGANISM: Artificial Sequence
<220> FEATURE:
<223> OTHER INFORMATION: Synthetic

<400> SEQUENCE: 171
cagggtatta gcagctgg                                              18

<210> SEQ ID NO 172
<211> LENGTH: 6
<212> TYPE: PRT
<213> ORGANISM: Artificial Sequence
<220> FEATURE:
<223> OTHER INFORMATION: Synthetic

<400> SEQUENCE: 172

Gln Gly Ile Ser Ser Trp
 1               5

<210> SEQ ID NO 173
<211> LENGTH: 9
<212> TYPE: DNA
<213> ORGANISM: Artificial Sequence
<220> FEATURE:
<223> OTHER INFORMATION: Synthetic

<400> SEQUENCE: 173 gcggcatcc                                                         9

<210> SEQ ID NO 174
<211> LENGTH: 3
<212> TYPE: PRT
<213> ORGANISM: Artificial Sequence
<220> FEATURE:
<223> OTHER INFORMATION: Synthetic

<400> SEQUENCE: 174

Ala Ala Ser
 1

<210> SEQ ID NO 175
<211> LENGTH: 27
<212> TYPE: DNA
<213> ORGANISM: Artificial Sequence
<220> FEATURE:
<223> OTHER INFORMATION: Synthetic

<400> SEQUENCE: 175
caacaggcta acactttccc gtacact                                    27

<210> SEQ ID NO 176
<211> LENGTH: 9
<212> TYPE: PRT
<213> ORGANISM: Artificial Sequence
<220> FEATURE:
<223> OTHER INFORMATION: Synthetic

<400> SEQUENCE: 176

Gln Gln Ala Asn Thr Phe Pro Tyr Thr
1               5

<210> SEQ ID NO 177
<211> LENGTH: 363
<212> TYPE: DNA
<213> ORGANISM: Artificial Sequence
<220> FEATURE:
<223> OTHER INFORMATION: Synthetic

<400> SEQUENCE: 177
caggtgcagc tggtacagtc tggagctgag gtgaagaagc ctggggcctc agtgaaggtc      60
tcctgcaaga cttctggtta cacctttgcc ggctatggta tcacttgggt gcgacaggcc     120
cctggacgag gacttgagtg gatgggatgg tcagcgctt acaatggtga cacagactat     180
gcacagagcc tccagggcag agtcaccatg accacagaca catccacgag cacagcctac     240
atggagctga ggagcctgag atctgacgac acggccatgt attactgtgc gagagatcgg     300
tatagcagct cgtcgggcta ctttgactac tggggccagg gaaccctggt caccgtctcc     360
tca                                                                    363

<210> SEQ ID NO 178
<211> LENGTH: 121
<212> TYPE: PRT
<213> ORGANISM: Artificial Sequence
<220> FEATURE:
<223> OTHER INFORMATION: Synthetic

<400> SEQUENCE: 178

Gln Val Gln Leu Val Gln Ser Gly Ala Glu Val Lys Lys Pro Gly Ala
1               5                   10                  15

Ser Val Lys Val Ser Cys Lys Thr Ser Gly Tyr Thr Phe Ala Gly Tyr
            20                  25                  30

Gly Ile Thr Trp Val Arg Gln Ala Pro Gly Arg Gly Leu Glu Trp Met
        35                  40                  45

Gly Trp Ser Ala Tyr Asn Gly Asp Thr Asp Tyr Ala Gln Ser Leu
    50                  55                  60

Gln Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Met Tyr Tyr Cys
                85                  90                  95

Ala Arg Asp Arg Tyr Ser Ser Ser Gly Tyr Phe Asp Tyr Trp Gly
            100                 105                 110

Gln Gly Thr Leu Val Thr Val Ser Ser
        115                 120

<210> SEQ ID NO 179
<211> LENGTH: 321
<212> TYPE: DNA
<213> ORGANISM: Artificial Sequence
<220> FEATURE:
<223> OTHER INFORMATION: Synthetic

<400> SEQUENCE: 179

```
gacatccaga tgacccagtc tccatcttcc gtgtctgcat ctgtaggaga cagagtcacc    60
atcacttgtc gggcgagtca gggtattagc agctggttag cctggcatca gcagaaacca   120
gggaaagccc ctaaggtcct gatctatgcg gcatccagtt tgcatagtgg ggtcccctca   180
aggttcagcg gcagtggatc tgggacagaa ttcactctca ccatcagcag cctgcagcct   240
gaagattttg caacttacta ttgtcaacag gctaacactt tcccgtacac ttttggccag   300
gggaccaagc tggagatcaa a                                             321
```

<210> SEQ ID NO 180
<211> LENGTH: 107
<212> TYPE: PRT
<213> ORGANISM: Artificial Sequence
<220> FEATURE:
<223> OTHER INFORMATION: Synthetic

<400> SEQUENCE: 180

```
Asp Ile Gln Met Thr Gln Ser Pro Ser Ser Val Ser Ala Ser Val Gly
 1               5                  10                  15

Asp Arg Val Thr Ile Thr Cys Arg Ala Ser Gln Gly Ile Ser Ser Trp
            20                  25                  30

Leu Ala Trp His Gln Lys Pro Gly Lys Ala Pro Lys Val Leu Ile
        35                  40                  45

Tyr Ala Ala Ser Ser Leu His Ser Gly Val Pro Ser Arg Phe Ser Gly
50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Gln Gln Ala Asn Thr Phe Pro Tyr
                85                  90                  95

Thr Phe Gly Gln Gly Thr Lys Leu Glu Ile Lys
            100                 105
```

<210> SEQ ID NO 181
<211> LENGTH: 324
<212> TYPE: DNA
<213> ORGANISM: Artificial Sequence
<220> FEATURE:
<223> OTHER INFORMATION: Synthetic

<400> SEQUENCE: 181

```
gccatccagt tgacccagtc tccatcttcc gtgtctgcat ctgtaggaga cagagtcacc    60
atcacttgtc gggcgagtca gggtattagc agctggttag cctggtatca gcagaaacca   120
gggaaagccc ctaagctcct gatgtttggt gcatccagtt tgcaaagtgg ggtcccatca   180
aggttcagcg gcagtggatc tgggacagat ttcattctca ccatcagcag cctgcagcct   240
gaagattttg caacttacta ttgtcaacag gctaacagtt tcccgtactc ttttggccag   300
gggaccaagg tggaaatcaa acga                                          324
```

<210> SEQ ID NO 182
<211> LENGTH: 108
<212> TYPE: PRT
<213> ORGANISM: Artificial Sequence
<220> FEATURE:
<223> OTHER INFORMATION: Synthetic

<400> SEQUENCE: 182

```
Ala Ile Gln Leu Thr Gln Ser Pro Ser Ser Val Ser Ala Ser Val Gly
 1               5                  10                  15
```

Asp Arg Val Thr Ile Thr Cys Arg Ala Ser Gln Gly Ile Ser Ser Trp
            20                  25                  30

Leu Ala Trp Tyr Gln Gln Lys Pro Gly Lys Ala Pro Lys Leu Leu Met
        35                  40                  45

Phe Gly Ala Ser Ser Leu Gln Ser Gly Val Pro Ser Arg Phe Ser Gly
    50                  55                  60

Ser Gly Ser Gly Thr Asp Phe Ile Leu Thr Ile Ser Ser Leu Gln Pro
65                  70                  75                  80

Glu Asp Phe Ala Thr Tyr Tyr Cys Gln Gln Ala Asn Ser Phe Pro Tyr
                85                  90                  95

Ser Phe Gly Gln Gly Thr Lys Val Glu Ile Lys Arg
            100                 105

<210> SEQ ID NO 183
<211> LENGTH: 18
<212> TYPE: DNA
<213> ORGANISM: Artificial Sequence
<220> FEATURE:
<223> OTHER INFORMATION: Synthetic

<400> SEQUENCE: 183
cagggtatta gcagctgg                                                       18

<210> SEQ ID NO 184
<211> LENGTH: 6
<212> TYPE: PRT
<213> ORGANISM: Artificial Sequence
<220> FEATURE:
<223> OTHER INFORMATION: Synthetic

<400> SEQUENCE: 184

Gln Gly Ile Ser Ser Trp
 1               5

<210> SEQ ID NO 185
<211> LENGTH: 9
<212> TYPE: DNA
<213> ORGANISM: Artificial Sequence
<220> FEATURE:
<223> OTHER INFORMATION: Synthetic

<400> SEQUENCE: 185 ggtgcatcc                                                                  9

<210> SEQ ID NO 186
<211> LENGTH: 3
<212> TYPE: PRT
<213> ORGANISM: Artificial Sequence
<220> FEATURE:
<223> OTHER INFORMATION: Synthetic

<400> SEQUENCE: 186

Gly Ala Ser
 1

<210> SEQ ID NO 187
<211> LENGTH: 27
<212> TYPE: DNA
<213> ORGANISM: Artificial Sequence
<220> FEATURE:
<223> OTHER INFORMATION: Synthetic

<400> SEQUENCE: 187
caacaggcta acagtttccc gtactct                                             27

<210> SEQ ID NO 188
<211> LENGTH: 9
<212> TYPE: PRT
<213> ORGANISM: Artificial Sequence
<220> FEATURE:
<223> OTHER INFORMATION: Synthetic

<400> SEQUENCE: 188

Gln Gln Ala Asn Ser Phe Pro Tyr Ser
 1               5

<210> SEQ ID NO 189
<211> LENGTH: 321
<212> TYPE: DNA
<213> ORGANISM: Artificial Sequence
<220> FEATURE:
<223> OTHER INFORMATION: Synthetic

<400> SEQUENCE: 189
gacatccaga tgacccagtc tccatcttcc gtgtctgcat ctgtaggaga cagagtcacc      60
atcacttgtc gggcgagtca gggtattagc agctggttag cctggtatca gcagaaacca     120
gggaaagccc ctaagctcct gatgtttggt gcatccagtt tgcaaagtgg ggtcccatca     180
aggttcagcg gcagtggatc tgggacagat ttcattctca ccatcagcag cctgcagcct     240
gaagattttg caacttacta ttgtcaacag gctaacagtt tcccgtactc ttttggccag     300
gggaccaagc tggagatcaa a                                              321

<210> SEQ ID NO 190
<211> LENGTH: 107
<212> TYPE: PRT
<213> ORGANISM: Artificial Sequence
<220> FEATURE:
<223> OTHER INFORMATION: Synthetic

<400> SEQUENCE: 190

Asp Ile Gln Met Thr Gln Ser Pro Ser Ser Val Ser Ala Ser Val Gly
 1               5                  10                  15

Asp Arg Val Thr Ile Thr Cys Arg Ala Ser Gln Gly Ile Ser Ser Trp
             20                  25                  30

Leu Ala Trp Tyr Gln Gln Lys Pro Gly Lys Ala Pro Lys Leu Leu Met
         35                  40                  45

Phe Gly Ala Ser Ser Leu Gln Ser Gly Val Pro Ser Arg Phe Ser Gly
     50                  55                  60

Ser Gly Ser Gly Thr Asp Phe Ile Leu Thr Ile Ser Ser Leu Gln Pro
 65                  70                  75                  80

Glu Asp Phe Ala Thr Tyr Tyr Cys Gln Gln Ala Asn Ser Phe Pro Tyr
                 85                  90                  95

Ser Phe Gly Gln Gly Thr Lys Leu Glu Ile Lys
            100                 105

<210> SEQ ID NO 191
<211> LENGTH: 363
<212> TYPE: DNA
<213> ORGANISM: Artificial Sequence
<220> FEATURE:
<223> OTHER INFORMATION: Synthetic

<400> SEQUENCE: 191
gaggtgcagc tgttggagtc tggagctgag gtgaagaagc ctggggccgc agtgaaggtc      60

```
tcctgcaagg cttctggtta cacctttacc gcctatggta tcagctgggt gcgacaggcc    120
cctggacaag ggctagagtg gatgggatgg atcagcgctt acgatggtga cacaaacaat    180
gcacagaagt tccagggcag agtcaccatg accacagaca catcctcgag cacagcctac    240
atggagctga ggagcctggg atctgacgac acggccgtgt attactgtgc gagagatcgc    300
tatagcagct cctcgggcta ctttgactac tggggccagg aacccctggt caccgtctcc    360
tca                                                                   363
```

<210> SEQ ID NO 192
<211> LENGTH: 121
<212> TYPE: PRT
<213> ORGANISM: Artificial Sequence
<220> FEATURE:
<223> OTHER INFORMATION: Synthetic

<400> SEQUENCE: 192

```
Glu Val Gln Leu Val Glu Ser Gly Ala Glu Val Lys Lys Pro Gly Ala
 1               5                  10                  15

Ala Val Lys Val Ser Cys Lys Ala Ser Gly Tyr Thr Phe Thr Ala Tyr
            20                  25                  30

Gly Ile Ser Trp Val Arg Gln Ala Pro Gly Gln Gly Leu Glu Trp Met
        35                  40                  45

Gly Trp Ile Ser Ala Tyr Asp Gly Asp Thr Asn Asn Ala Gln Lys Phe
    50                  55                  60

Gln Gly Arg Val Thr Met Thr Thr Asp Thr Ser Ser Ser Thr Ala Tyr
65                  70                  75                  80

Met Glu Leu Arg Ser Leu Gly Ser Asp Asp Thr Ala Val Tyr Tyr Cys
                85                  90                  95

Ala Arg Asp Arg Tyr Ser Ser Ser Gly Tyr Phe Asp Tyr Trp Gly
            100                 105                 110

Gln Gly Thr Leu Val Thr Val Ser Ser
        115                 120
```

<210> SEQ ID NO 193
<211> LENGTH: 24
<212> TYPE: DNA
<213> ORGANISM: Artificial Sequence
<220> FEATURE:
<223> OTHER INFORMATION: Synthetic

<400> SEQUENCE: 193

```
ggttacacct ttaccgccta tggt                                            24
```

<210> SEQ ID NO 194
<211> LENGTH: 8
<212> TYPE: PRT
<213> ORGANISM: Artificial Sequence
<220> FEATURE:
<223> OTHER INFORMATION: Synthetic

<400> SEQUENCE: 194

```
Gly Tyr Thr Phe Thr Ala Tyr Gly
 1               5
```

<210> SEQ ID NO 195
<211> LENGTH: 24
<212> TYPE: DNA
<213> ORGANISM: Artificial Sequence
<220> FEATURE:
<223> OTHER INFORMATION: Synthetic

<400> SEQUENCE: 195
atcagcgctt acgatggtga caca                                                24

<210> SEQ ID NO 196
<211> LENGTH: 8
<212> TYPE: PRT
<213> ORGANISM: Artificial Sequence
<220> FEATURE:
<223> OTHER INFORMATION: Synthetic

<400> SEQUENCE: 196

Ile Ser Ala Tyr Asp Gly Asp Thr
1               5

<210> SEQ ID NO 197
<211> LENGTH: 42
<212> TYPE: DNA
<213> ORGANISM: Artificial Sequence
<220> FEATURE:
<223> OTHER INFORMATION: Synthetic

<400> SEQUENCE: 197
gcgagagatc gctatagcag ctcctcgggc tactttgact ac                            42

<210> SEQ ID NO 198
<211> LENGTH: 14
<212> TYPE: PRT
<213> ORGANISM: Artificial Sequence
<220> FEATURE:
<223> OTHER INFORMATION: Synthetic

<400> SEQUENCE: 198

Ala Arg Asp Arg Tyr Ser Ser Ser Ser Gly Tyr Phe Asp Tyr
1               5                   10

<210> SEQ ID NO 199
<211> LENGTH: 324
<212> TYPE: DNA
<213> ORGANISM: Artificial Sequence
<220> FEATURE:
<223> OTHER INFORMATION: Synthetic

<400> SEQUENCE: 199
gacatcgtga tgacccagtc tccatcttcc gtgtctgcat ctgtaggaga cagagtcacc         60
atcacttgtc gggcgagtca ggatattagc agctggttag cctggtctca gcagaagcca        120
gggaaagccc ctaaggccct gatctatgct gcatccagtt tgcaaagtgg ggtcccatca        180
aggttcagcg gcagtggatc tgggacagat ttcactctca ccatcagcag cctgcagcct        240
gaagattttg caacttacta ttgtcaacag gctaacagtt tcccgtacac ttttggccag        300
gggaccaagg tggagatcaa acga                                              324

<210> SEQ ID NO 200
<211> LENGTH: 108
<212> TYPE: PRT
<213> ORGANISM: Artificial Sequence
<220> FEATURE:
<223> OTHER INFORMATION: Synthetic

<400> SEQUENCE: 200

Asp Ile Val Met Thr Gln Ser Pro Ser Val Ser Ala Ser Val Gly
1               5                   10                  15

Asp Arg Val Thr Ile Thr Cys Arg Ala Ser Gln Asp Ile Ser Ser Trp
                20                  25                  30

Leu Ala Trp Ser Gln Gln Lys Pro Gly Lys Ala Pro Lys Ala Leu Ile
         35                  40                  45

Tyr Ala Ala Ser Ser Leu Gln Ser Gly Val Pro Ser Arg Phe Ser Gly
     50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Ala Asn Ser Phe Pro Tyr
                 85                  90                  95

Thr Phe Gly Gln Gly Thr Lys Val Glu Ile Lys Arg
             100                 105

<210> SEQ ID NO 201
<211> LENGTH: 18
<212> TYPE: DNA
<213> ORGANISM: Artificial Sequence
<220> FEATURE:
<223> OTHER INFORMATION: Synthetic

<400> SEQUENCE: 201
caggatatta gcagctgg                                             18

<210> SEQ ID NO 202
<211> LENGTH: 6
<212> TYPE: PRT
<213> ORGANISM: Artificial Sequence
<220> FEATURE:
<223> OTHER INFORMATION: Synthetic

<400> SEQUENCE: 202

Gln Asp Ile Ser Ser Trp
 1               5

<210> SEQ ID NO 203
<211> LENGTH: 9
<212> TYPE: DNA
<213> ORGANISM: Artificial Sequence
<220> FEATURE:
<223> OTHER INFORMATION: Synthetic

<400> SEQUENCE: 203 gctgcatcc                                                        9

<210> SEQ ID NO 204
<211> LENGTH: 3
<212> TYPE: PRT
<213> ORGANISM: Artificial Sequence
<220> FEATURE:
<223> OTHER INFORMATION: Synthetic

<400> SEQUENCE: 204

Ala Ala Ser
 1

<210> SEQ ID NO 205
<211> LENGTH: 27
<212> TYPE: DNA
<213> ORGANISM: Artificial Sequence
<220> FEATURE:
<223> OTHER INFORMATION: Synthetic

<400> SEQUENCE: 205
caacaggcta acagtttccc gtacact                                   27

```
<210> SEQ ID NO 206
<211> LENGTH: 9
<212> TYPE: PRT
<213> ORGANISM: Artificial Sequence
<220> FEATURE:
<223> OTHER INFORMATION: Synthetic

<400> SEQUENCE: 206

Gln Gln Ala Asn Ser Phe Pro Tyr Thr
 1               5

<210> SEQ ID NO 207
<211> LENGTH: 363
<212> TYPE: DNA
<213> ORGANISM: Artificial Sequence
<220> FEATURE:
<223> OTHER INFORMATION: Synthetic

<400> SEQUENCE: 207
caggtgcagc tggtacagtc tggagctgag gtgaagaagc ctggggccgc agtgaaggtc      60
tcctgcaagg cttctggtta cacctttacc gcctatggta tcagctgggt gcgacaggcc     120
cctggacaag gctagagtg gatgggatgg atcagcgctt acgatggtga cacaaacaat      180
gcacagaagt tccagggcag agtcaccatg accacagaca catcctcgag cacagcctac     240
atggagctga ggagcctggg atctgacgac acggccgtgt attactgtgc gagagatcgc     300
tatagcagct cctcgggcta ctttgactac tggggccagg gaaccctggt cactgtctcc     360
tca                                                                   363

<210> SEQ ID NO 208
<211> LENGTH: 121
<212> TYPE: PRT
<213> ORGANISM: Artificial Sequence
<220> FEATURE:
<223> OTHER INFORMATION: Synthetic

<400> SEQUENCE: 208

Gln Val Gln Leu Val Gln Ser Gly Ala Glu Val Lys Lys Pro Gly Ala
 1               5                  10                  15

Ala Val Lys Val Ser Cys Lys Ala Ser Gly Tyr Thr Phe Thr Ala Tyr
            20                  25                  30

Gly Ile Ser Trp Val Arg Gln Ala Pro Gly Gln Gly Leu Glu Trp Met
        35                  40                  45

Gly Trp Ile Ser Ala Tyr Asp Gly Asp Thr Asn Asn Ala Gln Lys Phe
    50                  55                  60

Gln Gly Arg Val Thr Met Thr Thr Asp Thr Ser Ser Ser Thr Ala Tyr
65                  70                  75                  80

Met Glu Leu Arg Ser Leu Gly Ser Asp Asp Thr Ala Val Tyr Tyr Cys
                85                  90                  95

Ala Arg Asp Arg Tyr Ser Ser Ser Ser Gly Tyr Phe Asp Tyr Trp Gly
            100                 105                 110

Gln Gly Thr Leu Val Thr Val Ser Ser
        115                 120

<210> SEQ ID NO 209
<211> LENGTH: 321
<212> TYPE: DNA
<213> ORGANISM: Artificial Sequence
<220> FEATURE:
<223> OTHER INFORMATION: Synthetic

<400> SEQUENCE: 209
```

```
gacatccaga tgacccagtc tccatcttcc gtgtctgcat ctgtaggaga cagagtcacc    60
atcacttgtc gggcgagtca ggatattagc agctggttag cctggtctca gcagaagcca   120
gggaaagccc ctaaggccct gatctatgct gcatccagtt tgcaaagtgg ggtcccatca   180
aggttcagcg gcagtggatc tgggacagat ttcactctca ccatcagcag cctgcagcct   240
gaagattttg caacttacta ttgtcaacag gctaacagtt ccccgtacac ttttggccag   300
gggaccaagc tggagatcaa a                                             321
```

<210> SEQ ID NO 210
<211> LENGTH: 107
<212> TYPE: PRT
<213> ORGANISM: Artificial Sequence
<220> FEATURE:
<223> OTHER INFORMATION: Synthetic

<400> SEQUENCE: 210

```
Asp Ile Gln Met Thr Gln Ser Pro Ser Ser Val Ser Ala Ser Val Gly
  1               5                  10                  15

Asp Arg Val Thr Ile Thr Cys Arg Ala Ser Gln Asp Ile Ser Ser Trp
             20                  25                  30

Leu Ala Trp Ser Gln Gln Lys Pro Gly Lys Ala Pro Lys Ala Leu Ile
         35                  40                  45

Tyr Ala Ala Ser Ser Leu Gln Ser Gly Val Pro Ser Arg Phe Ser Gly
     50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Ala Asn Ser Phe Pro Tyr
                 85                  90                  95

Thr Phe Gly Gln Gly Thr Lys Leu Glu Ile Lys
            100                 105
```

<210> SEQ ID NO 211
<211> LENGTH: 360
<212> TYPE: DNA
<213> ORGANISM: Artificial Sequence
<220> FEATURE:
<223> OTHER INFORMATION: Synthetic

<400> SEQUENCE: 211

```
caggtgcgac tggtggagtc tgggactgag gtgaagaagc ctggggcctc agtgaaggtc    60
tcctgcaagg tttccggata caccctcatt gacttatcca tacactgggt gcgacaggct   120
cctggagaag gccttgagtg gatgggggt tttgatcctg aagaaagtga acaatctat     180 gcacagaaat tccagggcag agtcaccatg accgaggaca catctacaga cacagcctac   240
atggagctaa gcagcctgag atctgaggac acggccgtct attactgtgt gacagagccg   300 attttttggaa tccttatcca tgagtcctgg ggccagggaa ccctggtcac tgtctcctca   360
```

<210> SEQ ID NO 212
<211> LENGTH: 120
<212> TYPE: PRT
<213> ORGANISM: Artificial Sequence
<220> FEATURE:
<223> OTHER INFORMATION: Synthetic

<400> SEQUENCE: 212

```
Gln Val Arg Leu Val Glu Ser Gly Thr Glu Val Lys Lys Pro Gly Ala
  1               5                  10                  15
```

-continued

```
Ser Val Lys Val Ser Cys Lys Val Ser Gly Tyr Thr Leu Ile Asp Leu
             20                  25                  30

Ser Ile His Trp Val Arg Gln Ala Pro Gly Glu Gly Leu Glu Trp Met
         35                  40                  45

Gly Gly Phe Asp Pro Glu Glu Ser Glu Thr Ile Tyr Ala Gln Lys Phe
     50                  55                  60

Gln Gly Arg Val Thr Met Thr Glu Asp Thr Ser Thr Asp Thr Ala Tyr
 65                  70                  75                  80

Met Glu Leu Ser Ser Leu Arg Ser Glu Asp Thr Ala Val Tyr Tyr Cys
                 85                  90                  95

Val Thr Glu Pro Ile Phe Gly Ile Leu Ile His Glu Ser Trp Gly Gln
            100                 105                 110

Gly Thr Leu Val Thr Val Ser Ser
        115                 120
```

<210> SEQ ID NO 213
<211> LENGTH: 24
<212> TYPE: DNA
<213> ORGANISM: Artificial Sequence
<220> FEATURE:
<223> OTHER INFORMATION: Synthetic

<400> SEQUENCE: 213
ggatacaccc tcattgactt atcc    24

<210> SEQ ID NO 214
<211> LENGTH: 8
<212> TYPE: PRT
<213> ORGANISM: Artificial Sequence
<220> FEATURE:
<223> OTHER INFORMATION: Synthetic

<400> SEQUENCE: 214

```
Gly Tyr Thr Leu Ile Asp Leu Ser
 1               5
```

<210> SEQ ID NO 215
<211> LENGTH: 24
<212> TYPE: DNA
<213> ORGANISM: Artificial Sequence
<220> FEATURE:
<223> OTHER INFORMATION: Synthetic

<400> SEQUENCE: 215
tttgatcctg aagaaagtga aaca    24

<210> SEQ ID NO 216
<211> LENGTH: 8
<212> TYPE: PRT
<213> ORGANISM: Artificial Sequence
<220> FEATURE:
<223> OTHER INFORMATION: Synthetic

<400> SEQUENCE: 216

```
Phe Asp Pro Glu Glu Ser Glu Thr
 1               5
```

<210> SEQ ID NO 217
<211> LENGTH: 39
<212> TYPE: DNA
<213> ORGANISM: Artificial Sequence
<220> FEATURE:
<223> OTHER INFORMATION: Synthetic

<400> SEQUENCE: 217
gtgacagagc cgattttgg aatccttatc catgagtcc                                39

<210> SEQ ID NO 218
<211> LENGTH: 13
<212> TYPE: PRT
<213> ORGANISM: Artificial Sequence
<220> FEATURE:
<223> OTHER INFORMATION: Synthetic

<400> SEQUENCE: 218

Val Thr Glu Pro Ile Phe Gly Ile Leu Ile His Glu Ser
 1               5                  10

<210> SEQ ID NO 219
<211> LENGTH: 339
<212> TYPE: DNA
<213> ORGANISM: Artificial Sequence
<220> FEATURE:
<223> OTHER INFORMATION: Synthetic

<400> SEQUENCE: 219
gaaattgtgc tgactcagac tccactctcc tcacctgtca cccttggaca gccggcctcc     60
atctcctgca ggtctagtca gccccgta cacagtaatg gacatacccta cttgagttgg    120 cttcagcaga ggccaggcca gcctccaaga atcctaattt ataagatttc tagacggttc    180
tctggggtcc cagacagatt cagtggcagt ggggcaggga cagatttcac gctgaagatc    240
agcagggtgg aaactgagga tgtcgggatt tattactgca tgcaagcttc acaatttccg    300
tggacgttcg gccaagggac caaagtggat atcaaacga                          339

<210> SEQ ID NO 220
<211> LENGTH: 113
<212> TYPE: PRT
<213> ORGANISM: Artificial Sequence
<220> FEATURE:
<223> OTHER INFORMATION: Synthetic

<400> SEQUENCE: 220

Glu Ile Val Leu Thr Gln Thr Pro Leu Ser Ser Pro Val Thr Leu Gly
 1               5                  10                  15

Gln Pro Ala Ser Ile Ser Cys Arg Ser Ser His Ser Pro Val His Ser
            20                  25                  30

Asn Gly His Thr Tyr Leu Ser Trp Leu Gln Gln Arg Pro Gly Gln Pro
        35                  40                  45

Pro Arg Ile Leu Ile Tyr Lys Ile Ser Arg Arg Phe Ser Gly Val Pro
    50                  55                  60

Asp Arg Phe Ser Gly Ser Gly Ala Gly Thr Asp Phe Thr Leu Lys Ile
65                  70                  75                  80

Ser Arg Val Glu Thr Glu Asp Val Gly Ile Tyr Tyr Cys Met Gln Ala
                85                  90                  95

Ser Gln Phe Pro Trp Thr Phe Gly Gln Gly Thr Lys Val Asp Ile Lys
            100                 105                 110

Arg

<210> SEQ ID NO 221
<211> LENGTH: 33
<212> TYPE: DNA
<213> ORGANISM: Artificial Sequence
<220> FEATURE:
<223> OTHER INFORMATION: Synthetic

```
<400> SEQUENCE: 221
cacagccccg tacacagtaa tggacatacc tac                                    33

<210> SEQ ID NO 222
<211> LENGTH: 11
<212> TYPE: PRT
<213> ORGANISM: Artificial Sequence
<220> FEATURE:
<223> OTHER INFORMATION: Synthetic

<400> SEQUENCE: 222

His Ser Pro Val His Ser Asn Gly His Thr Tyr
 1               5                  10

<210> SEQ ID NO 223
<211> LENGTH: 9
<212> TYPE: DNA
<213> ORGANISM: Artificial Sequence
<220> FEATURE:
<223> OTHER INFORMATION: Synthetic

<400> SEQUENCE: 223 aagatttct                                                                9

<210> SEQ ID NO 224
<211> LENGTH: 3
<212> TYPE: PRT
<213> ORGANISM: Artificial Sequence
<220> FEATURE:
<223> OTHER INFORMATION: Synthetic

<400> SEQUENCE: 224

Lys Ile Ser
 1

<210> SEQ ID NO 225
<211> LENGTH: 27
<212> TYPE: DNA
<213> ORGANISM: Artificial Sequence
<220> FEATURE:
<223> OTHER INFORMATION: Synthetic

<400> SEQUENCE: 225
atgcaagctt cacaatttcc gtggacg                                           27

<210> SEQ ID NO 226
<211> LENGTH: 9
<212> TYPE: PRT
<213> ORGANISM: Artificial Sequence
<220> FEATURE:
<223> OTHER INFORMATION: Synthetic

<400> SEQUENCE: 226

Met Gln Ala Ser Gln Phe Pro Trp Thr
 1               5

<210> SEQ ID NO 227
<211> LENGTH: 360
<212> TYPE: DNA
<213> ORGANISM: Artificial Sequence
<220> FEATURE:
<223> OTHER INFORMATION: Synthetic

<400> SEQUENCE: 227
caggtgcagc tggtacagtc tggggactgag gtgaagaagc ctggggcctc agtgaaggtc      60
```

```
tcctgcaagg tttccggata caccctcatt gacttatcca tacactgggt gcgacaggct    120
cctggagaag gccttgagtg gatgggggt tttgatcctg aagaaagtga acaatctat    180 gcacagaaat tccagggcag agtcaccatg accgaggaca catctacaga cacagcctac    240
atggagctaa gcagcctgag atctgaggac acggccgtct attactgtgt gacagagccg    300 attttggaa tccttatcca tgagtcctgg ggccagggaa ccctggtcac cgtctcctca    360
```

<210> SEQ ID NO 228
<211> LENGTH: 120
<212> TYPE: PRT
<213> ORGANISM: Artificial Sequence
<220> FEATURE:
<223> OTHER INFORMATION: Synthetic

<400> SEQUENCE: 228

```
Gln Val Gln Leu Val Gln Ser Gly Thr Glu Val Lys Lys Pro Gly Ala
1               5                   10                  15

Ser Val Lys Val Ser Cys Lys Val Ser Gly Tyr Thr Leu Ile Asp Leu
            20                  25                  30

Ser Ile His Trp Val Arg Gln Ala Pro Gly Glu Gly Leu Glu Trp Met
        35                  40                  45

Gly Gly Phe Asp Pro Glu Glu Ser Glu Thr Ile Tyr Ala Gln Lys Phe
    50                  55                  60

Gln Gly Arg Val Thr Met Thr Glu Asp Thr Ser Thr Asp Thr Ala Tyr
65                  70                  75                  80

Met Glu Leu Ser Ser Leu Arg Ser Glu Asp Thr Ala Val Tyr Tyr Cys
                85                  90                  95

Val Thr Glu Pro Ile Phe Gly Ile Leu Ile His Glu Ser Trp Gly Gln
            100                 105                 110

Gly Thr Leu Val Thr Val Ser Ser
        115                 120
```

<210> SEQ ID NO 229
<211> LENGTH: 336
<212> TYPE: DNA
<213> ORGANISM: Artificial Sequence
<220> FEATURE:
<223> OTHER INFORMATION: Synthetic

<400> SEQUENCE: 229

```
gatattgtga tgactcagac tccactctcc tcacctgtca cccttggaca gccggcctcc     60
atctcctgca ggtctagtca cagccccgta cacagtaatg gacataccta cttgagttgg    120
cttcagcaga ggccaggcca gcctccaaga atcctaattt ataagatttc tagacggttc    180
tctggggtcc cagacagatt cagtggcagt ggggcaggga cagatttcac gctgaagatc    240
agcagggtgg aaactgagga tgtcggatt tattactgca tgcaagcttc acaatttccg    300
tggacgttcg gccaagggac caaggtggaa atcaaa                              336
```

<210> SEQ ID NO 230
<211> LENGTH: 112
<212> TYPE: PRT
<213> ORGANISM: Artificial Sequence
<220> FEATURE:
<223> OTHER INFORMATION: Synthetic

<400> SEQUENCE: 230

```
Asp Ile Val Met Thr Gln Thr Pro Leu Ser Ser Pro Val Thr Leu Gly
1               5                   10                  15
```

Gln Pro Ala Ser Ile Ser Cys Arg Ser His Ser Pro Val His Ser
                20                  25                  30

Asn Gly His Thr Tyr Leu Ser Trp Leu Gln Gln Arg Pro Gly Gln Pro
             35                  40                  45

Pro Arg Ile Leu Ile Tyr Lys Ile Ser Arg Arg Phe Ser Gly Val Pro
 50                  55                  60

Asp Arg Phe Ser Gly Ser Gly Ala Gly Thr Asp Phe Thr Leu Lys Ile
65                  70                  75                  80

Ser Arg Val Glu Thr Glu Asp Val Gly Ile Tyr Tyr Cys Met Gln Ala
                85                  90                  95

Ser Gln Phe Pro Trp Thr Phe Gly Gln Gly Thr Lys Val Glu Ile Lys
            100                 105                 110

<210> SEQ ID NO 231
<211> LENGTH: 369
<212> TYPE: DNA
<213> ORGANISM: Artificial Sequence
<220> FEATURE:
<223> OTHER INFORMATION: Synthetic

<400> SEQUENCE: 231
caggtgcarc tggtggagtc tgggggaggc ttggtccagc ctgggggatc cctgagactc    60
tcctgtgcag cctctggatt caccttttagt agttattgga tgagttgggt ccgccaggct   120
ccagggaagg ggctggagtg ggtggccaac ataatgcgag atggaagtga aaaatattat   180
gtggactctg tgaagggccg attcaccatc tccagagaca acgccaagaa ctcactgtat   240
ctgcaaatga acagcctgag aggcgaggac acggctgtct attactgtgc gagagaaagg   300
gggttctaca ctaactacgg gaactggttc gaccccctggg gccagggaac cctggtcacc   360
gtctcctca                                                           369

<210> SEQ ID NO 232
<211> LENGTH: 123
<212> TYPE: PRT
<213> ORGANISM: Artificial Sequence
<220> FEATURE:
<223> OTHER INFORMATION: Synthetic

<400> SEQUENCE: 232

Gln Val Gln Leu Val Glu Ser Gly Gly Gly Leu Val Gln Pro Gly Gly
 1               5                  10                  15

Ser Leu Arg Leu Ser Cys Ala Ala Ser Gly Phe Thr Phe Ser Ser Tyr
                20                  25                  30

Trp Met Ser Trp Val Arg Gln Ala Pro Gly Lys Gly Leu Glu Trp Val
             35                  40                  45

Ala Asn Ile Met Arg Asp Gly Ser Glu Lys Tyr Tyr Val Asp Ser Val
 50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Gly Glu Asp Thr Ala Val Tyr Tyr Cys
                85                  90                  95

Ala Arg Glu Arg Gly Phe Tyr Thr Asn Tyr Gly Asn Trp Phe Asp Pro
            100                 105                 110

Trp Gly Gln Gly Thr Leu Val Thr Val Ser Ser
        115                 120

<210> SEQ ID NO 233

```
<211> LENGTH: 24
<212> TYPE: DNA
<213> ORGANISM: Artificial Sequence
<220> FEATURE:
<223> OTHER INFORMATION: Synthetic

<400> SEQUENCE: 233
ggattcacct ttagtagtta ttgg                                         24

<210> SEQ ID NO 234
<211> LENGTH: 8
<212> TYPE: PRT
<213> ORGANISM: Artificial Sequence
<220> FEATURE:
<223> OTHER INFORMATION: Synthetic

<400> SEQUENCE: 234

Gly Phe Thr Phe Ser Ser Tyr Trp
 1               5

<210> SEQ ID NO 235
<211> LENGTH: 24
<212> TYPE: DNA
<213> ORGANISM: Artificial Sequence
<220> FEATURE:
<223> OTHER INFORMATION: Synthetic

<400> SEQUENCE: 235
ataatgcgag atggaagtga gaaa                                         24

<210> SEQ ID NO 236
<211> LENGTH: 8
<212> TYPE: PRT
<213> ORGANISM: Artificial Sequence
<220> FEATURE:
<223> OTHER INFORMATION: Synthetic

<400> SEQUENCE: 236

Ile Met Arg Asp Gly Ser Glu Lys
 1               5

<210> SEQ ID NO 237
<211> LENGTH: 48
<212> TYPE: DNA
<213> ORGANISM: Artificial Sequence
<220> FEATURE:
<223> OTHER INFORMATION: Synthetic

<400> SEQUENCE: 237
gcgagagaaa gggggttcta cactaactac gggaactggt tcgacccc              48

<210> SEQ ID NO 238
<211> LENGTH: 16
<212> TYPE: PRT
<213> ORGANISM: Artificial Sequence
<220> FEATURE:
<223> OTHER INFORMATION: Synthetic

<400> SEQUENCE: 238

Ala Arg Glu Arg Gly Phe Tyr Thr Asn Tyr Gly Asn Trp Phe Asp Pro
 1               5                  10                  15

<210> SEQ ID NO 239
<211> LENGTH: 339
<212> TYPE: DNA
<213> ORGANISM: Artificial Sequence
<220> FEATURE:
```

<223> OTHER INFORMATION: Synthetic

<400> SEQUENCE: 239

```
gacatcctga tgacccagtc tccactctcc ctgaccgtca cccctggaga gtcggcctcc    60
atctcctgca ggtctagtca gagcctcctg catagttatg gatacaattc tttggattgg   120
tacctgcaga agccagggca gtctccacag ttcctgatct atttggtttc taatcgggcc   180
tccggggtcc ctgacaggtt cagtggcagt ggatcaggca cagattttac actgaaaatc   240
agcagagtgg aggctgagga tgttggggtt tattactgca tgcaagttct acaaactccg   300
tacactttg gccaggggac caaggtggag atcaaacga                           339
```

<210> SEQ ID NO 240
<211> LENGTH: 113
<212> TYPE: PRT
<213> ORGANISM: Artificial Sequence
<220> FEATURE:
<223> OTHER INFORMATION: Synthetic

<400> SEQUENCE: 240

```
Asp Ile Leu Met Thr Gln Ser Pro Leu Ser Leu Thr Val Thr Pro Gly
 1               5                  10                  15

Glu Ser Ala Ser Ile Ser Cys Arg Ser Ser Gln Ser Leu Leu His Ser
            20                  25                  30

Tyr Gly Tyr Asn Ser Leu Asp Trp Tyr Leu Gln Lys Pro Gly Gln Ser
        35                  40                  45

Pro Gln Phe Leu Ile Tyr Leu Val Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Val
                85                  90                  95

Leu Gln Thr Pro Tyr Thr Phe Gly Gln Gly Thr Lys Val Glu Ile Lys
            100                 105                 110

Arg
```

<210> SEQ ID NO 241
<211> LENGTH: 33
<212> TYPE: DNA
<213> ORGANISM: Artificial Sequence
<220> FEATURE:
<223> OTHER INFORMATION: Synthetic

<400> SEQUENCE: 241

```
cagagcctcc tgcatagtta tggatacaat tct                                 33
```

<210> SEQ ID NO 242
<211> LENGTH: 11
<212> TYPE: PRT
<213> ORGANISM: Artificial Sequence
<220> FEATURE:
<223> OTHER INFORMATION: Synthetic

<400> SEQUENCE: 242

```
Gln Ser Leu Leu His Ser Tyr Gly Tyr Asn Ser
 1               5                  10
```

<210> SEQ ID NO 243
<211> LENGTH: 9
<212> TYPE: DNA
<213> ORGANISM: Artificial Sequence

```
<220> FEATURE:
<223> OTHER INFORMATION: Synthetic

<400> SEQUENCE: 243 ttggtttct                                                                  9

<210> SEQ ID NO 244
<211> LENGTH: 3
<212> TYPE: PRT
<213> ORGANISM: Artificial Sequence
<220> FEATURE:
<223> OTHER INFORMATION: Synthetic

<400> SEQUENCE: 244

Leu Val Ser
  1

<210> SEQ ID NO 245
<211> LENGTH: 27
<212> TYPE: DNA
<213> ORGANISM: Artificial Sequence
<220> FEATURE:
<223> OTHER INFORMATION: Synthetic

<400> SEQUENCE: 245
atgcaagttc tacaaactcc gtacact                                             27

<210> SEQ ID NO 246
<211> LENGTH: 9
<212> TYPE: PRT
<213> ORGANISM: Artificial Sequence
<220> FEATURE:
<223> OTHER INFORMATION: Synthetic

<400> SEQUENCE: 246

Met Gln Val Leu Gln Thr Pro Tyr Thr
  1               5

<210> SEQ ID NO 247
<211> LENGTH: 369
<212> TYPE: DNA
<213> ORGANISM: Artificial Sequence
<220> FEATURE:
<223> OTHER INFORMATION: Synthetic

<400> SEQUENCE: 247
gaggtgcagc tggtggagtc tgggggaggc ttggtccagc ctgggggatc cctgagactc         60
tcctgtgcag cctctggatt cacctttagt agttattgga tgagttgggt ccgccaggct        120
ccagggaagg ggctggagtg ggtggccaac ataatgcgag atggaagtga gaaatattat        180
gtggactctg tgaagggccg attcaccatc tccagagaca acgccaagaa ctcactgtat        240
ctgcaaatga acagcctgag aggcgaggac acggctgtct attactgtgc gagagaaagg        300
gggttctaca ctaactacgg gaactggttc gaccccctggg gccagggaac cctggtcacc       360
gtctcctca                                                                369

<210> SEQ ID NO 248
<211> LENGTH: 123
<212> TYPE: PRT
<213> ORGANISM: Artificial Sequence
<220> FEATURE:
<223> OTHER INFORMATION: Synthetic

<400> SEQUENCE: 248
```

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Trp Met Ser Trp Val Arg Gln Ala Pro Gly Lys Gly Leu Glu Trp Val
        35                  40                  45

Ala Asn Ile Met Arg Asp Gly Ser Glu Lys Tyr Tyr Val Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Gly Glu Asp Thr Ala Val Tyr Tyr Cys
            85                  90                  95

Ala Arg Glu Arg Gly Phe Tyr Thr Asn Tyr Gly Asn Trp Phe Asp Pro
            100                 105                 110

Trp Gly Gln Gly Thr Leu Val Thr Val Ser Ser
            115                 120

<210> SEQ ID NO 249
<211> LENGTH: 336
<212> TYPE: DNA
<213> ORGANISM: Artificial Sequence
<220> FEATURE:
<223> OTHER INFORMATION: Synthetic

<400> SEQUENCE: 249
gacatcgtga tgacccagtc tccactctcc ctgaccgtca cccctggaga gtcggcctcc      60
atctcctgca ggtctagtca gagcctcctg catagttatg gatacaattc tttggattgg     120
tacctgcaga agccagggca gtctccacag ttcctgatct atttggtttc taatcgggcc     180
tccggggtcc ctgacaggtt cagtggcagt ggatcaggca cagattttac actgaaaatc     240
agcagagtgg aggctgagga tgttggggtt tattactgca tgcaagttct acaaactccg     300 tacactttg gccaggggac caagctggag atcaaa                                336

<210> SEQ ID NO 250
<211> LENGTH: 112
<212> TYPE: PRT
<213> ORGANISM: Artificial Sequence
<220> FEATURE:
<223> OTHER INFORMATION: Synthetic

<400> SEQUENCE: 250

Asp Ile Val Met Thr Gln Ser Pro Leu Ser Leu Thr Val Thr Pro Gly
1               5                   10                  15

Glu Ser Ala Ser Ile Ser Cys Arg Ser Ser Gln Ser Leu Leu His Ser
            20                  25                  30

Tyr Gly Tyr Asn Ser Leu Asp Trp Tyr Leu Gln Lys Pro Gly Gln Ser
        35                  40                  45

Pro Gln Phe Leu Ile Tyr Leu Val Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Val
            85                  90                  95

Leu Gln Thr Pro Tyr Thr Phe Gly Gln Gly Thr Lys Leu Glu Ile Lys
            100                 105                 110

<210> SEQ ID NO 251

<210> SEQ ID NO 251
<211> LENGTH: 360
<212> TYPE: DNA
<213> ORGANISM: Artificial Sequence
<220> FEATURE:
<223> OTHER INFORMATION: Synthetic

<400> SEQUENCE: 251

```
caggtgcagc tggtggagtc tgggggaggc gtggtccagc ctggggaggtc cctgagactc     60
tcctgtgcag cgtctggatt caccttcagt aattatggca tgcactgggt ccgccaggct    120
ccaggcaagg ggctggagtg ggtggcagtt atttggtatg atgaaagtag taaatactat    180
acagactccg tgaagggccg attcaccatc tccagagaca attcccagaa cacgctgtat    240
ctgcaaatga ccagcctgag agccgaggac acggctgtgt attactgtgc gagagatcgc    300
tggacctact cccactactt tgaatattgg ggccagggaa ccctggtcac tgtctcctca    360
```

<210> SEQ ID NO 252
<211> LENGTH: 120
<212> TYPE: PRT
<213> ORGANISM: Artificial Sequence
<220> FEATURE:
<223> OTHER INFORMATION: Synthetic

<400> SEQUENCE: 252

Gln Val Gln Leu Val Glu Ser Gly Gly Gly Val Val Gln Pro Gly Arg
1               5                   10                  15
Ser Leu Arg Leu Ser Cys Ala Ala Ser Gly Phe Thr Phe Ser Asn Tyr
            20                  25                  30
Gly Met His Trp Val Arg Gln Ala Pro Gly Lys Gly Leu Glu Trp Val
        35                  40                  45
Ala Val Ile Trp Tyr Asp Glu Ser Ser Lys Tyr Tyr Thr Asp Ser Val
    50                  55                  60
Lys Gly Arg Phe Thr Ile Ser Arg Asp Asn Ser Gln Asn Thr Leu Tyr
65                  70                  75                  80
Leu Gln Met Thr Ser Leu Arg Ala Glu Asp Thr Ala Val Tyr Tyr Cys
                85                  90                  95
Ala Arg Asp Arg Trp Thr Tyr Ser His Tyr Phe Glu Tyr Trp Gly Gln
            100                 105                 110
Gly Thr Leu Val Thr Val Ser Ser
        115                 120

<210> SEQ ID NO 253
<211> LENGTH: 24
<212> TYPE: DNA
<213> ORGANISM: Artificial Sequence
<220> FEATURE:
<223> OTHER INFORMATION: Synthetic

<400> SEQUENCE: 253

```
ggattcacct tcagtaatta tggc                                             24
```

<210> SEQ ID NO 254
<211> LENGTH: 8
<212> TYPE: PRT
<213> ORGANISM: Artificial Sequence
<220> FEATURE:
<223> OTHER INFORMATION: Synthetic

<400> SEQUENCE: 254

Gly Phe Thr Phe Ser Asn Tyr Gly
1               5

<210> SEQ ID NO 255
<211> LENGTH: 24
<212> TYPE: DNA
<213> ORGANISM: Artificial Sequence
<220> FEATURE:
<223> OTHER INFORMATION: Synthetic

<400> SEQUENCE: 255
atttggtatg atgaaagtag taaa                                      24

<210> SEQ ID NO 256
<211> LENGTH: 8
<212> TYPE: PRT
<213> ORGANISM: Artificial Sequence
<220> FEATURE:
<223> OTHER INFORMATION: Synthetic

<400> SEQUENCE: 256

Ile Trp Tyr Asp Glu Ser Ser Lys
 1               5

<210> SEQ ID NO 257
<211> LENGTH: 39
<212> TYPE: DNA
<213> ORGANISM: Artificial Sequence
<220> FEATURE:
<223> OTHER INFORMATION: Synthetic

<400> SEQUENCE: 257
gcgagagatc gctggaccta ctcccactac tttgaatat                      39

<210> SEQ ID NO 258
<211> LENGTH: 13
<212> TYPE: PRT
<213> ORGANISM: Artificial Sequence
<220> FEATURE:
<223> OTHER INFORMATION: Synthetic

<400> SEQUENCE: 258

Ala Arg Asp Arg Trp Thr Tyr Ser His Tyr Phe Glu Tyr
 1               5                  10

<210> SEQ ID NO 259
<211> LENGTH: 324
<212> TYPE: DNA
<213> ORGANISM: Artificial Sequence
<220> FEATURE:
<223> OTHER INFORMATION: Synthetic

<400> SEQUENCE: 259
gacatccagt tgacccagtc tccatcttcc gtgtctgcat ctgtaggaga cagagtcacc     60
atcacttgtc gggcgagtca gggtattagc agctgggtag cctggtatca gcagaaacca    120
gggaaagccc ctaaactcct gatctatgct gcatccagtt tgcaaagtgg ggtcccatct    180
aggttcagcg gcagtggatc tgggacagat ttcactctca ccatcagcag cctgcagcct    240
gaagattttg caacttacta ttgtcaacag gctaacagtt tccctcggac gttcggccaa    300
gggaccaaag tggagatcaa acga                                          324

<210> SEQ ID NO 260
<211> LENGTH: 108
<212> TYPE: PRT
<213> ORGANISM: Artificial Sequence
<220> FEATURE:
<223> OTHER INFORMATION: Synthetic

<400> SEQUENCE: 260

| Asp | Ile | Gln | Leu | Thr | Gln | Ser | Pro | Ser | Ser | Val | Ser | Ala | Ser | Val | Gly |
|---|---|---|---|---|---|---|---|---|---|---|---|---|---|---|---|
| 1 | | | | 5 | | | | | 10 | | | | | 15 | |

| Asp | Arg | Val | Thr | Ile | Thr | Cys | Arg | Ala | Ser | Gln | Gly | Ile | Ser | Ser | Trp |
|---|---|---|---|---|---|---|---|---|---|---|---|---|---|---|---|
| | | | 20 | | | | | 25 | | | | | 30 | | |

| Val | Ala | Trp | Tyr | Gln | Gln | Lys | Pro | Gly | Lys | Ala | Pro | Lys | Leu | Leu | Ile |
|---|---|---|---|---|---|---|---|---|---|---|---|---|---|---|---|
| | | 35 | | | | | 40 | | | | | 45 | | | |

| Tyr | Ala | Ala | Ser | Ser | Leu | Gln | Ser | Gly | Val | Pro | Ser | Arg | Phe | Ser | Gly |
|---|---|---|---|---|---|---|---|---|---|---|---|---|---|---|---|
| | 50 | | | | | 55 | | | | | 60 | | | | |

| Ser | Gly | Ser | Gly | Thr | Asp | Phe | Thr | Leu | Thr | Ile | Ser | Ser | Leu | Gln | Pro |
|---|---|---|---|---|---|---|---|---|---|---|---|---|---|---|---|
| 65 | | | | | 70 | | | | | 75 | | | | | 80 |

| Glu | Asp | Phe | Ala | Thr | Tyr | Tyr | Cys | Gln | Gln | Ala | Asn | Ser | Phe | Pro | Arg |
|---|---|---|---|---|---|---|---|---|---|---|---|---|---|---|---|
| | | | | 85 | | | | | 90 | | | | | 95 | |

| Thr | Phe | Gly | Gln | Gly | Thr | Lys | Val | Glu | Ile | Lys | Arg |
|---|---|---|---|---|---|---|---|---|---|---|---|
| | | | 100 | | | | | 105 | | | |

<210> SEQ ID NO 261
<211> LENGTH: 18
<212> TYPE: DNA
<213> ORGANISM: Artificial Sequence
<220> FEATURE:
<223> OTHER INFORMATION: Synthetic

<400> SEQUENCE: 261
cagggtatta gcagctgg                                                 18

<210> SEQ ID NO 262
<211> LENGTH: 6
<212> TYPE: PRT
<213> ORGANISM: Artificial Sequence
<220> FEATURE:
<223> OTHER INFORMATION: Synthetic

<400> SEQUENCE: 262

| Gln | Gly | Ile | Ser | Ser | Trp |
|---|---|---|---|---|---|
| 1 | | | | 5 | |

<210> SEQ ID NO 263
<211> LENGTH: 9
<212> TYPE: DNA
<213> ORGANISM: Artificial Sequence
<220> FEATURE:
<223> OTHER INFORMATION: Synthetic

<400> SEQUENCE: 263 gctgcatcc                                                            9

<210> SEQ ID NO 264
<211> LENGTH: 3
<212> TYPE: PRT
<213> ORGANISM: Artificial Sequence
<220> FEATURE:
<223> OTHER INFORMATION: Synthetic

<400> SEQUENCE: 264

| Ala | Ala | Ser |
|---|---|---|
| 1 | | |

<210> SEQ ID NO 265
<211> LENGTH: 27
<212> TYPE: DNA
<213> ORGANISM: Artificial Sequence
<220> FEATURE:
<223> OTHER INFORMATION: Synthetic

<400> SEQUENCE: 265
caacaggcta acagtttccc tcggacg                                    27

<210> SEQ ID NO 266
<211> LENGTH: 9
<212> TYPE: PRT
<213> ORGANISM: Artificial Sequence
<220> FEATURE:
<223> OTHER INFORMATION: Synthetic

<400> SEQUENCE: 266

Gln Gln Ala Asn Ser Phe Pro Arg Thr
1               5

<210> SEQ ID NO 267
<211> LENGTH: 360
<212> TYPE: DNA
<213> ORGANISM: Artificial Sequence
<220> FEATURE:
<223> OTHER INFORMATION: Synthetic

<400> SEQUENCE: 267
caggtgcagc tggtggagtc tgggggaggc gtggtccagc ctggggaggtc cctgagactc      60 tcctgtgcag cgtctggatt caccttcagt aattatggca tgcactgggt ccgccaggct     120
ccaggcaagg ggctggagtg ggtggcagtt atttggtatg atgaaagtag taaatactat     180
acagactccg tgaagggccg attcaccatc tccagagaca attcccagaa cacgctgtat     240
ctgcaaatga ccagcctgag agccgaggac acggctgtgt attactgtgc gagagatcgc     300
tggacctact cccactactt tgaatattgg ggccagggaa ccctggtcac cgtctcctca     360

<210> SEQ ID NO 268
<211> LENGTH: 120
<212> TYPE: PRT
<213> ORGANISM: Artificial Sequence
<220> FEATURE:
<223> OTHER INFORMATION: Synthetic

<400> SEQUENCE: 268

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Asn Tyr
            20                  25                  30

Gly Met His Trp Val Arg Gln Ala Pro Gly Lys Gly Leu Glu Trp Val
        35                  40                  45

Ala Val Ile Trp Tyr Asp Glu Ser Ser Lys Tyr Tyr Thr Asp Ser Val
    50                  55                  60

Lys Gly Arg Phe Thr Ile Ser Arg Asp Asn Ser Gln Asn Thr Leu Tyr
65                  70                  75                  80

Leu Gln Met Thr Ser Leu Arg Ala Glu Asp Thr Ala Val Tyr Tyr Cys
                85                  90                  95

Ala Arg Asp Arg Trp Thr Tyr Ser His Tyr Phe Glu Tyr Trp Gly Gln
            100                 105                 110

Gly Thr Leu Val Thr Val Ser Ser
        115                 120

<210> SEQ ID NO 269
<211> LENGTH: 321

```
<212> TYPE: DNA
<213> ORGANISM: Artificial Sequence
<220> FEATURE:
<223> OTHER INFORMATION: Synthetic

<400> SEQUENCE: 269
gacatccaga tgacccagtc tccatcttcc gtgtctgcat ctgtaggaga cagagtcacc      60
atcacttgtc gggcgagtca gggtattagc agctgggtag cctggtatca gcagaaacca    120
gggaaagccc ctaaactcct gatctatgct gcatccagtt tgcaaagtgg ggtcccatct    180
aggttcagcg gcagtggatc tgggacagat tcactctca ccatcagcag cctgcagcct     240
gaagattttg caacttacta ttgtcaacag gctaacagtt tccctcggac gttcggccaa    300
gggaccaagg tggagatcaa a                                                321

<210> SEQ ID NO 270
<211> LENGTH: 107
<212> TYPE: PRT
<213> ORGANISM: Artificial Sequence
<220> FEATURE:
<223> OTHER INFORMATION: Synthetic

<400> SEQUENCE: 270

Asp Ile Gln Met Thr Gln Ser Pro Ser Ser Val Ser Ala Ser Val Gly
 1               5                  10                  15

Asp Arg Val Thr Ile Thr Cys Arg Ala Ser Gln Gly Ile Ser Ser Trp
            20                  25                  30

Val Ala Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ala Asn Ser Phe Pro Arg
                85                  90                  95

Thr Phe Gly Gln Gly Thr Lys Val Glu Ile Lys
            100                 105

<210> SEQ ID NO 271
<211> LENGTH: 360
<212> TYPE: DNA
<213> ORGANISM: Artificial Sequence
<220> FEATURE:
<223> OTHER INFORMATION: Synthetic

<400> SEQUENCE: 271
caggtgcagc tggtggagtc tggggggagc gtggtccagc ctgggaggtc cctgagactc      60
tcctgtgcag cgtctggatt caccttcagt aactatggca tgcattgggt ccgccaggct    120
ccaggcaagg gtctggagtg gtggcagtt atttggtatg atgaaagtgg taaacactat      180
gcagactccg tgaagggccg attcaccatc tccagagaca attcccagaa cacgctgtat    240
ctgcaaatga ccagcctgag agccgaggac acggctgtgt attactgtgc gagagatcgc    300
tggacctact cccactactt tgaatattgg ggccagggaa ccctggtcac cgtctcctca    360

<210> SEQ ID NO 272
<211> LENGTH: 120
<212> TYPE: PRT
<213> ORGANISM: Artificial Sequence
<220> FEATURE:
<223> OTHER INFORMATION: Synthetic
```

<400> SEQUENCE: 272

| Gln | Val | Gln | Leu | Val | Glu | Ser | Gly | Gly | Val | Val | Gln | Pro | Gly | Arg |
|---|---|---|---|---|---|---|---|---|---|---|---|---|---|---|
| 1 | | | | 5 | | | | | 10 | | | | | 15 |

| Ser | Leu | Arg | Leu | Ser | Cys | Ala | Ala | Ser | Gly | Phe | Thr | Phe | Ser | Asn | Tyr |
|---|---|---|---|---|---|---|---|---|---|---|---|---|---|---|---|
| | | | 20 | | | | | 25 | | | | | 30 | | |

| Gly | Met | His | Trp | Val | Arg | Gln | Ala | Pro | Gly | Lys | Gly | Leu | Glu | Trp | Val |
|---|---|---|---|---|---|---|---|---|---|---|---|---|---|---|---|
| | | 35 | | | | | 40 | | | | | 45 | | | |

| Ala | Val | Ile | Trp | Tyr | Asp | Glu | Ser | Gly | Lys | His | Tyr | Ala | Asp | Ser | Val |
|---|---|---|---|---|---|---|---|---|---|---|---|---|---|---|---|
| 50 | | | | | 55 | | | | | 60 | | | | | |

| Lys | Gly | Arg | Phe | Thr | Ile | Ser | Arg | Asp | Asn | Ser | Gln | Asn | Thr | Leu | Tyr |
|---|---|---|---|---|---|---|---|---|---|---|---|---|---|---|---|
| 65 | | | | | 70 | | | | | 75 | | | | | 80 |

| Leu | Gln | Met | Thr | Ser | Leu | Arg | Ala | Glu | Asp | Thr | Ala | Val | Tyr | Tyr | Cys |
|---|---|---|---|---|---|---|---|---|---|---|---|---|---|---|---|
| | | | | 85 | | | | | 90 | | | | | 95 | |

| Ala | Arg | Asp | Arg | Trp | Thr | Tyr | Ser | His | Tyr | Phe | Glu | Tyr | Trp | Gly | Gln |
|---|---|---|---|---|---|---|---|---|---|---|---|---|---|---|---|
| | | | 100 | | | | | 105 | | | | | 110 | | |

| Gly | Thr | Leu | Val | Thr | Val | Ser | Ser |
|---|---|---|---|---|---|---|---|
| | | | 115 | | | | 120 |

<210> SEQ ID NO 273
<211> LENGTH: 24
<212> TYPE: DNA
<213> ORGANISM: Artificial Sequence
<220> FEATURE:
<223> OTHER INFORMATION: Synthetic

<400> SEQUENCE: 273
ggattcacct tcagtaacta tggc          24

<210> SEQ ID NO 274
<211> LENGTH: 8
<212> TYPE: PRT
<213> ORGANISM: Artificial Sequence
<220> FEATURE:
<223> OTHER INFORMATION: Synthetic

<400> SEQUENCE: 274

| Gly | Phe | Thr | Phe | Ser | Asn | Tyr | Gly |
|---|---|---|---|---|---|---|---|
| 1 | | | | 5 | | | |

<210> SEQ ID NO 275
<211> LENGTH: 24
<212> TYPE: DNA
<213> ORGANISM: Artificial Sequence
<220> FEATURE:
<223> OTHER INFORMATION: Synthetic

<400> SEQUENCE: 275
atttggtatg atgaaagtgg taaa          24

<210> SEQ ID NO 276
<211> LENGTH: 8
<212> TYPE: PRT
<213> ORGANISM: Artificial Sequence
<220> FEATURE:
<223> OTHER INFORMATION: Synthetic

<400> SEQUENCE: 276

| Ile | Trp | Tyr | Asp | Glu | Ser | Gly | Lys |
|---|---|---|---|---|---|---|---|
| 1 | | | | 5 | | | |

<210> SEQ ID NO 277

```
<211> LENGTH: 39
<212> TYPE: DNA
<213> ORGANISM: Artificial Sequence
<220> FEATURE:
<223> OTHER INFORMATION: Synthetic

<400> SEQUENCE: 277
gcgagagatc gctggaccta ctcccactac tttgaatat                              39

<210> SEQ ID NO 278
<211> LENGTH: 13
<212> TYPE: PRT
<213> ORGANISM: Artificial Sequence
<220> FEATURE:
<223> OTHER INFORMATION: Synthetic

<400> SEQUENCE: 278

Ala Arg Asp Arg Trp Thr Tyr Ser His Tyr Phe Glu Tyr
 1               5                  10

<210> SEQ ID NO 279
<211> LENGTH: 324
<212> TYPE: DNA
<213> ORGANISM: Artificial Sequence
<220> FEATURE:
<223> OTHER INFORMATION: Synthetic

<400> SEQUENCE: 279
gacatccaga tgacccagtc tccatcttcc gtgtctgcat ctgtaggaga cagagtcacc      60
atcacttgtc gggcgagtca ggatattagc agctgggtag cctggtatca acagaaacca    120
gggaaagccc ctaaactcct gatctatgct gcatccagtt tgcaaagtgg ggtcccatct    180
aggttcagcg gcagtggatc tgggacagat ttcactctca ccatcagcag cctgcagcct    240
gaagattttg caacttacta ttgtcaacag gctaacagtt ccctcggac gttcggccaa    300 gggaccaagg tggagatcaa acga                                            324

<210> SEQ ID NO 280
<211> LENGTH: 108
<212> TYPE: PRT
<213> ORGANISM: Artificial Sequence
<220> FEATURE:
<223> OTHER INFORMATION: Synthetic

<400> SEQUENCE: 280

Asp Ile Gln Met Thr Gln Ser Pro Ser Ser Val Ser Ala Ser Val Gly
 1               5                  10                  15

Asp Arg Val Thr Ile Thr Cys Arg Ala Ser Gln Asp Ile Ser Ser Trp
                20                  25                  30

Val Ala Trp Tyr Gln Gln Lys Pro Gly Lys Ala Pro Lys Leu Leu Ile
            35                  40                  45

Tyr Ala Ala Ser Ser Leu Gln Ser Gly Val Pro Ser Arg Phe Ser Gly
        50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Ala Asn Ser Phe Pro Arg
                85                  90                  95

Thr Phe Gly Gln Gly Thr Lys Val Glu Ile Lys Arg
            100                 105

<210> SEQ ID NO 281
<211> LENGTH: 18
```

```
<212> TYPE: DNA
<213> ORGANISM: Artificial Sequence
<220> FEATURE:
<223> OTHER INFORMATION: Synthetic

<400> SEQUENCE: 281
caggatatta gcagctgg                                                    18

<210> SEQ ID NO 282
<211> LENGTH: 6
<212> TYPE: PRT
<213> ORGANISM: Artificial Sequence
<220> FEATURE:
<223> OTHER INFORMATION: Synthetic

<400> SEQUENCE: 282

Gln Asp Ile Ser Ser Trp
 1               5

<210> SEQ ID NO 283
<211> LENGTH: 9
<212> TYPE: DNA
<213> ORGANISM: Artificial Sequence
<220> FEATURE:
<223> OTHER INFORMATION: Synthetic

<400> SEQUENCE: 283 gctgcatcc                                                               9

<210> SEQ ID NO 284
<211> LENGTH: 3
<212> TYPE: PRT
<213> ORGANISM: Artificial Sequence
<220> FEATURE:
<223> OTHER INFORMATION: Synthetic

<400> SEQUENCE: 284

Ala Ala Ser
 1

<210> SEQ ID NO 285
<211> LENGTH: 27
<212> TYPE: DNA
<213> ORGANISM: Artificial Sequence
<220> FEATURE:
<223> OTHER INFORMATION: Synthetic

<400> SEQUENCE: 285
caacaggcta acagtttccc tcggacg                                          27

<210> SEQ ID NO 286
<211> LENGTH: 9
<212> TYPE: PRT
<213> ORGANISM: Artificial Sequence
<220> FEATURE:
<223> OTHER INFORMATION: Synthetic

<400> SEQUENCE: 286

Gln Gln Ala Asn Ser Phe Pro Arg Thr
 1               5

<210> SEQ ID NO 287
<211> LENGTH: 360
<212> TYPE: DNA
<213> ORGANISM: Artificial Sequence
<220> FEATURE:
<223> OTHER INFORMATION: Synthetic
```

<400> SEQUENCE: 287

```
caggtgcagc tggtggagtc tgggggaggc gtggtccagc ctggagggtc cctgagactc    60
tcctgtgcag cgtctggatt caccttcagt aactatggca tgcattgggt ccgccaggct   120
ccaggcaagg gtctggagtg gtggcagtt atttggtatg atgaaagtgg taaacactat   180
gcagactccg tgaagggccg attcaccatc tccagagaca attcccagaa cacgctgtat   240
ctgcaaatga ccagcctgag agccgaggac acggctgtgt attactgtgc gagagatcgc   300
tggacctact cccactactt tgaatattgg ggccagggaa ccctggtcac tgtctcctca   360
```

<210> SEQ ID NO 288
<211> LENGTH: 120
<212> TYPE: PRT
<213> ORGANISM: Artificial Sequence
<220> FEATURE:
<223> OTHER INFORMATION: Synthetic

<400> SEQUENCE: 288

```
Gln Val Gln Leu Val Glu Ser Gly Gly Gly Val Val Gln Pro Gly Arg
1               5                   10                  15
Ser Leu Arg Leu Ser Cys Ala Ala Ser Gly Phe Thr Phe Ser Asn Tyr
            20                  25                  30
Gly Met His Trp Val Arg Gln Ala Pro Gly Lys Gly Leu Glu Trp Val
        35                  40                  45
Ala Val Ile Trp Tyr Asp Glu Ser Gly Lys His Tyr Ala Asp Ser Val
    50                  55                  60
Lys Gly Arg Phe Thr Ile Ser Arg Asp Asn Ser Gln Asn Thr Leu Tyr
65                  70                  75                  80
Leu Gln Met Thr Ser Leu Arg Ala Glu Asp Thr Ala Val Tyr Tyr Cys
                85                  90                  95
Ala Arg Asp Arg Trp Thr Tyr Ser His Tyr Phe Glu Tyr Trp Gly Gln
            100                 105                 110
Gly Thr Leu Val Thr Val Ser Ser
        115                 120
```

<210> SEQ ID NO 289
<211> LENGTH: 321
<212> TYPE: DNA
<213> ORGANISM: Artificial Sequence
<220> FEATURE:
<223> OTHER INFORMATION: Synthetic

<400> SEQUENCE: 289

```
gacatccaga tgacccagtc tccatcttcc gtgtctgcat ctgtaggaga cagagtcacc    60
atcacttgtc gggcgagtca ggatattagc agctgggtag cctggtatca acagaaacca   120
gggaaagccc ctaaactcct gatctatgct gcatccagtt tgcaaagtgg ggtcccatct   180
aggttcagcg gcagtggatc tgggacagat ttcactctca ccatcagcag cctgcagcct   240
gaagattttg caacttacta ttgtcaacag gctaacagtt tccctcggac gttcggccaa   300
gggaccaagg tggagatcaa a                                             321
```

<210> SEQ ID NO 290
<211> LENGTH: 107
<212> TYPE: PRT
<213> ORGANISM: Artificial Sequence
<220> FEATURE:
<223> OTHER INFORMATION: Synthetic

<400> SEQUENCE: 290

Asp Ile Gln Met Thr Gln Ser Pro Ser Ser Val Ser Ala Ser Val Gly
1               5                   10                  15

Asp Arg Val Thr Ile Thr Cys Arg Ala Ser Gln Asp Ile Ser Ser Trp
            20                  25                  30

Val Ala Trp Tyr Gln Gln Lys Pro Gly Lys Ala Pro Lys Leu Leu Ile
        35                  40                  45

Tyr Ala Ala Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ala Asn Ser Phe Pro Arg
                85                  90                  95

Thr Phe Gly Gln Gly Thr Lys Val Glu Ile Lys
            100                 105

<210> SEQ ID NO 291
<211> LENGTH: 360
<212> TYPE: DNA
<213> ORGANISM: Artificial Sequence
<220> FEATURE:
<223> OTHER INFORMATION: Synthetic

<400> SEQUENCE: 291
gaggtgcagt tgttggagtc tgggggaggc gtggtccagc ctggggaggtc cctgagactc    60
tcctgtgcag cgtctggatt caccttcagt aattatggca tgcactgggt ccgccaggct   120
ccaggcaagg ggctggagtg ggtggcagtt atttggtatg atgaaagtag taaatactat   180
acagactccg tgaagggccg attcaccatc tccagagaca attcccagaa cacgctgtat   240
ctgcaaatga ccagcctgag agccgaggac acggctgtgt attactgtgc gagagatcgc   300
tggacctact cccactactt tgaatattgg ggccagggaa ccctggtcac cgtctcctca   360

<210> SEQ ID NO 292
<211> LENGTH: 120
<212> TYPE: PRT
<213> ORGANISM: Artificial Sequence
<220> FEATURE:
<223> OTHER INFORMATION: Synthetic

<400> SEQUENCE: 292

Glu Val Gln Leu Leu Glu Ser Gly Gly Gly Val Val Gln Pro Gly Arg
1               5                   10                  15

Ser Leu Arg Leu Ser Cys Ala Ala Ser Gly Phe Thr Phe Ser Asn Tyr
            20                  25                  30

Gly Met His Trp Val Arg Gln Ala Pro Gly Lys Gly Leu Glu Trp Val
        35                  40                  45

Ala Val Ile Trp Tyr Asp Glu Ser Ser Lys Tyr Tyr Thr Asp Ser Val
    50                  55                  60

Lys Gly Arg Phe Thr Ile Ser Arg Asp Asn Ser Gln Asn Thr Leu Tyr
65                  70                  75                  80

Leu Gln Met Thr Ser Leu Arg Ala Glu Asp Thr Ala Val Tyr Tyr Cys
                85                  90                  95

Ala Arg Asp Arg Trp Thr Tyr Ser His Tyr Phe Glu Tyr Trp Gly Gln
            100                 105                 110

Gly Thr Leu Val Thr Val Ser Ser
        115                 120

```
<210> SEQ ID NO 293
<211> LENGTH: 24
<212> TYPE: DNA
<213> ORGANISM: Artificial Sequence
<220> FEATURE:
<223> OTHER INFORMATION: Synthetic

<400> SEQUENCE: 293
ggattcacct tcagtaatta tggc                                          24

<210> SEQ ID NO 294
<211> LENGTH: 8
<212> TYPE: PRT
<213> ORGANISM: Artificial Sequence
<220> FEATURE:
<223> OTHER INFORMATION: Synthetic

<400> SEQUENCE: 294

Gly Phe Thr Phe Ser Asn Tyr Gly
 1               5

<210> SEQ ID NO 295
<211> LENGTH: 24
<212> TYPE: DNA
<213> ORGANISM: Artificial Sequence
<220> FEATURE:
<223> OTHER INFORMATION: Synthetic

<400> SEQUENCE: 295
atttggtatg atgaaagtag taaa                                          24

<210> SEQ ID NO 296
<211> LENGTH: 8
<212> TYPE: PRT
<213> ORGANISM: Artificial Sequence
<220> FEATURE:
<223> OTHER INFORMATION: Synthetic

<400> SEQUENCE: 296

Ile Trp Tyr Asp Glu Ser Ser Lys
 1               5

<210> SEQ ID NO 297
<211> LENGTH: 39
<212> TYPE: DNA
<213> ORGANISM: Artificial Sequence
<220> FEATURE:
<223> OTHER INFORMATION: Synthetic

<400> SEQUENCE: 297
gcgagagatc gctggaccta ctcccactac tttgaatat                          39

<210> SEQ ID NO 298
<211> LENGTH: 13
<212> TYPE: PRT
<213> ORGANISM: Artificial Sequence
<220> FEATURE:
<223> OTHER INFORMATION: Synthetic

<400> SEQUENCE: 298

Ala Arg Asp Arg Trp Thr Tyr Ser His Tyr Phe Glu Tyr
 1               5                  10

<210> SEQ ID NO 299
<211> LENGTH: 324
<212> TYPE: DNA
```

<213> ORGANISM: Artificial Sequence
<220> FEATURE:
<223> OTHER INFORMATION: Synthetic

<400> SEQUENCE: 299

```
gacatccaga tgacccagtc tccatcttcc gtgtctgcat ctgtaggaga cagagtcacc    60
atcacttgtc gggcgagtca gggtattagc agctgggtag cctggtatca gcagaaacca   120
gggaaagccc ctaaactcct gatctatgct gcatccagtt tgcaaagtgg ggtcccatct   180
aggttcagcg gcagtggatc tgggacagat ttcactctca ccatcagcag cctgcagcct   240
gaagattttg caacttacta ttgtcaacag gctaacagtt ccctcggac gttcggccaa   300
gggaccaagg tggagatcaa acga                                          324
```

<210> SEQ ID NO 300
<211> LENGTH: 108
<212> TYPE: PRT
<213> ORGANISM: Artificial Sequence
<220> FEATURE:
<223> OTHER INFORMATION: Synthetic

<400> SEQUENCE: 300

```
Asp Ile Gln Met Thr Gln Ser Pro Ser Ser Val Ser Ala Ser Val Gly
 1               5                  10                  15
Asp Arg Val Thr Ile Thr Cys Arg Ala Ser Gln Gly Ile Ser Ser Trp
            20                  25                  30
Val Ala Trp Tyr Gln Gln Lys Pro Gly Lys Ala Pro Lys Leu Leu Ile
        35                  40                  45
Tyr Ala Ala Ser Ser Leu Gln Ser Gly Val Pro Ser Arg Phe Ser Gly
    50                  55                  60
Ser Gly Ser Gly Thr Asp Phe Thr Leu Thr Ile Ser Ser Leu Gln Pro
65                  70                  75                  80
Glu Asp Phe Ala Thr Tyr Tyr Cys Gln Gln Ala Asn Ser Phe Pro Arg
                85                  90                  95
Thr Phe Gly Gln Gly Thr Lys Val Glu Ile Lys Arg
            100                 105
```

<210> SEQ ID NO 301
<211> LENGTH: 18
<212> TYPE: DNA
<213> ORGANISM: Artificial Sequence
<220> FEATURE:
<223> OTHER INFORMATION: Synthetic

<400> SEQUENCE: 301

```
cagggtatta gcagctgg                                                  18
```

<210> SEQ ID NO 302
<211> LENGTH: 6
<212> TYPE: PRT
<213> ORGANISM: Artificial Sequence
<220> FEATURE:
<223> OTHER INFORMATION: Synthetic

<400> SEQUENCE: 302

```
Gln Gly Ile Ser Ser Trp
 1               5
```

<210> SEQ ID NO 303
<211> LENGTH: 9
<212> TYPE: DNA
<213> ORGANISM: Artificial Sequence
<210> SEQ ID NO 303
<211> LENGTH: 9
<212> TYPE: DNA
<213> ORGANISM: Artificial Sequence
<220> FEATURE:
<223> OTHER INFORMATION: Synthetic

<400> SEQUENCE: 303 gctgcatcc                                                                 9

<210> SEQ ID NO 304
<211> LENGTH: 3
<212> TYPE: PRT
<213> ORGANISM: Artificial Sequence
<220> FEATURE:
<223> OTHER INFORMATION: Synthetic

<400> SEQUENCE: 304

Ala Ala Ser
 1

<210> SEQ ID NO 305
<211> LENGTH: 27
<212> TYPE: DNA
<213> ORGANISM: Artificial Sequence
<220> FEATURE:
<223> OTHER INFORMATION: Synthetic

<400> SEQUENCE: 305
caacaggcta acagtttccc tcggacg                                            27

<210> SEQ ID NO 306
<211> LENGTH: 9
<212> TYPE: PRT
<213> ORGANISM: Artificial Sequence
<220> FEATURE:
<223> OTHER INFORMATION: Synthetic

<400> SEQUENCE: 306

Gln Gln Ala Asn Ser Phe Pro Arg Thr
 1               5

<210> SEQ ID NO 307
<211> LENGTH: 360
<212> TYPE: DNA
<213> ORGANISM: Artificial Sequence
<220> FEATURE:
<223> OTHER INFORMATION: Synthetic

<400> SEQUENCE: 307
caggtgcagc tggtggagtc tgggggaggc gtggtccagc ctggggaggtc cctgagactc        60 tcctgtgcag cgtctggatt caccttcagt aattatggca tgcactgggt ccgccaggct       120
ccaggcaagg ggctggagtg ggtggcagtt atttggtatg atgaaagtag taaatactat       180
acagactccg tgaagggccg attcaccatc tccagagaca attcccagaa cacgctgtat       240
ctgcaaatga ccagcctgag agccgaggac acggctgtgt attactgtgc gagagatcgc       300
tggacctact cccactactt tgaatattgg ggccagggaa ccctggtcac tgtctcctca       360

<210> SEQ ID NO 308
<211> LENGTH: 120
<212> TYPE: PRT
<213> ORGANISM: Artificial Sequence
<220> FEATURE:
<223> OTHER INFORMATION: Synthetic

<400> SEQUENCE: 308

Gln Val Gln Leu Val Glu Ser Gly Gly Gly Val Val Gln Pro Gly Arg
 1               5                  10                  15

```
Ser Leu Arg Leu Ser Cys Ala Ala Ser Gly Phe Thr Phe Ser Asn Tyr
            20                  25                  30

Gly Met His Trp Val Arg Gln Ala Pro Gly Lys Gly Leu Glu Trp Val
        35                  40                  45

Ala Val Ile Trp Tyr Asp Glu Ser Ser Lys Tyr Tyr Thr Asp Ser Val
    50                  55                  60

Lys Gly Arg Phe Thr Ile Ser Arg Asp Asn Ser Gln Asn Thr Leu Tyr
65                  70                  75                  80

Leu Gln Met Thr Ser Leu Arg Ala Glu Asp Thr Ala Val Tyr Tyr Cys
                85                  90                  95

Ala Arg Asp Arg Trp Thr Tyr Ser His Tyr Phe Glu Tyr Trp Gly Gln
            100                 105                 110

Gly Thr Leu Val Thr Val Ser Ser
        115                 120
```

<210> SEQ ID NO 309
<211> LENGTH: 321
<212> TYPE: DNA
<213> ORGANISM: Artificial Sequence
<220> FEATURE:
<223> OTHER INFORMATION: Synthetic

<400> SEQUENCE: 309

```
gacatccaga tgacccagtc tccatcttcc gtgtctgcat ctgtaggaga cagagtcacc    60
atcacttgtc gggcgagtca gggtattagc agctgggtag cctggtatca gcagaaacca   120
gggaaagccc ctaaactcct gatctatgct gcatccagtt tgcaaagtgg ggtcccatct   180
aggttcagcg gcagtggatc tgggacagat ttcactctca ccatcagcag cctgcagcct   240
gaagattttg caacttacta ttgtcaacag gctaacagtt tccctcggac gttcggccaa   300
gggaccaagg tggagatcaa a                                             321
```

<210> SEQ ID NO 310
<211> LENGTH: 107
<212> TYPE: PRT
<213> ORGANISM: Artificial Sequence
<220> FEATURE:
<223> OTHER INFORMATION: Synthetic

<400> SEQUENCE: 310

```
Asp Ile Gln Met Thr Gln Ser Pro Ser Ser Val Ser Ala Ser Val Gly
1               5                   10                  15

Asp Arg Val Thr Ile Thr Cys Arg Ala Ser Gln Gly Ile Ser Ser Trp
            20                  25                  30

Val Ala Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ala Asn Ser Phe Pro Arg
                85                  90                  95

Thr Phe Gly Gln Gly Thr Lys Val Glu Ile Lys
            100                 105
```

<210> SEQ ID NO 311
<211> LENGTH: 360
<212> TYPE: DNA

<213> ORGANISM: Artificial Sequence
<220> FEATURE:
<223> OTHER INFORMATION: Synthetic

<400> SEQUENCE: 311

```
caggtgcagc tggtggagtc tgggggaggc gtggtccagc ctggggaggtc cctgagactc    60 tcctgtgcag cgtctggatt caccttcagt aactatggca tgcactgggt ccgccaggct   120
ccaggcaagg ggctggagtg ggtggcagtt atttggtatg atgaaagtag taaacactat   180
gcagactccg tgaagggccg attcaccatc tccagagaca attcccagaa cacgctgtat   240
ctgcaaatga ccagcctgag agccgaggac acggctgtgt attactgtgc gagagatcgc   300
tggacctact cccactactt tgaatattgg ggccaggaa ccctggtcac cgtctcctca    360
```

<210> SEQ ID NO 312
<211> LENGTH: 120
<212> TYPE: PRT
<213> ORGANISM: Artificial Sequence
<220> FEATURE:
<223> OTHER INFORMATION: Synthetic

<400> SEQUENCE: 312

```
Gln Val Gln Leu Val Glu Ser Gly Gly Gly Val Val Gln Pro Gly Arg
 1               5                  10                  15

Ser Leu Arg Leu Ser Cys Ala Ala Ser Gly Phe Thr Phe Ser Asn Tyr
            20                  25                  30

Gly Met His Trp Val Arg Gln Ala Pro Gly Lys Gly Leu Glu Trp Val
        35                  40                  45

Ala Val Ile Trp Tyr Asp Glu Ser Ser Lys His Tyr Ala Asp Ser Val
    50                  55                  60

Lys Gly Arg Phe Thr Ile Ser Arg Asp Asn Ser Gln Asn Thr Leu Tyr
65                  70                  75                  80

Leu Gln Met Thr Ser Leu Arg Ala Glu Asp Thr Ala Val Tyr Tyr Cys
                85                  90                  95

Ala Arg Asp Arg Trp Thr Tyr Ser His Tyr Phe Glu Tyr Trp Gly Gln
            100                 105                 110

Gly Thr Leu Val Thr Val Ser Ser
        115                 120
```

<210> SEQ ID NO 313
<211> LENGTH: 24
<212> TYPE: DNA
<213> ORGANISM: Artificial Sequence
<220> FEATURE:
<223> OTHER INFORMATION: Synthetic

<400> SEQUENCE: 313

```
ggattcacct tcagtaacta tggc                                            24
```

<210> SEQ ID NO 314
<211> LENGTH: 8
<212> TYPE: PRT
<213> ORGANISM: Artificial Sequence
<220> FEATURE:
<223> OTHER INFORMATION: Synthetic

<400> SEQUENCE: 314

```
Gly Phe Thr Phe Ser Asn Tyr Gly
 1               5
```

<210> SEQ ID NO 315

```
<211> LENGTH: 24
<212> TYPE: DNA
<213> ORGANISM: Artificial Sequence
<220> FEATURE:
<223> OTHER INFORMATION: Synthetic

<400> SEQUENCE: 315
atttggtatg atgaaagtag taaa                                            24

<210> SEQ ID NO 316
<211> LENGTH: 8
<212> TYPE: PRT
<213> ORGANISM: Artificial Sequence
<220> FEATURE:
<223> OTHER INFORMATION: Synthetic

<400> SEQUENCE: 316

Ile Trp Tyr Asp Glu Ser Ser Lys
 1               5

<210> SEQ ID NO 317
<211> LENGTH: 39
<212> TYPE: DNA
<213> ORGANISM: Artificial Sequence
<220> FEATURE:
<223> OTHER INFORMATION: Synthetic

<400> SEQUENCE: 317
gcgagagatc gctggaccta ctcccactac tttgaatat                            39

<210> SEQ ID NO 318
<211> LENGTH: 13
<212> TYPE: PRT
<213> ORGANISM: Artificial Sequence
<220> FEATURE:
<223> OTHER INFORMATION: Synthetic

<400> SEQUENCE: 318

Ala Arg Asp Arg Trp Thr Tyr Ser His Tyr Phe Glu Tyr
 1               5                  10

<210> SEQ ID NO 319
<211> LENGTH: 324
<212> TYPE: DNA
<213> ORGANISM: Artificial Sequence
<220> FEATURE:
<223> OTHER INFORMATION: Synthetic

<400> SEQUENCE: 319
gacatccaga tgacccagtc tccatcttcc gtgtctgcat ctgtaggaga cagagtcacc     60
atcacttgtc gggcgagtca ggatattagc agctgggtag cctggtatca gcagaaacca    120
gggaaagccc ctaaactcct gatctatgct gcatccagtt tgcaaagtgg ggtcccatct    180
aggttcagcg gcagtggatc tgggacagat tcactctcac catcagcag cctgcagcct    240 gaagattttg caacttacta ttgtcaacag gctaacagtt ccctcggac gttcggccaa    300 gggaccaagg tggagatcaa acga                                           324

<210> SEQ ID NO 320
<211> LENGTH: 108
<212> TYPE: PRT
<213> ORGANISM: Artificial Sequence
<220> FEATURE:
<223> OTHER INFORMATION: Synthetic

<400> SEQUENCE: 320
```

```
Asp Ile Gln Met Thr Gln Ser Pro Ser Ser Val Ser Ala Ser Val Gly
 1               5                  10                  15

Asp Arg Val Thr Ile Thr Cys Arg Ala Ser Gln Asp Ile Ser Ser Trp
            20                  25                  30

Val Ala Trp Tyr Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ala Asn Ser Phe Pro Arg
                85                  90                  95

Thr Phe Gly Gln Gly Thr Lys Val Glu Ile Lys Arg
            100                 105
```

<210> SEQ ID NO 321
<211> LENGTH: 18
<212> TYPE: DNA
<213> ORGANISM: Artificial Sequence
<220> FEATURE:
<223> OTHER INFORMATION: Synthetic

<400> SEQUENCE: 321
caggatatta gcagctgg                                              18

<210> SEQ ID NO 322
<211> LENGTH: 6
<212> TYPE: PRT
<213> ORGANISM: Artificial Sequence
<220> FEATURE:
<223> OTHER INFORMATION: Synthetic

<400> SEQUENCE: 322

```
Gln Asp Ile Ser Ser Trp
 1               5
```

<210> SEQ ID NO 323
<211> LENGTH: 9
<212> TYPE: DNA
<213> ORGANISM: Artificial Sequence
<220> FEATURE:
<223> OTHER INFORMATION: Synthetic

<400> SEQUENCE: 323 gctgcatcc                                                         9

<210> SEQ ID NO 324
<211> LENGTH: 3
<212> TYPE: PRT
<213> ORGANISM: Artificial Sequence
<220> FEATURE:
<223> OTHER INFORMATION: Synthetic

<400> SEQUENCE: 324

```
Ala Ala Ser
 1
```

<210> SEQ ID NO 325
<211> LENGTH: 27
<212> TYPE: DNA
<213> ORGANISM: Artificial Sequence
<220> FEATURE:
<223> OTHER INFORMATION: Synthetic

<400> SEQUENCE: 325
caacaggcta acagtttccc tcggacg    27

<210> SEQ ID NO 326
<211> LENGTH: 9
<212> TYPE: PRT
<213> ORGANISM: Artificial Sequence
<220> FEATURE:
<223> OTHER INFORMATION: Synthetic

<400> SEQUENCE: 326

Gln Gln Ala Asn Ser Phe Pro Arg Thr
1               5

<210> SEQ ID NO 327
<211> LENGTH: 360
<212> TYPE: DNA
<213> ORGANISM: Artificial Sequence
<220> FEATURE:
<223> OTHER INFORMATION: Synthetic

<400> SEQUENCE: 327
caggtgcagc tggtggagtc tgggggaggc gtggtccagc ctggagggtc cctgagactc    60
tcctgtgcag cgtctggatt caccttcagt aactatggca tgcactgggt ccgccaggct    120
ccaggcaagg ggctggagtg gtggcagtt atttggtatg atgaaagtag taaacactat    180
gcagactccg tgaagggccg attcaccatc tccagagaca attccagaa cacgctgtat    240 ctgcaaatga ccagcctgag agccgaggac acggctgtgt attactgtgc gagagatcgc    300
tggacctact cccactactt tgaatattgg ggccagggaa ccctggtcac cgtctcctca    360

<210> SEQ ID NO 328
<211> LENGTH: 120
<212> TYPE: PRT
<213> ORGANISM: Artificial Sequence
<220> FEATURE:
<223> OTHER INFORMATION: Synthetic

<400> SEQUENCE: 328

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Asn Tyr
            20                  25                  30

Gly Met His Trp Val Arg Gln Ala Pro Gly Lys Gly Leu Glu Trp Val
        35                  40                  45

Ala Val Ile Trp Tyr Asp Glu Ser Ser Lys His Tyr Ala Asp Ser Val
    50                  55                  60

Lys Gly Arg Phe Thr Ile Ser Arg Asp Asn Ser Gln Asn Thr Leu Tyr
65                  70                  75                  80

Leu Gln Met Thr Ser Leu Arg Ala Glu Asp Thr Ala Val Tyr Tyr Cys
                85                  90                  95

Ala Arg Asp Arg Trp Thr Tyr Ser His Tyr Phe Glu Tyr Trp Gly Gln
            100                 105                 110

Gly Thr Leu Val Thr Val Ser Ser
        115                 120

<210> SEQ ID NO 329
<211> LENGTH: 321
<212> TYPE: DNA
<213> ORGANISM: Artificial Sequence
<220> FEATURE:
<223> OTHER INFORMATION: Synthetic

<400> SEQUENCE: 329

```
gacatccaga tgacccagtc tccatcttcc gtgtctgcat ctgtaggaga cagagtcacc    60
atcacttgtc gggcgagtca ggatattagc agctgggtag cctggtatca gcagaaacca   120
gggaaagccc ctaaactcct gatctatgct gcatccagtt tgcaaagtgg ggtcccatct   180
aggttcagcg gcagtggatc tgggacagat ttcactctca ccatcagcag cctgcagcct   240
gaagattttg caacttacta ttgtcaacag gctaacagtt ccctcggac gttcggccaa    300
gggaccaagg tggagatcaa a                                             321
```

<210> SEQ ID NO 330
<211> LENGTH: 107
<212> TYPE: PRT
<213> ORGANISM: Artificial Sequence
<220> FEATURE:
<223> OTHER INFORMATION: Synthetic

<400> SEQUENCE: 330

```
Asp Ile Gln Met Thr Gln Ser Pro Ser Ser Val Ser Ala Ser Val Gly
 1               5                  10                  15
Asp Arg Val Thr Ile Thr Cys Arg Ala Ser Gln Asp Ile Ser Ser Trp
            20                  25                  30
Val Ala Trp Tyr Gln Gln Lys Pro Gly Lys Ala Pro Lys Leu Leu Ile
        35                  40                  45
Tyr Ala Ala Ser Leu Gln Ser Gly Val Pro Ser Arg Phe Ser Gly
    50                  55                  60
Ser Gly Ser Gly Thr Asp Phe Thr Leu Thr Ile Ser Ser Leu Gln Pro
65                  70                  75                  80
Glu Asp Phe Ala Thr Tyr Tyr Cys Gln Gln Ala Asn Ser Phe Pro Arg
                85                  90                  95
Thr Phe Gly Gln Gly Thr Lys Val Glu Ile Lys
           100                 105
```

<210> SEQ ID NO 331
<211> LENGTH: 360
<212> TYPE: DNA
<213> ORGANISM: Artificial Sequence
<220> FEATURE:
<223> OTHER INFORMATION: Synthetic

<400> SEQUENCE: 331

```
gaggtgcagc tggtggagtc tgggggaggc gtggtccaac tgggaggtc cctgagactc    60
tcctgtgcag cgtctggatt caccttcagt aactatggca tgcactgggt ccgccaggct   120
ccaggcaagg gactggagtg ggtggcagtt atatggtatg atgatagtaa taaaaattat   180
gcagactccg tgaagggccg attcaccatc tccagagaca attccaagaa cacgctgtat   240
ctgcaaatga acagcctgag agtcgaggac acggctgtgt attactgtgc gagagatcgc   300
tggacctact cccacttctt tgagtactgg ggccagggaa ccctggtcac cgtctcctca   360
```

<210> SEQ ID NO 332
<211> LENGTH: 120
<212> TYPE: PRT
<213> ORGANISM: Artificial Sequence
<220> FEATURE:
<223> OTHER INFORMATION: Synthetic

<400> SEQUENCE: 332

```
Glu Val Gln Leu Val Glu Ser Gly Gly Val Val Gln Pro Gly Arg
 1               5                  10                  15

Ser Leu Arg Leu Ser Cys Ala Ala Ser Gly Phe Thr Phe Ser Asn Tyr
             20                  25                  30

Gly Met His Trp Val Arg Gln Ala Pro Gly Lys Gly Leu Glu Trp Val
             35                  40                  45

Ala Val Ile Trp Tyr Asp Asp Ser Asn Lys Asn Tyr Ala Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Val Glu Asp Thr Ala Val Tyr Tyr Cys
                 85                  90                  95

Ala Arg Asp Arg Trp Thr Tyr Ser His Phe Phe Glu Tyr Trp Gly Gln
            100                 105                 110

Gly Thr Leu Val Thr Val Ser Ser
            115                 120
```

<210> SEQ ID NO 333
<211> LENGTH: 24
<212> TYPE: DNA
<213> ORGANISM: Artificial Sequence
<220> FEATURE:
<223> OTHER INFORMATION: Synthetic

<400> SEQUENCE: 333
ggattcacct tcagtaacta tggc                                            24

<210> SEQ ID NO 334
<211> LENGTH: 8
<212> TYPE: PRT
<213> ORGANISM: Artificial Sequence
<220> FEATURE:
<223> OTHER INFORMATION: Synthetic

<400> SEQUENCE: 334

```
Gly Phe Thr Phe Ser Asn Tyr Gly
 1               5
```

<210> SEQ ID NO 335
<211> LENGTH: 24
<212> TYPE: DNA
<213> ORGANISM: Artificial Sequence
<220> FEATURE:
<223> OTHER INFORMATION: Synthetic

<400> SEQUENCE: 335
atatggtatg atgatagtaa taaa                                            24

<210> SEQ ID NO 336
<211> LENGTH: 8
<212> TYPE: PRT
<213> ORGANISM: Artificial Sequence
<220> FEATURE:
<223> OTHER INFORMATION: Synthetic

<400> SEQUENCE: 336

```
Ile Trp Tyr Asp Asp Ser Asn Lys
 1               5
```

<210> SEQ ID NO 337
<211> LENGTH: 39
<212> TYPE: DNA

```
<213> ORGANISM: Artificial Sequence
<220> FEATURE:
<223> OTHER INFORMATION: Synthetic

<400> SEQUENCE: 337
gcgagagatc gctggaccta ctcccacttc tttgagtac                          39

<210> SEQ ID NO 338
<211> LENGTH: 13
<212> TYPE: PRT
<213> ORGANISM: Artificial Sequence
<220> FEATURE:
<223> OTHER INFORMATION: Synthetic

<400> SEQUENCE: 338

Ala Arg Asp Arg Trp Thr Tyr Ser His Phe Phe Glu Tyr
 1               5                  10

<210> SEQ ID NO 339
<211> LENGTH: 324
<212> TYPE: DNA
<213> ORGANISM: Artificial Sequence
<220> FEATURE:
<223> OTHER INFORMATION: Synthetic

<400> SEQUENCE: 339
gacatccaga tgacccagtc tccatcttcc gtgtctgcat ctgtaggaga cagagtcacc    60
atcacttgtc gggcgagtca gggtattagc agctggttag cctggtatca gcagaaacca   120
gggaaagccc ctaacctcct gatctatgct gcttccagtt tgcaaagtgg ggtcccatca   180
aggttcggcg gcagtggatc tgggacagat ttctctctca ccatcagcgg cctacagcct   240
gaagattttg caacttacta ttgtcagcag gctaacagtt ccctcggac gttcggccaa    300 gggaccaagg tggagatcaa acga                                         324

<210> SEQ ID NO 340
<211> LENGTH: 108
<212> TYPE: PRT
<213> ORGANISM: Artificial Sequence
<220> FEATURE:
<223> OTHER INFORMATION: Synthetic

<400> SEQUENCE: 340

Asp Ile Gln Met Thr Gln Ser Pro Ser Ser Val Ser Ala Ser Val Gly
 1               5                  10                  15

Asp Arg Val Thr Ile Thr Cys Arg Ala Ser Gln Gly Ile Ser Ser Trp
            20                  25                  30

Leu Ala Trp Tyr Gln Gln Lys Pro Gly Lys Ala Pro Asn Leu Leu Ile
        35                  40                  45

Tyr Ala Ala Ser Ser Leu Gln Ser Gly Val Pro Ser Arg Phe Gly Gly
    50                  55                  60

Ser Gly Ser Gly Thr Asp Phe Ser Leu Thr Ile Ser Gly Leu Gln Pro
65                  70                  75                  80

Glu Asp Phe Ala Thr Tyr Tyr Cys Gln Gln Ala Asn Ser Phe Pro Arg
                85                  90                  95

Thr Phe Gly Gln Gly Thr Lys Val Glu Ile Lys Arg
            100                 105

<210> SEQ ID NO 341
<211> LENGTH: 18
<212> TYPE: DNA
<213> ORGANISM: Artificial Sequence
```

<220> FEATURE:
<223> OTHER INFORMATION: Synthetic

<400> SEQUENCE: 341
cagggtatta gcagctgg                                             18

<210> SEQ ID NO 342
<211> LENGTH: 6
<212> TYPE: PRT
<213> ORGANISM: Artificial Sequence
<220> FEATURE:
<223> OTHER INFORMATION: Synthetic

<400> SEQUENCE: 342

Gln Gly Ile Ser Ser Trp
 1               5

<210> SEQ ID NO 343
<211> LENGTH: 9
<212> TYPE: DNA
<213> ORGANISM: Artificial Sequence
<220> FEATURE:
<223> OTHER INFORMATION: Synthetic

<400> SEQUENCE: 343 gctgcttcc                                                        9

<210> SEQ ID NO 344
<211> LENGTH: 3
<212> TYPE: PRT
<213> ORGANISM: Artificial Sequence
<220> FEATURE:
<223> OTHER INFORMATION: Synthetic

<400> SEQUENCE: 344

Ala Ala Ser
 1

<210> SEQ ID NO 345
<211> LENGTH: 27
<212> TYPE: DNA
<213> ORGANISM: Artificial Sequence
<220> FEATURE:
<223> OTHER INFORMATION: Synthetic

<400> SEQUENCE: 345
cagcaggcta acagtttccc tcggacg                                   27

<210> SEQ ID NO 346
<211> LENGTH: 9
<212> TYPE: PRT
<213> ORGANISM: Artificial Sequence
<220> FEATURE:
<223> OTHER INFORMATION: Synthetic

<400> SEQUENCE: 346

Gln Gln Ala Asn Ser Phe Pro Arg Thr
 1               5

<210> SEQ ID NO 347
<211> LENGTH: 360
<212> TYPE: DNA
<213> ORGANISM: Artificial Sequence
<220> FEATURE:
<223> OTHER INFORMATION: Synthetic

<400> SEQUENCE: 347

```
caggtgcagc tggtggagtc tgggggaggc gtggtccaac ctgggaggtc cctgagactc      60
tcctgtgcag cgtctggatt caccttcagt aactatggca tgcactgggt ccgccaggct     120
ccaggcaagg gactggagtg gtggcagtt atatggtatg atgatagtaa taaaaattat     180
gcagactccg tgaagggccg attcaccatc tccagagaca attccaagaa cacgctgtat     240
ctgcaaatga acagcctgag agtcgaggac acggctgtgt attactgtgc gagagatcgc     300
tggacctact cccacttctt tgagtactgg ggccagggaa ccctggtcac cgtctcctca     360
```

<210> SEQ ID NO 348
<211> LENGTH: 120
<212> TYPE: PRT
<213> ORGANISM: Artificial Sequence
<220> FEATURE:
<223> OTHER INFORMATION: Synthetic

<400> SEQUENCE: 348

```
Gln Val Gln Leu Val Glu Ser Gly Gly Gly Val Val Gln Pro Gly Arg
  1               5                  10                  15

Ser Leu Arg Leu Ser Cys Ala Ala Ser Gly Phe Thr Phe Ser Asn Tyr
             20                  25                  30

Gly Met His Trp Val Arg Gln Ala Pro Gly Lys Gly Leu Glu Trp Val
         35                  40                  45

Ala Val Ile Trp Tyr Asp Asp Ser Asn Lys Asn Tyr Ala Asp Ser Val
     50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Val Glu Asp Thr Ala Val Tyr Tyr Cys
                 85                  90                  95

Ala Arg Asp Arg Trp Thr Tyr Ser His Phe Phe Glu Tyr Trp Gly Gln
            100                 105                 110

Gly Thr Leu Val Thr Val Ser Ser
        115                 120
```

<210> SEQ ID NO 349
<211> LENGTH: 321
<212> TYPE: DNA
<213> ORGANISM: Artificial Sequence
<220> FEATURE:
<223> OTHER INFORMATION: Synthetic

<400> SEQUENCE: 349

```
gacatccaga tgacccagtc tccatcttcc gtgtctgcat ctgtaggaga cagagtcacc      60
atcacttgtc gggcgagtca gggtattagc agctggttag cctggtatca gcagaaacca     120
gggaaagccc ctaacctcct gatctatgct gcttccagtt tgcaaagtgg ggtcccatca     180
aggttcggcg gcagtggatc tgggacagat ttctctctca ccatcagcgg cctacagcct     240
gaagattttg caacttacta ttgtcagcag gctaacagtt ccctcggac gttcggccaa     300 gggaccaagg tggagatcaa a                                                321
```

<210> SEQ ID NO 350
<211> LENGTH: 107
<212> TYPE: PRT
<213> ORGANISM: Artificial Sequence
<220> FEATURE:
<223> OTHER INFORMATION: Synthetic

<400> SEQUENCE: 350

```
Asp Ile Gln Met Thr Gln Ser Pro Ser Ser Val Ser Ala Ser Val Gly
 1               5                  10                  15

Asp Arg Val Thr Ile Thr Cys Arg Ala Ser Gln Gly Ile Ser Ser Trp
             20                  25                  30

Leu Ala Trp Tyr Gln Gln Lys Pro Gly Lys Ala Pro Asn Leu Leu Ile
         35                  40                  45

Tyr Ala Ala Ser Ser Leu Gln Ser Gly Val Pro Ser Arg Phe Gly Gly
 50                  55                  60

Ser Gly Ser Gly Thr Asp Phe Ser Leu Thr Ile Ser Gly Leu Gln Pro
 65                  70                  75                  80

Glu Asp Phe Ala Thr Tyr Tyr Cys Gln Gln Ala Asn Ser Phe Pro Arg
             85                  90                  95

Thr Phe Gly Gln Gly Thr Lys Val Glu Ile Lys
            100                 105
```

<210> SEQ ID NO 351
<211> LENGTH: 354
<212> TYPE: DNA
<213> ORGANISM: Artificial Sequence
<220> FEATURE:
<223> OTHER INFORMATION: Synthetic

<400> SEQUENCE: 351

```
gaggtgcagc tggtggagtc tgggggaggc ttggtacacc ctgggggtc cctgagactc    60 tcctgtgcag cctctggatt cacctttggc ggctatgcca tgagctgggt ccgccaggct   120
ccagggaagg gcctggagtg gtctcactt attagtggta gtggtggtag cacatactac   180
gcagactccg tgaagggccg gttcaccatt tttagagaca attccaagaa cacgctgtat   240
ctgcaaatga tcagcctgag agccgaggat tcggccgtat attactgtgc gaaatacagt   300
aactatgact acttcgaccc ctggggccag ggaaccctgg tcactgtctc ctca         354
```

<210> SEQ ID NO 352
<211> LENGTH: 118
<212> TYPE: PRT
<213> ORGANISM: Artificial Sequence
<220> FEATURE:
<223> OTHER INFORMATION: Synthetic

<400> SEQUENCE: 352

```
Glu Val Gln Leu Val Glu Ser Gly Gly Gly Leu Val His Pro Gly Gly
 1               5                  10                  15

Ser Leu Arg Leu Ser Cys Ala Ala Ser Gly Phe Thr Phe Gly Gly Tyr
             20                  25                  30

Ala Met Ser Trp Val Arg Gln Ala Pro Gly Lys Gly Leu Glu Trp Val
         35                  40                  45

Ser Leu Ile Ser Gly Ser Gly Gly Ser Thr Tyr Tyr Ala Asp Ser Val
 50                  55                  60

Lys Gly Arg Phe Thr Ile Phe Arg Asp Asn Ser Lys Asn Thr Leu Tyr
 65                  70                  75                  80

Leu Gln Met Ile Ser Leu Arg Ala Glu Asp Ser Ala Val Tyr Tyr Cys
             85                  90                  95

Ala Lys Tyr Ser Asn Tyr Asp Tyr Phe Asp Pro Trp Gly Gln Gly Thr
            100                 105                 110

Leu Val Thr Val Ser Ser
        115
```

<210> SEQ ID NO 353

```
<211> LENGTH: 24
<212> TYPE: DNA
<213> ORGANISM: Artificial Sequence
<220> FEATURE:
<223> OTHER INFORMATION: Synthetic

<400> SEQUENCE: 353
ggattcacct ttggcggcta tgcc                                          24

<210> SEQ ID NO 354
<211> LENGTH: 8
<212> TYPE: PRT
<213> ORGANISM: Artificial Sequence
<220> FEATURE:
<223> OTHER INFORMATION: Synthetic

<400> SEQUENCE: 354

Gly Phe Thr Phe Gly Gly Tyr Ala
 1               5

<210> SEQ ID NO 355
<211> LENGTH: 24
<212> TYPE: DNA
<213> ORGANISM: Artificial Sequence
<220> FEATURE:
<223> OTHER INFORMATION: Synthetic

<400> SEQUENCE: 355
attagtggta gtggtggtag caca                                          24

<210> SEQ ID NO 356
<211> LENGTH: 8
<212> TYPE: PRT
<213> ORGANISM: Artificial Sequence
<220> FEATURE:
<223> OTHER INFORMATION: Synthetic

<400> SEQUENCE: 356

Ile Ser Gly Ser Gly Gly Ser Thr
 1               5

<210> SEQ ID NO 357
<211> LENGTH: 33
<212> TYPE: DNA
<213> ORGANISM: Artificial Sequence
<220> FEATURE:
<223> OTHER INFORMATION: Synthetic

<400> SEQUENCE: 357
gcgaaataca gtaactatga ctacttcgac ccc                                33

<210> SEQ ID NO 358
<211> LENGTH: 11
<212> TYPE: PRT
<213> ORGANISM: Artificial Sequence
<220> FEATURE:
<223> OTHER INFORMATION: Synthetic

<400> SEQUENCE: 358

Ala Lys Tyr Ser Asn Tyr Asp Tyr Phe Asp Pro
 1               5                  10

<210> SEQ ID NO 359
<211> LENGTH: 327
<212> TYPE: DNA
<213> ORGANISM: Artificial Sequence
<220> FEATURE:
```

<223> OTHER INFORMATION: Synthetic

<400> SEQUENCE: 359

```
gaaattgtgt tgacacagtc tccaggcacc ctgtctttgt ctccagggga aagagtcacc      60
ctctcctgca gggccagtca gagtgttagc agcagctact tagcctggta ccagcagaaa     120
cctggccagg ctcccaggct cctcatctat ggtgcatcca gcagggccac tggcatccca     180
gacaggttca gtggcagtgg gtctgggaca gacttcactc tcaccatcag cagactggag     240
cctgaagatt ttgcagtgta ttactgtcag cagtatggta gctcacctcg gacgttcggc     300
caagggacca aggtggagat caaacga                                         327
```

<210> SEQ ID NO 360
<211> LENGTH: 109
<212> TYPE: PRT
<213> ORGANISM: Artificial Sequence
<220> FEATURE:
<223> OTHER INFORMATION: Synthetic

<400> SEQUENCE: 360

```
Glu Ile Val Leu Thr Gln Ser Pro Gly Thr Leu Ser Leu Ser Pro Gly
 1               5                  10                  15
Glu Arg Val Thr Leu Ser Cys Arg Ala Ser Gln Ser Val Ser Ser Ser
            20                  25                  30
Tyr Leu Ala Trp Tyr Gln Gln Lys Pro Gly Gln Ala Pro Arg Leu Leu
        35                  40                  45
Ile Tyr Gly Ala Ser Ser Arg Ala Thr Gly Ile Pro Asp Arg Phe Ser
    50                  55                  60
Gly Ser Gly Ser Gly Thr Asp Phe Thr Leu Thr Ile Ser Arg Leu Glu
65                  70                  75                  80
Pro Glu Asp Phe Ala Val Tyr Tyr Cys Gln Gln Tyr Gly Ser Ser Pro
                85                  90                  95
Arg Thr Phe Gly Gln Gly Thr Lys Val Glu Ile Lys Arg
            100                 105
```

<210> SEQ ID NO 361
<211> LENGTH: 21
<212> TYPE: DNA
<213> ORGANISM: Artificial Sequence
<220> FEATURE:
<223> OTHER INFORMATION: Synthetic

<400> SEQUENCE: 361

```
cagagtgtta gcagcagcta c                                                21
```

<210> SEQ ID NO 362
<211> LENGTH: 7
<212> TYPE: PRT
<213> ORGANISM: Artificial Sequence
<220> FEATURE:
<223> OTHER INFORMATION: Synthetic

<400> SEQUENCE: 362

```
Gln Ser Val Ser Ser Ser Tyr
 1               5
```

<210> SEQ ID NO 363
<211> LENGTH: 9
<212> TYPE: DNA
<213> ORGANISM: Artificial Sequence
<220> FEATURE:
<223> OTHER INFORMATION: Synthetic

<400> SEQUENCE: 363 ggtgcatcc                                                                  9

<210> SEQ ID NO 364
<211> LENGTH: 3
<212> TYPE: PRT
<213> ORGANISM: Artificial Sequence
<220> FEATURE:
<223> OTHER INFORMATION: Synthetic

<400> SEQUENCE: 364

Gly Ala Ser
 1

<210> SEQ ID NO 365
<211> LENGTH: 27
<212> TYPE: DNA
<213> ORGANISM: Artificial Sequence
<220> FEATURE:
<223> OTHER INFORMATION: Synthetic

<400> SEQUENCE: 365
cagcagtatg gtagctcacc tcggacg                                              27

<210> SEQ ID NO 366
<211> LENGTH: 9
<212> TYPE: PRT
<213> ORGANISM: Artificial Sequence
<220> FEATURE:
<223> OTHER INFORMATION: Synthetic

<400> SEQUENCE: 366

Gln Gln Tyr Gly Ser Ser Pro Arg Thr
 1               5

<210> SEQ ID NO 367
<211> LENGTH: 354
<212> TYPE: DNA
<213> ORGANISM: Artificial Sequence
<220> FEATURE:
<223> OTHER INFORMATION: Synthetic

<400> SEQUENCE: 367
gaggtgcagc tgttggagtc tgggggaggc ttggtacacc ctggggggtc cctgagactc         60
tcctgtgcag cctctggatt cacctttggc ggctatgcca tgagctgggt ccgccaggct        120
ccagggaagg gcctggagtg ggtctcactt attagtggta gtggtggtag cacatactac        180
gcagactccg tgaagggccg gttcaccatt tttagagaca attccaagaa cacgctgtat        240
ctgcaaatga tcagcctgag agccgaggat tcggccgtat attactgtgc gaaatacagt        300
aactatgact acttcgaccc ctggggccag ggaaccctgg tcactgtctc ctca              354

<210> SEQ ID NO 368
<211> LENGTH: 118
<212> TYPE: PRT
<213> ORGANISM: Artificial Sequence
<220> FEATURE:
<223> OTHER INFORMATION: Synthetic

<400> SEQUENCE: 368

Glu Val Gln Leu Leu Glu Ser Gly Gly Gly Leu Val His Pro Gly Gly
 1               5                  10                  15

Ser Leu Arg Leu Ser Cys Ala Ala Ser Gly Phe Thr Phe Gly Gly Tyr

```
            20                  25                  30
Ala Met Ser Trp Val Arg Gln Ala Pro Gly Lys Gly Leu Glu Trp Val
         35                  40                  45

Ser Leu Ile Ser Gly Ser Gly Gly Ser Thr Tyr Tyr Ala Asp Ser Val
     50                  55                  60

Lys Gly Arg Phe Thr Ile Phe Arg Asp Asn Ser Lys Asn Thr Leu Tyr
 65                  70                  75                  80

Leu Gln Met Ile Ser Leu Arg Ala Glu Asp Ser Ala Val Tyr Tyr Cys
                 85                  90                  95

Ala Lys Tyr Ser Asn Tyr Asp Tyr Phe Asp Pro Trp Gly Gln Gly Thr
            100                 105                 110

Leu Val Thr Val Ser Ser
            115
```

<210> SEQ ID NO 369
<211> LENGTH: 324
<212> TYPE: DNA
<213> ORGANISM: Artificial Sequence
<220> FEATURE:
<223> OTHER INFORMATION: Synthetic

<400> SEQUENCE: 369

```
gaaattgtgt tgacgcagtc tccaggcacc ctgtctttgt ctccagggga aagagtcacc        60
ctctcctgca gggccagtca gagtgttagc agcagctact tagcctggta ccagcagaaa       120
cctggccagg ctcccaggct cctcatctat ggtgcatcca gcagggccac tggcatccca       180
gacaggttca gtggcagtgg gtctgggaca gacttcactc tcaccatcag cagactggag       240
cctgaagatt ttgcagtgta ttactgtcag cagtatggta gctcacctcg gacgttcggc       300
caagggacca aggtggagat caaa                                              324
```

<210> SEQ ID NO 370
<211> LENGTH: 108
<212> TYPE: PRT
<213> ORGANISM: Artificial Sequence
<220> FEATURE:
<223> OTHER INFORMATION: Synthetic

<400> SEQUENCE: 370

```
Glu Ile Val Leu Thr Gln Ser Pro Gly Thr Leu Ser Leu Ser Pro Gly
 1               5                  10                  15

Glu Arg Val Thr Leu Ser Cys Arg Ala Ser Gln Ser Val Ser Ser Ser
             20                  25                  30

Tyr Leu Ala Trp Tyr Gln Gln Lys Pro Gly Gln Ala Pro Arg Leu Leu
         35                  40                  45

Ile Tyr Gly Ala Ser Ser Arg Ala Thr Gly Ile Pro Asp Arg Phe Ser
     50                  55                  60

Gly Ser Gly Ser Gly Thr Asp Phe Thr Leu Thr Ile Ser Arg Leu Glu
 65                  70                  75                  80

Pro Glu Asp Phe Ala Val Tyr Tyr Cys Gln Gln Tyr Gly Ser Ser Pro
                 85                  90                  95

Arg Thr Phe Gly Gln Gly Thr Lys Val Glu Ile Lys
            100                 105
```

<210> SEQ ID NO 371
<211> LENGTH: 324
<212> TYPE: DNA
<213> ORGANISM: Artificial Sequence
<220> FEATURE:

<223> OTHER INFORMATION: Synthetic

<400> SEQUENCE: 371

```
gaaattgtgt tgacacagtc tccaggcacc ctgtctttgt ctccagggga aagagtcacc    60
ctctcctgca gggccagtca gagtgttagc agcagctact tagcctggta ccagcagaaa   120
cctggccagg ctcccaggct cctcatctat ggtgcatcca gcagggccac tggcatccca   180
gacaggttca gtggcagtgg gtctgggaca gacttcactc tcaccatcag cagactggag   240
cctgaagatt ttgcaatgta ttactgtcag cagtatggta gctcacctcg gacgttcggc   300
caagggacca aggtggaaat caaa                                           324
```

<210> SEQ ID NO 372
<211> LENGTH: 108
<212> TYPE: PRT
<213> ORGANISM: Artificial Sequence
<220> FEATURE:
<223> OTHER INFORMATION: Synthetic

<400> SEQUENCE: 372

```
Glu Ile Val Leu Thr Gln Ser Pro Gly Thr Leu Ser Leu Ser Pro Gly
 1               5                  10                  15
Glu Arg Val Thr Leu Ser Cys Arg Ala Ser Gln Ser Val Ser Ser Ser
            20                  25                  30
Tyr Leu Ala Trp Tyr Gln Gln Lys Pro Gly Gln Ala Pro Arg Leu Leu
        35                  40                  45
Ile Tyr Gly Ala Ser Ser Arg Ala Thr Gly Ile Pro Asp Arg Phe Ser
    50                  55                  60
Gly Ser Gly Ser Gly Thr Asp Phe Thr Leu Thr Ile Ser Arg Leu Glu
65                  70                  75                  80
Pro Glu Asp Phe Ala Met Tyr Tyr Cys Gln Gln Tyr Gly Ser Ser Pro
                85                  90                  95
Arg Thr Phe Gly Gln Gly Thr Lys Val Glu Ile Lys
            100                 105
```

<210> SEQ ID NO 373
<211> LENGTH: 21
<212> TYPE: DNA
<213> ORGANISM: Artificial Sequence
<220> FEATURE:
<223> OTHER INFORMATION: Synthetic

<400> SEQUENCE: 373

```
cagagtgtta gcagcagcta c                                              21
```

<210> SEQ ID NO 374
<211> LENGTH: 7
<212> TYPE: PRT
<213> ORGANISM: Artificial Sequence
<220> FEATURE:
<223> OTHER INFORMATION: Synthetic

<400> SEQUENCE: 374

```
Gln Ser Val Ser Ser Ser Tyr
 1               5
```

<210> SEQ ID NO 375
<211> LENGTH: 9
<212> TYPE: DNA
<213> ORGANISM: Artificial Sequence
<220> FEATURE:
<223> OTHER INFORMATION: Synthetic

<400> SEQUENCE: 375 ggtgcatcc                                                                       9

<210> SEQ ID NO 376
<211> LENGTH: 3
<212> TYPE: PRT
<213> ORGANISM: Artificial Sequence
<220> FEATURE:
<223> OTHER INFORMATION: Synthetic

<400> SEQUENCE: 376

Gly Ala Ser
 1

<210> SEQ ID NO 377
<211> LENGTH: 27
<212> TYPE: DNA
<213> ORGANISM: Artificial Sequence
<220> FEATURE:
<223> OTHER INFORMATION: Synthetic

<400> SEQUENCE: 377
cagcagtatg gtagctcacc tcggacg                                                  27

<210> SEQ ID NO 378
<211> LENGTH: 9
<212> TYPE: PRT
<213> ORGANISM: Artificial Sequence
<220> FEATURE:
<223> OTHER INFORMATION: Synthetic

<400> SEQUENCE: 378

Gln Gln Tyr Gly Ser Ser Pro Arg Thr
 1               5

<210> SEQ ID NO 379
<211> LENGTH: 324
<212> TYPE: DNA
<213> ORGANISM: Artificial Sequence
<220> FEATURE:
<223> OTHER INFORMATION: Synthetic

<400> SEQUENCE: 379
gaaattgtgt tgacacagtc tccaggcacc ctgtctttgt ctccagggga aagagtcacc              60
ctctcctgca gggccagtca gagtgttagc agcagctact tagcctggta ccagcagaaa             120
cctggccagg ctcccaggct cctcatctat ggtgcatcca gcagggccac tggcatccca             180
gacaggttca gtggcagtgg gtctgggaca gacttcactc tcaccatcag cagactggag             240
cctgaagatt ttgcaatgta ttactgtcag cagtatggta gctcacctcg gacgttcggc             300
caagggacca aggtggaaat caaa                                                   324

<210> SEQ ID NO 380
<211> LENGTH: 108
<212> TYPE: PRT
<213> ORGANISM: Artificial Sequence
<220> FEATURE:
<223> OTHER INFORMATION: Synthetic

<400> SEQUENCE: 380

Glu Ile Val Leu Thr Gln Ser Pro Gly Thr Leu Ser Leu Ser Pro Gly
 1               5                  10                  15

Glu Arg Val Thr Leu Ser Cys Arg Ala Ser Gln Ser Val Ser Ser Ser

```
                    20                  25                  30
Tyr Leu Ala Trp Tyr Gln Gln Lys Pro Gly Gln Ala Pro Arg Leu Leu
            35                  40                  45

Ile Tyr Gly Ala Ser Ser Arg Ala Thr Gly Ile Pro Asp Arg Phe Ser
        50                  55                  60

Gly Ser Gly Ser Gly Thr Asp Phe Thr Leu Thr Ile Ser Arg Leu Glu
65                  70                  75                  80

Pro Glu Asp Phe Ala Met Tyr Tyr Cys Gln Gln Tyr Gly Ser Ser Pro
                85                  90                  95

Arg Thr Phe Gly Gln Gly Thr Lys Val Glu Ile Lys
            100                 105

<210> SEQ ID NO 381
<211> LENGTH: 8
<212> TYPE: PRT
<213> ORGANISM: Artificial Sequence
<220> FEATURE:
<223> OTHER INFORMATION: Synthetic
<220> FEATURE:
<221> NAME/KEY: VARIANT
<222> LOCATION: (7)...(7)
<223> OTHER INFORMATION: Xaa = Ser or Asn

<400> SEQUENCE: 381

Ile Trp Tyr Asp Asp Ser Xaa Lys
1               5

<210> SEQ ID NO 382
<211> LENGTH: 13
<212> TYPE: PRT
<213> ORGANISM: Artificial Sequence
<220> FEATURE:
<223> OTHER INFORMATION: Synthetic
<220> FEATURE:
<221> NAME/KEY: VARIANT
<222> LOCATION: (10)...(10)
<223> OTHER INFORMATION: Xaa = Tyr or Phe

<400> SEQUENCE: 382

Ala Arg Asp Arg Trp Thr Tyr Ser His Xaa Phe Glu Tyr
1               5                   10

<210> SEQ ID NO 383
<211> LENGTH: 6
<212> TYPE: PRT
<213> ORGANISM: Artificial Sequence
<220> FEATURE:
<223> OTHER INFORMATION: Synthetic
<220> FEATURE:
<221> NAME/KEY: VARIANT
<222> LOCATION: (2)...(2)
<223> OTHER INFORMATION: Xaa = Asp or Gly

<400> SEQUENCE: 383

Gln Xaa Ile Ser Ser Trp
1               5

<210> SEQ ID NO 384
<211> LENGTH: 243
<212> TYPE: PRT
<213> ORGANISM: Homo sapiens

<400> SEQUENCE: 384

Met Cys Ser Arg Gly Trp Asp Ser Cys Leu Ala Leu Glu Leu Leu Leu
1               5                   10                  15
```

Leu Pro Leu Ser Leu Val Thr Ser Ile Gln Gly His Leu Val His
            20                  25                  30

Met Thr Val Val Ser Gly Ser Asn Val Thr Leu Asn Ile Ser Glu Ser
        35                  40                  45

Leu Pro Glu Asn Tyr Lys Gln Leu Thr Trp Phe Tyr Thr Phe Asp Gln
50                  55                  60

Lys Ile Val Glu Trp Asp Ser Arg Lys Ser Lys Tyr Phe Glu Ser Lys
65                  70                  75                  80

Phe Lys Gly Arg Val Arg Leu Asp Pro Gln Ser Gly Ala Leu Tyr Ile
                85                  90                  95

Ser Lys Val Gln Lys Glu Asp Asn Ser Thr Tyr Ile Met Arg Val Leu
            100                 105                 110

Lys Lys Thr Gly Asn Glu Gln Glu Trp Lys Ile Lys Leu Gln Val Leu
        115                 120                 125

Asp Pro Val Pro Lys Pro Val Ile Lys Ile Glu Lys Ile Glu Asp Met
130                 135                 140

Asp Asp Asn Cys Tyr Leu Lys Leu Ser Cys Val Ile Pro Gly Glu Ser
145                 150                 155                 160

Val Asn Tyr Thr Trp Tyr Gly Asp Lys Arg Pro Phe Pro Lys Glu Leu
                165                 170                 175

Gln Asn Ser Val Leu Glu Thr Thr Leu Met Pro His Asn Tyr Ser Arg
            180                 185                 190

Cys Tyr Thr Cys Gln Val Ser Asn Ser Val Ser Lys Asn Gly Thr
        195                 200                 205

Val Cys Leu Ser Pro Pro Cys Thr Leu Ala Arg Ser Phe Gly Val Glu
210                 215                 220

Trp Ile Ala Ser Trp Leu Val Val Thr Val Pro Thr Ile Leu Gly Leu
225                 230                 235                 240

Leu Leu Thr

<210> SEQ ID NO 385
<211> LENGTH: 222
<212> TYPE: PRT
<213> ORGANISM: Artificial Sequence
<220> FEATURE:
<223> OTHER INFORMATION: Synthetic

<400> SEQUENCE: 385

Gln Gly His Leu Val His Met Thr Val Val Ser Gly Ser Asn Val Thr
1               5                   10                  15

Leu Asn Ile Ser Glu Ser Leu Pro Glu Asn Tyr Lys Gln Leu Thr Trp
            20                  25                  30

Phe Tyr Thr Phe Asp Gln Lys Ile Val Glu Trp Asp Ser Arg Lys Ser
        35                  40                  45

Lys Tyr Phe Glu Ser Lys Phe Lys Gly Arg Val Arg Leu Asp Pro Gln
    50                  55                  60

Ser Gly Ala Leu Tyr Ile Ser Lys Val Gln Lys Glu Asp Asn Ser Thr
65                  70                  75                  80

Tyr Ile Met Arg Val Leu Lys Lys Thr Gly Asn Glu Gln Glu Trp Lys
                85                  90                  95

Ile Lys Leu Gln Val Leu Asp Pro Val Pro Lys Pro Val Ile Lys Ile
            100                 105                 110

Glu Lys Ile Glu Asp Met Asp Asp Asn Cys Tyr Leu Lys Leu Ser Cys
        115                 120                 125

Val Ile Pro Gly Glu Ser Val Asn Tyr Thr Trp Tyr Gly Asp Lys Arg

```
                130                 135                 140
Pro Phe Pro Lys Glu Leu Gln Asn Ser Val Leu Glu Thr Thr Leu Met
145                 150                 155                 160

Pro His Asn Tyr Ser Arg Cys Tyr Thr Cys Gln Val Ser Asn Ser Val
                165                 170                 175

Ser Ser Lys Asn Gly Thr Val Cys Leu Ser Pro Pro Cys Thr Leu Ala
                180                 185                 190

Arg Ser Glu Gln Lys Leu Ile Ser Glu Glu Asp Leu Gly Gly Glu Gln
                195                 200                 205

Lys Leu Ile Ser Glu Glu Asp Leu His His His His His
    210                 215                 220
```

<210> SEQ ID NO 386
<211> LENGTH: 218
<212> TYPE: PRT
<213> ORGANISM: Artificial Sequence
<220> FEATURE:
<223> OTHER INFORMATION: Synthetic

<400> SEQUENCE: 386

```
Gly Arg Leu Val His Met Thr Val Val Ser Gly Ser Asn Val Thr Leu
1               5                   10                  15

Asn Ile Ser Glu Ser Leu Pro Glu Asn Tyr Lys Gln Leu Thr Trp Phe
                20                  25                  30

Tyr Thr Phe Asp Gln Lys Ile Val Glu Trp Asp Ser Gly Lys Ser Lys
                35                  40                  45

Tyr Phe Glu Ser Lys Phe Lys Gly Arg Val Arg Leu Asp Pro Gln Ser
    50                  55                  60

Gly Ala Leu Tyr Ile Ser Lys Val Gln Lys Glu Asp Asn Ser Thr Tyr
65                  70                  75                  80

Val Met Arg Val Leu Lys Lys Asp Gly Tyr Glu Gln Glu Trp Lys Ile
                85                  90                  95

Lys Leu Gln Val Leu Asp Pro Val Pro Lys Pro Val Ile Lys Ile Glu
                100                 105                 110

Lys Arg Glu Asp Val Asp Asp Asn Cys Tyr Leu Lys Leu Ser Cys Val
                115                 120                 125

Ile Pro Gly Glu Ser Val Asn Tyr Thr Trp Tyr Gly Glu Leu Pro Lys
    130                 135                 140

Glu Ile Gln Asn Ser Val Leu Glu Thr Thr Leu Lys Pro His Lys His
145                 150                 155                 160

Ser Arg Cys Tyr Thr Cys Gln Val Ser Asn Ser Val Ser Ser Lys Asn
                165                 170                 175

Gly Thr Phe Cys Phe Ser Pro Pro Cys Thr Ala Ala Arg Ser Glu Gln
                180                 185                 190

Lys Leu Ile Ser Glu Glu Asp Leu Gly Gly Glu Gln Lys Leu Ile Ser
                195                 200                 205

Glu Glu Asp Leu His His His His His
    210                 215
```

<210> SEQ ID NO 387
<211> LENGTH: 427
<212> TYPE: PRT
<213> ORGANISM: Artificial Sequence
<220> FEATURE:
<223> OTHER INFORMATION: Synthetic

<400> SEQUENCE: 387

-continued

```
Gln Gly His Leu Val His Met Thr Val Val Ser Gly Ser Asn Val Thr
 1               5                  10                  15

Leu Asn Ile Ser Glu Ser Leu Pro Glu Asn Tyr Lys Gln Leu Thr Trp
             20                  25                  30

Phe Tyr Thr Phe Asp Gln Lys Ile Val Glu Trp Asp Ser Arg Lys Ser
         35                  40                  45

Lys Tyr Phe Glu Ser Lys Phe Lys Gly Arg Val Arg Leu Asp Pro Gln
 50                  55                  60

Ser Gly Ala Leu Tyr Ile Ser Lys Val Gln Lys Glu Asp Asn Ser Thr
 65                  70                  75                  80

Tyr Ile Met Arg Val Leu Lys Lys Thr Gly Asn Glu Gln Glu Trp Lys
                 85                  90                  95

Ile Lys Leu Gln Val Leu Asp Pro Val Pro Lys Pro Val Ile Lys Ile
            100                 105                 110

Glu Lys Ile Glu Asp Met Asp Asp Asn Cys Tyr Leu Lys Leu Ser Cys
        115                 120                 125

Val Ile Pro Gly Glu Ser Val Asn Tyr Thr Trp Tyr Gly Asp Lys Arg
    130                 135                 140

Pro Phe Pro Lys Glu Leu Gln Asn Ser Val Leu Glu Thr Thr Leu Met
145                 150                 155                 160

Pro His Asn Tyr Ser Arg Cys Tyr Thr Cys Gln Val Ser Asn Ser Val
                165                 170                 175

Ser Ser Lys Asn Gly Thr Val Cys Leu Ser Pro Cys Thr Leu Ala
            180                 185                 190

Arg Ser Glu Pro Arg Gly Pro Thr Ile Lys Pro Cys Pro Pro Cys Lys
        195                 200                 205

Cys Pro Ala Pro Asn Leu Leu Gly Gly Pro Ser Val Phe Ile Phe Pro
    210                 215                 220

Pro Lys Ile Lys Asp Val Leu Met Ile Ser Leu Ser Pro Ile Val Thr
225                 230                 235                 240

Cys Val Val Val Asp Val Ser Glu Asp Asp Pro Asp Val Gln Ile Ser
                245                 250                 255

Trp Phe Val Asn Asn Val Glu Val His Thr Ala Gln Thr Gln Thr His
            260                 265                 270

Arg Glu Asp Tyr Asn Ser Thr Leu Arg Val Val Ser Ala Leu Pro Ile
        275                 280                 285

Gln His Gln Asp Trp Met Ser Gly Lys Glu Phe Lys Cys Lys Val Asn
    290                 295                 300

Asn Lys Asp Leu Pro Ala Pro Ile Glu Arg Thr Ile Ser Lys Pro Lys
305                 310                 315                 320

Gly Ser Val Arg Ala Pro Gln Val Tyr Val Leu Pro Pro Glu Glu
                325                 330                 335

Glu Met Thr Lys Lys Gln Val Thr Leu Thr Cys Met Val Thr Asp Phe
            340                 345                 350

Met Pro Glu Asp Ile Tyr Val Glu Trp Thr Asn Asn Gly Lys Thr Glu
        355                 360                 365

Leu Asn Tyr Lys Asn Thr Glu Pro Val Leu Asp Ser Asp Gly Ser Tyr
    370                 375                 380

Phe Met Tyr Ser Lys Leu Arg Val Glu Lys Lys Asn Trp Val Glu Arg
385                 390                 395                 400

Asn Ser Tyr Ser Cys Ser Val Val His Glu Gly Leu His Asn His His
                405                 410                 415

Thr Thr Lys Ser Phe Ser Arg Thr Pro Gly Lys
```

<210> SEQ ID NO 388
<211> LENGTH: 423
<212> TYPE: PRT
<213> ORGANISM: Artificial Sequence
<220> FEATURE:
<223> OTHER INFORMATION: Synthetic

<400> SEQUENCE: 388

```
Gly Arg Leu Val His Met Thr Val Ser Gly Ser Asn Val Thr Leu
 1               5                  10                  15

Asn Ile Ser Glu Ser Leu Pro Glu Asn Tyr Lys Gln Leu Thr Trp Phe
            20                  25                  30

Tyr Thr Phe Asp Gln Lys Ile Val Glu Trp Asp Ser Gly Lys Ser Lys
             35                  40                  45

Tyr Phe Glu Ser Lys Phe Lys Gly Arg Val Arg Leu Asp Pro Gln Ser
 50                  55                  60

Gly Ala Leu Tyr Ile Ser Lys Val Gln Lys Glu Asp Asn Ser Thr Tyr
 65                  70                  75                  80

Val Met Arg Val Leu Lys Lys Asp Gly Tyr Glu Gln Glu Trp Lys Ile
                 85                  90                  95

Lys Leu Gln Val Leu Asp Pro Val Pro Lys Pro Val Ile Lys Ile Glu
            100                 105                 110

Lys Arg Glu Asp Val Asp Asp Asn Cys Tyr Leu Lys Leu Ser Cys Val
            115                 120                 125

Ile Pro Gly Glu Ser Val Asn Tyr Thr Trp Tyr Gly Glu Leu Pro Lys
130                 135                 140

Glu Ile Gln Asn Ser Val Leu Glu Thr Thr Leu Lys Pro His Lys His
145                 150                 155                 160

Ser Arg Cys Tyr Thr Cys Gln Val Ser Asn Ser Val Ser Ser Lys Asn
                165                 170                 175

Gly Thr Phe Cys Phe Ser Pro Pro Cys Thr Ala Ala Arg Ser Glu Pro
            180                 185                 190

Arg Gly Pro Thr Ile Lys Pro Cys Pro Pro Cys Lys Cys Pro Ala Pro
            195                 200                 205

Asn Leu Leu Gly Gly Pro Ser Val Phe Ile Phe Pro Pro Lys Ile Lys
210                 215                 220

Asp Val Leu Met Ile Ser Leu Ser Pro Ile Val Thr Cys Val Val Val
225                 230                 235                 240

Asp Val Ser Glu Asp Asp Pro Asp Val Gln Ile Ser Trp Phe Val Asn
                245                 250                 255

Asn Val Glu Val His Thr Ala Gln Thr Gln Thr His Arg Glu Asp Tyr
            260                 265                 270

Asn Ser Thr Leu Arg Val Val Ser Ala Leu Pro Ile Gln His Gln Asp
            275                 280                 285

Trp Met Ser Gly Lys Glu Phe Lys Cys Lys Val Asn Asn Lys Asp Leu
290                 295                 300

Pro Ala Pro Ile Glu Arg Thr Ile Ser Lys Pro Lys Gly Ser Val Arg
305                 310                 315                 320

Ala Pro Gln Val Tyr Val Leu Pro Pro Glu Glu Glu Met Thr Lys
                325                 330                 335

Lys Gln Val Thr Leu Thr Cys Met Val Thr Asp Phe Met Pro Glu Asp
            340                 345                 350

Ile Tyr Val Glu Trp Thr Asn Asn Gly Lys Thr Glu Leu Asn Tyr Lys
```

```
                    355                 360                 365
Asn Thr Glu Pro Val Leu Asp Ser Asp Gly Ser Tyr Phe Met Tyr Ser
370                 375                 380

Lys Leu Arg Val Glu Lys Lys Asn Trp Val Glu Arg Asn Ser Tyr Ser
385                 390                 395                 400

Cys Ser Val Val His Glu Gly Leu His Asn His His Thr Thr Lys Ser
                405                 410                 415

Phe Ser Arg Thr Pro Gly Lys
                420

<210> SEQ ID NO 389
<211> LENGTH: 436
<212> TYPE: PRT
<213> ORGANISM: Artificial Sequence
<220> FEATURE:
<223> OTHER INFORMATION: Synthetic

<400> SEQUENCE: 389

Cys Gln Gly Ser Ala Asp His Val Val Ser Ile Ser Gly Val Pro Leu
1               5                   10                  15

Gln Leu Gln Pro Asn Ser Ile Gln Thr Lys Val Asp Ser Ile Ala Trp
            20                  25                  30

Lys Lys Leu Leu Pro Ser Gln Asn Gly Phe His His Ile Leu Lys Trp
        35                  40                  45

Glu Asn Gly Ser Leu Pro Ser Asn Thr Ser Asn Asp Arg Phe Ser Phe
    50                  55                  60

Ile Val Lys Asn Leu Ser Leu Leu Ile Lys Ala Ala Gln Gln Gln Asp
65                  70                  75                  80

Ser Gly Leu Tyr Cys Leu Glu Val Thr Ser Ile Ser Gly Lys Val Gln
                85                  90                  95

Thr Ala Thr Phe Gln Val Phe Val Phe Asp Lys Val Glu Lys Pro Arg
            100                 105                 110

Leu Gln Gly Gln Gly Lys Ile Leu Asp Arg Gly Arg Cys Gln Val Ala
        115                 120                 125

Leu Ser Cys Leu Val Ser Arg Asp Gly Asn Val Ser Tyr Ala Trp Tyr
130                 135                 140

Arg Gly Ser Lys Leu Ile Gln Thr Ala Gly Asn Leu Thr Tyr Leu Asp
145                 150                 155                 160

Glu Glu Val Asp Ile Asn Gly Thr His Thr Tyr Thr Cys Asn Val Ser
                165                 170                 175

Asn Pro Val Ser Trp Glu Ser His Thr Leu Asn Leu Thr Gln Asp Cys
            180                 185                 190

Gln Asn Ala His Gln Glu Phe Arg Phe Trp Pro Glu Pro Arg Gly Pro
        195                 200                 205

Thr Ile Lys Pro Cys Pro Pro Cys Lys Cys Pro Ala Pro Asn Leu Leu
210                 215                 220

Gly Gly Pro Ser Val Phe Ile Phe Pro Pro Lys Ile Lys Asp Val Leu
225                 230                 235                 240

Met Ile Ser Leu Ser Pro Ile Val Thr Cys Val Val Val Asp Val Ser
                245                 250                 255

Glu Asp Asp Pro Asp Val Gln Ile Ser Trp Phe Val Asn Asn Val Glu
            260                 265                 270

Val His Thr Ala Gln Thr Gln Thr His Arg Glu Asp Tyr Asn Ser Thr
        275                 280                 285

Leu Arg Val Val Ser Ala Leu Pro Ile Gln His Gln Asp Trp Met Ser
```

```
                290             295             300
Gly Lys Glu Phe Lys Cys Lys Val Asn Asn Lys Asp Leu Pro Ala Pro
305                 310                 315                 320

Ile Glu Arg Thr Ile Ser Lys Pro Lys Gly Ser Val Arg Ala Pro Gln
                325                 330                 335

Val Tyr Val Leu Pro Pro Glu Glu Met Thr Lys Lys Gln Val
            340                 345                 350

Thr Leu Thr Cys Met Val Thr Asp Phe Met Pro Glu Asp Ile Tyr Val
            355                 360                 365

Glu Trp Thr Asn Asn Gly Lys Thr Glu Leu Asn Tyr Lys Asn Thr Glu
            370                 375                 380

Pro Val Leu Asp Ser Asp Gly Ser Tyr Phe Met Tyr Ser Lys Leu Arg
385                 390                 395                 400

Val Glu Lys Lys Asn Trp Val Glu Arg Asn Ser Tyr Ser Cys Ser Val
                405                 410                 415

Val His Glu Gly Leu His Asn His His Thr Thr Lys Ser Phe Ser Arg
            420                 425                 430

Thr Pro Gly Lys
            435

<210> SEQ ID NO 390
<211> LENGTH: 365
<212> TYPE: PRT
<213> ORGANISM: Homo sapiens

<400> SEQUENCE: 390

Met Leu Gly Gln Val Val Thr Leu Ile Leu Leu Leu Leu Lys Val
1               5                   10                  15

Tyr Gln Gly Lys Gly Cys Gln Gly Ser Ala Asp His Val Ser Ile
            20                  25                  30

Ser Gly Val Pro Leu Gln Leu Gln Pro Asn Ser Ile Gln Thr Lys Val
            35                  40                  45

Asp Ser Ile Ala Trp Lys Lys Leu Leu Pro Ser Gln Asn Gly Phe His
50                  55                  60

His Ile Leu Lys Trp Glu Asn Gly Ser Leu Pro Ser Asn Thr Ser Asn
65                  70                  75                  80

Asp Arg Phe Ser Phe Ile Val Lys Asn Leu Ser Leu Leu Ile Lys Ala
                85                  90                  95

Ala Gln Gln Gln Asp Ser Gly Leu Tyr Cys Leu Glu Val Thr Ser Ile
            100                 105                 110

Ser Gly Lys Val Gln Thr Ala Thr Phe Gln Val Phe Val Phe Asp Lys
            115                 120                 125

Val Glu Lys Pro Arg Leu Gln Gly Gln Gly Lys Ile Leu Asp Arg Gly
130                 135                 140

Arg Cys Gln Val Ala Leu Ser Cys Leu Val Ser Arg Asp Gly Asn Val
145                 150                 155                 160

Ser Tyr Ala Trp Tyr Arg Gly Ser Lys Leu Ile Gln Thr Ala Gly Asn
                165                 170                 175

Leu Thr Tyr Leu Asp Glu Glu Val Asp Ile Asn Gly Thr His Thr Tyr
            180                 185                 190

Thr Cys Asn Val Ser Asn Pro Val Ser Trp Glu Ser His Thr Leu Asn
            195                 200                 205

Leu Thr Gln Asp Cys Gln Asn Ala His Gln Glu Phe Arg Phe Trp Pro
210                 215                 220
```

```
Phe Leu Val Ile Ile Val Ile Leu Ser Ala Leu Phe Leu Gly Thr Leu
225                 230                 235                 240

Ala Cys Phe Cys Val Trp Arg Arg Lys Arg Lys Glu Lys Gln Ser Glu
            245                 250                 255

Thr Ser Pro Lys Glu Phe Leu Thr Ile Tyr Glu Asp Val Lys Asp Leu
        260                 265                 270

Lys Thr Arg Arg Asn His Glu Gln Glu Gln Thr Phe Pro Gly Gly Gly
    275                 280                 285

Ser Thr Ile Tyr Ser Met Ile Gln Ser Gln Ser Ala Pro Thr Ser
290                 295                 300

Gln Glu Pro Ala Tyr Thr Leu Tyr Ser Leu Ile Gln Pro Ser Arg Lys
305                 310                 315                 320

Ser Gly Ser Arg Lys Arg Asn His Ser Pro Ser Phe Asn Ser Thr Ile
            325                 330                 335

Tyr Glu Val Ile Gly Lys Ser Gln Pro Lys Ala Gln Asn Pro Ala Arg
        340                 345                 350

Leu Ser Arg Lys Glu Leu Glu Asn Phe Asp Val Tyr Ser
        355                 360                 365

<210> SEQ ID NO 391
<211> LENGTH: 222
<212> TYPE: PRT
<213> ORGANISM: Artificial Sequence
<220> FEATURE:
<223> OTHER INFORMATION: Synthetic

<400> SEQUENCE: 391

Gln Gly His Leu Val His Met Thr Val Val Ser Gly Ser Asn Val Thr
1               5                   10                  15

Leu Asn Ile Ser Glu Ser Leu Pro Glu Asn Tyr Lys Gln Leu Thr Trp
            20                  25                  30

Phe Tyr Thr Phe Asp Gln Lys Ile Val Glu Trp Asp Ser Arg Lys Ser
        35                  40                  45

Lys Tyr Phe Glu Ser Lys Phe Lys Gly Arg Val Arg Leu Asp Pro Gln
50                  55                  60

Ser Gly Ala Leu Tyr Ile Ser Lys Val Gln Lys Glu Asp Asn Ser Thr
65                  70                  75                  80

Tyr Ile Met Arg Val Leu Lys Lys Thr Gly Asn Glu Gln Glu Trp Lys
                85                  90                  95

Ile Lys Leu Gln Val Leu Asp Pro Val Pro Lys Pro Val Ile Lys Ile
            100                 105                 110

Glu Lys Ile Glu Asp Met Asp Asp Asn Cys Tyr Leu Lys Leu Ser Cys
        115                 120                 125

Val Ile Pro Gly Glu Ser Val Asn Tyr Thr Trp Tyr Gly Asp Lys Arg
130                 135                 140

Pro Phe Pro Lys Glu Leu Gln Asn Ser Val Leu Glu Thr Thr Leu Met
145                 150                 155                 160

Pro His Asn Tyr Ser Arg Cys Tyr Thr Cys Gln Val Ser Asn Ser Val
                165                 170                 175

Ser Ser Lys Asn Gly Thr Val Cys Leu Ser Pro Pro Cys Thr Leu Ala
            180                 185                 190

Arg Ser Glu Gln Lys Leu Ile Ser Glu Glu Asp Leu Gly Gly Glu Gln
        195                 200                 205

Lys Leu Ile Ser Glu Glu Asp Leu His His His His His
    210                 215                 220
```

<210> SEQ ID NO 392
<211> LENGTH: 351
<212> TYPE: PRT
<213> ORGANISM: Homo sapiens

<400> SEQUENCE: 392

```
Met Ser Phe Pro Cys Lys Phe Val Ala Ser Phe Leu Leu Ile Phe Asn
  1               5                  10                  15

Val Ser Ser Lys Gly Ala Val Ser Lys Glu Ile Thr Asn Ala Leu Glu
             20                  25                  30

Thr Trp Gly Ala Leu Gly Gln Asp Ile Asn Leu Asp Ile Pro Ser Phe
         35                  40                  45

Gln Met Ser Asp Asp Ile Asp Asp Ile Lys Trp Glu Lys Thr Ser Asp
 50                  55                  60

Lys Lys Lys Ile Ala Gln Phe Arg Lys Glu Lys Glu Thr Phe Lys Glu
 65                  70                  75                  80

Lys Asp Thr Tyr Lys Leu Phe Lys Asn Gly Thr Leu Lys Ile Lys His
                 85                  90                  95

Leu Lys Thr Asp Asp Gln Asp Ile Tyr Lys Val Ser Ile Tyr Asp Thr
            100                 105                 110

Lys Gly Lys Asn Val Leu Glu Lys Ile Phe Asp Leu Lys Ile Gln Glu
            115                 120                 125

Arg Val Ser Lys Pro Lys Ile Ser Trp Thr Cys Ile Asn Thr Thr Leu
130                 135                 140

Thr Cys Glu Val Met Asn Gly Thr Asp Pro Glu Leu Asn Leu Tyr Gln
145                 150                 155                 160

Asp Gly Lys His Leu Lys Leu Ser Gln Arg Val Ile Thr His Lys Trp
                165                 170                 175

Thr Thr Ser Leu Ser Ala Lys Phe Lys Cys Thr Ala Gly Asn Lys Val
            180                 185                 190

Ser Lys Glu Ser Ser Val Glu Pro Val Ser Cys Pro Glu Lys Gly Leu
            195                 200                 205

Asp Ile Tyr Leu Ile Ile Gly Ile Cys Gly Gly Gly Ser Leu Leu Met
210                 215                 220

Val Phe Val Ala Leu Leu Val Phe Tyr Ile Thr Lys Arg Lys Lys Gln
225                 230                 235                 240

Arg Ser Arg Arg Asn Asp Glu Glu Leu Glu Thr Arg Ala His Arg Val
                245                 250                 255

Ala Thr Glu Glu Arg Gly Arg Lys Pro His Gln Ile Pro Ala Ser Thr
            260                 265                 270

Pro Gln Asn Pro Ala Thr Ser Gln His Pro Pro Pro Pro Gly His
            275                 280                 285

Arg Ser Gln Ala Pro Ser His Arg Pro Pro Pro Gly His Arg Val
            290                 295                 300

Gln His Gln Pro Gln Lys Arg Pro Pro Ala Pro Ser Gly Thr Gln Val
305                 310                 315                 320

His Gln Gln Lys Gly Pro Pro Leu Pro Arg Pro Arg Val Gln Pro Lys
                325                 330                 335

Pro Pro His Gly Ala Ala Glu Asn Ser Leu Ser Pro Ser Asn
            340                 345                 350
```

US 9,228,014 B2

ANTIBODIES CAPABLE OF BLOCKING THE INTERACTION BETWEEN CD48 AND A CD48 RECEPTOR

CROSS-REFERENCE TO RELATED APPLICATIONS

This application claims the benefit under 35 U.S.C. §119(e) of U.S. provisional application No. 61/386,746, filed on Sep. 27, 2010; 61/475,280, filed on Apr. 14, 2011; and 61/515,490, filed on Aug. 15, 2011, the disclosures of which are herein incorporated by reference in their entireties.

FIELD OF THE INVENTION

The present invention relates to antibodies, and antigen-binding fragments thereof, which are specific for human CD48.

BACKGROUND

CD48 is a GPI-anchored protein that exists in both membrane-bound and soluble forms. CD48 is a high-affinity ligand for 2B4 and a low-affinity ligand for CD2. CD48 has also been referred to in the scientific literature as "TCT.1" (Mami-Chouaib et al., *J. Exp. Med.* 172:1071-1082 (1990)), "B-LAST 1" (Thorley-Lawson et al., *Cell* 30:415-425 (1982)), and SLAMF2 (Detre et al., *Semin. Immunopathol.* 32:157-171 (2010)). The interaction between CD48 and 2B4 was shown to cause NK cell activation. CD48 has also been shown to stimulate T-cell activation in vitro, and CD48-knockout mice display an impaired T-cell proliferation response.

Certain lines of evidence suggest a role for CD48 in asthma progression and inflammatory bowel disease (IBD). For example, CD48 was shown to be upregulated in experimental asthma (e.g., ovalbumin- and *Aspergillus*-induced allergic eosinophilic airway inflammation models). See, e.g., Munitz et al., *Am. J. Respir. Crit. Care Med.* 175:911-918 (2007). Moreover, CD48 knock-out mice failed to develop inflammatory colitis in the adoptive transfer model of IBD. Furthermore, CD48 antagonism was shown to produce beneficial effects in previously established colitis.

The use of CD48 antagonists for therapeutic purposes are mentioned in, e.g., US 2007/0212353 and WO 97/35614. Nonetheless, there remains a need in the art for novel CD48 modulating agents, including anti-CD48 antibodies, that can be used to treat CD48-mediated diseases and conditions.

BRIEF SUMMARY OF THE INVENTION

The present invention provides antibodies that bind human CD48. The antibodies of the invention are useful, inter alia, for inhibiting CD48-mediated signaling and for treating diseases and disorders caused by or related to CD48 activity and/or signaling.

The antibodies of the present invention block the interaction between CD48 and a CD48 receptor (e.g., 2B4 and/or CD2), and/or inhibit the activation of primary human peripheral blood mononuclear cells (PBMCs). According to certain embodiments, the antibodies of the invention bind an epitope within the first immunoglobulin domain of human CD48.

The antibodies of the invention can be full-length (for example, an IgG1 or IgG4 antibody) or may comprise only an antigen-binding portion (for example, a Fab, F(ab')₂ or scFv fragment), and may be modified to affect functionality, e.g., to eliminate residual effector functions (Reddy et al., 2000, J. Immunol. 164:1925-1933).

The present invention provides an antibody or antigen-binding fragment of an antibody comprising a heavy chain variable region (HCVR) having an amino acid sequence selected from the group consisting of SEQ ID NO: 2, 18, 34, 50, 66, 82, 98, 114, 130, 162, 178, 192, 208, 212, 228, 232, 248, 252, 268, 272, 288, 292, 308, 312, 328, 332, 348, 352, and 368, or a substantially similar sequence thereof having at least 90%, at least 95%, at least 98% or at least 99% sequence identity.

The present invention also provides an antibody or antigen-binding fragment of an antibody comprising a light chain variable region (LCVR) having an amino acid sequence selected from the group consisting of SEQ ID NO: 10, 26, 42, 58, 74, 90, 106, 122, 138, 146, 154, 170, 180, 182, 190, 200, 210, 220, 230, 240, 250, 260, 270, 280, 290, 300, 310, 320, 330, 340, 350, 360, 370, 372, and 380, or a substantially similar sequence thereof having at least 90%, at least 95%, at least 98% or at least 99% sequence identity.

The present invention also provides an antibody or antigen-binding fragment thereof comprising a HCVR and LCVR (HCVR/LCVR) sequence pair selected from the group consisting of SEQ ID NO: 2/10, 18/26, 34/42, 50/58, 66/74, 82/90, 98/106, 114/122, 130/138, 162/170, 178/180, 162/182, 178/190, 192/200, 208/210, 212/220, 228/230, 232/240, 248/250, 252/260, 268/270, 272/280, 288/290, 292/300, 308/310, 312/320, 328/330, 332/340, 348/350, 352/360, 368/370, 352/372, and 368/380.

The present invention also provides an antibody or antigen-binding fragment of an antibody comprising a heavy chain CDR3 (HCDR3) domain having an amino acid sequence selected from the group consisting of SEQ ID NO: 8, 24, 40, 56, 72, 88, 104, 120, 136, 168, 198, 218, 238, 258, 278, 298, 318, 338, and 358, or a substantially similar sequence thereof having at least 90%, at least 95%, at least 98% or at least 99% sequence identity; and a light chain CDR3 (LCDR3) domain having an amino acid sequence selected from the group consisting of SEQ ID NO: 16, 32, 48, 64, 80, 96, 112, 128, 144, 152, 160, 176, 188, 206, 226, 246, 266, 286, 306, 326, 346, 366, and 378, or a substantially similar sequence thereof having at least 90%, at least 95%, at least 98% or at least 99% sequence identity.

In certain embodiments, the antibody or antigen-binding portion of an antibody comprises a HCDR3/LCDR3 amino acid sequence pair selected from the group consisting of SEQ ID NO: 8/16, 24/32, 40/48, 56/64, 72/80, 88/96, 104/112, 120/128, 136/144, 168/176, 168/188, 198/206, 218/226, 238/246, 258/266, 278/286, 298/306, 318/326, 338/346, 358/366, and 358/378.

The present invention also provides an antibody or fragment thereof further comprising a heavy chain CDR1 (HCDR1) domain having an amino acid sequence selected from the group consisting of SEQ ID NO: 4, 20, 36, 52, 68, 84, 100, 116, 132, 164, 194, 214, 234, 254, 274, 294, 314, 334, and 354, or a substantially similar sequence thereof having at least 90%, at least 95%, at least 98% or at least 99% sequence identity; a heavy chain CDR2 (HCDR2) domain having an amino acid sequence selected from the group consisting of SEQ ID NO: 6, 22, 38, 54, 70, 86, 102, 118, 134, 166, 196, 216, 236, 256, 276, 296, 316, 336, and 356, or a substantially similar sequence thereof having at least 90%, at least 95%, at least 98% or at least 99% sequence identity; a light chain CDR1 (LCDR1) domain having an amino acid sequence selected from the group consisting of SEQ ID NO: 12, 28, 44, 60, 76, 92, 108, 124, 140, 148, 156, 172, 184, 202, 222, 242, 262, 282, 302, 322, 342, 362, and 374, or a substantially similar sequence thereof having at least 90%, at least 95%, at least 98% or at least 99% sequence identity; and a light chain CDR2 (LCDR2) domain having an amino acid sequence selected from the group consisting of SEQ ID NO: 14, 30, 46, 62, 78, 94, 110, 126, 142, 150, 158, 174, 186, 204, 224, 244, 264, 284, 304, 324, 344, 364, and 376, or a substantially similar sequence thereof having at least 90%, at least 95%, at least 98% or at least 99% sequence identity.

Certain non-limiting, exemplary antibodies and antigen-binding fragments of the invention comprise HCDR1-HCDR2-HCDR3-LCDR1-LCDR2-LCDR3 domains, respectively, having the amino acid sequences selected from the group consisting of: SEQ ID NOs: 4-6-8-12-14-16 (e.g. H2M1707N); 20-22-24-28-30-32 (e.g. H2M1709N); 36-38-40-44-46-48 (e.g. H2M1710N); 52-54-56-60-62-64 (e.g. H2M1712N); 68-70-72-76-78-80 (e.g. H2M1713N); 84-86-88-92-94-96 (e.g. H2M1763N); 100-102-104-108-110-112 (e.g. H2M1764N); 116-118-120-124-126-128 (e.g. H2M1811N); 132-134-136-140-142-144 (e.g. H2M1766N); 164-166-168-172-174-176 (e.g. H4H1769N-a); 164-166-168-184-186-188 (e.g. H4H1769N-b); 194-196-198-202-204-206 (e.g. H4H1770N); 214-216-218-222-224-226 (e.g. H4H1771N); 234-236-238-242-244-246 (e.g. H4H1772N); 254-256-258-262-264-266 (e.g. H4H1774N); 274-276-278-282-284-286 (e.g. H4H1775N); 294-296-298-302-304-306 (e.g. H4H1778N); 314-316-318-322-324-326 (e.g. H4H1779N); 334-336-338-342-344-346 (e.g. H4H1781N); 354-356-358-362-364-366 (e.g. H4H1789Na and Pa); and 354-356-358-374-376-378 (e.g. H4H1789Nb and Pb).

The present invention also includes antibodies, or antigen-binding fragments thereof, which comprise HCDR1-HCDR2-HCDR3-LCDR1-LCDR2-LCDR3 domains, respectively, having the following amino acid sequences: HCDR1=GFTFSNYG (SEQ ID NO:254); HCDR2=IWYDDSXK, wherein X is S or N (SEQ ID NO:381); HCDR3=ARDRWTYSHXFEY, wherein X is Y or F (SEQ ID NO:382); LCDR1=QXISSW, wherein X is D or G (SEQ ID NO:383); LCDR2=AAS (SEQ ID NO:264); and LCDR3=QQANSFPRT (SEQ ID NO:266). Non-limiting exemplary antibodies of the invention which have these sequence characteristics include H4H1774N, H4H1775N, H4H1778N, H4H1779N, and H4H1781N.

In a related embodiment, the invention includes an antibody or antigen-binding fragment of an antibody which specifically binds CD48, wherein the antibody or fragment comprises the heavy and light chain CDR domains contained within heavy and light chain sequences selected from the group consisting of SEQ ID NO: 2/10, 18/26, 34/42, 50/58, 66/74, 82/90, 98/106, 114/122, 130/138, 162/170, 178/180, 162/182, 178/190, 192/200, 208/210, 212/220, 228/230, 232/240, 248/250, 252/260, 268/270, 272/280, 288/290, 292/300, 308/310, 312/320, 328/330, 332/340, 348/350, 352/360, 368/370, 352/372, and 368/380. Methods and techniques for identifying CDRs within HCVR and LCVR amino acid sequences are well known in the art and can be used to identify CDRs within the specified HCVR and/or LCVR amino acid sequences disclosed herein. Exemplary conventions that can be used to identify the boundaries of CDRs include, e.g., the Kabat definition, the Chothia definition, and the AbM definition. In general terms, the Kabat definition is based on sequence variability, the Chothia definition is based on the location of the structural loop regions, and the AbM definition is a compromise between the Kabat and Chothia approaches. See, e.g., Kabat, "Sequences of Proteins of Immunological Interest," National Institutes of Health, Bethesda, Md. (1991); Al-Lazikani et al., *J. Mol. Biol.* 273:927-948 (1997); and Martin et al., *Proc. Natl. Acad. Sci. USA* 86:9268-9272 (1989). Public databases are also available for identifying CDR sequences within an antibody.

In another aspect, the invention provides nucleic acid molecules encoding anti-CD48 antibodies or fragments thereof. Recombinant expression vectors carrying the nucleic acids of the invention, and host cells into which such vectors have been introduced, are also encompassed by the invention, as are methods of producing the antibodies by culturing the host cells under conditions permitting production of the antibodies, and recovering the antibodies produced.

In one embodiment, the invention provides an antibody or fragment thereof comprising a HCVR encoded by a nucleic acid sequence selected from the group consisting of SEQ ID NO: 1, 17, 33, 49, 65, 81, 97, 113, 129, 161, 177, 191, 207, 211, 227, 231, 247, 251, 267, 271, 287, 291, 307, 311, 327, 331, 347, 351, and 367, or a substantially identical sequence having at least 90%, at least 95%, at least 98%, or at least 99% homology thereof.

The present invention also provides an antibody or fragment thereof comprising a LCVR encoded by a nucleic acid sequence selected from the group consisting of SEQ ID NO: 9, 25, 41, 57, 73, 89, 105, 121, 137, 145, 153, 169, 179, 181, 189, 199, 209, 219, 229, 239, 249, 259, 269, 279, 289, 299, 309, 319, 329, 339, 349, 359, 369, 371, and 379, or a substantially identical sequence having at least 90%, at least 95%, at least 98%, or at least 99% homology thereof.

The present invention also provides an antibody or antigen-binding fragment of an antibody comprising a HCDR3 domain encoded by a nucleotide sequence selected from the group consisting of SEQ ID NO: 7, 23, 39, 55, 71, 87, 103, 119, 135, 167, 197, 217, 237, 257, 277, 297, 317, 337, and 357, or a substantially identical sequence having at least 90%, at least 95%, at least 98%, or at least 99% homology thereof; and a LCDR3 domain encoded by a nucleotide sequence selected from the group consisting of SEQ ID NO: 15, 31, 47, 63, 79, 95, 111, 127, 143, 151, 159, 175, 187, 205, 225, 245, 265, 285, 305, 325, 345, 365, and 377, or a substantially identical sequence having at least 90%, at least 95%, at least 98%, or at least 99% homology thereof.

The present invention also provides an antibody or fragment thereof which further comprises a HCDR1 domain encoded by a nucleotide sequence selected from the group consisting of SEQ ID NO: 3, 19, 35, 51, 67, 83, 99, 115, 131, 163, 193, 213, 233, 253, 273, 293, 313, 333, and 353 or a substantially identical sequence having at least 90%, at least 95%, at least 98%, or at least 99% homology thereof; a HCDR2 domain encoded by a nucleotide sequence selected from the group consisting of SEQ ID NO: 5, 21, 37, 53, 69, 85, 101, 117, 133, 165, 195, 215, 235, 255, 275, 295, 315, 335, and 355, or a substantially identical sequence having at least 90%, at least 95%, at least 98%, or at least 99% homology thereof; a LCDR1 domain encoded by a nucleotide sequence selected from the group consisting of SEQ ID NO: 11, 27, 43, 59, 75, 91, 107, 123, 139, 147, 155, 171, 183, 201, 221, 241, 261, 281, 301, 321, 341, 361, and 373, or a substantially identical sequence having at least 90%, at least 95%, at least 98%, or at least 99% homology thereof; and a LCDR2 domain encoded by a nucleotide sequence selected from the group consisting of SEQ ID NO: 13, 29, 45, 61, 77, 93, 109, 125, 141, 149, 157, 173, 185, 203, 223, 243, 263, 283, 303, 323, 343, 363, and 375, or a substantially identical sequence having at least 90%, at least 95%, at least 98%, or at least 99% homology thereof.

According to certain embodiments, the antibody or fragment thereof comprises the heavy and light chain CDR sequences encoded by the nucleic acid sequences of SEQ ID NOs: SEQ ID NOs: 1 and 9 (e.g. H2M1707N), 17 and 25 (e.g. H2M1709N), 33 and 41 (e.g. H2M1710N), 49 and 57 (e.g. H2M1712N), 65 and 73 (e.g. H2M1713N), 81 and 89 (e.g. H2M1763N), 97 and 105 (e.g. H2M1764N), 113 and 121 (e.g. H2M1811N), 129 and 137 (e.g. H2M1766N), 161 and 169 (e.g. H4H1769N-a), 177 and 179 (e.g., H4H1769P-a), 161 and 181 (e.g. H4H1769N-b), 177 and 189 (e.g., H4H1769P-b), 191 and 199 (e.g. H4H1770N), 207 and 209 (e.g., H4H1770P), 211 and 219 (e.g. H4H1771N), 227 and 229 (e.g., H4H1771P), 231 and 239 (e.g. H4H1772N), 247 and 249 (e.g., H4H1772P), 251 and 259 (e.g. H4H1774N), 267 and 269 (e.g., H4H1774P), 271 and 279 (e.g. H4H1775N), 287 and 289 (e.g., H4H1775P), 291 and 299 (e.g. H4H1778N), 307 and 309 (e.g., H4H1778P), 311 and 319 (e.g. H4H1779N), 327 and 329 (e.g., H4H1779P), 331 and 339 (e.g. H4H1781N), 347 and 349 (e.g., H4H1781P), 351 and 359 (e.g. H4H1789Na), 367 and 369 (e.g., H4H1789 Pa), 351 and 371 (e.g. H4H1789Nb), or 367 and 379 (e.g., H4H1789Pb).

The present invention includes anti-CD48 antibodies having a modified glycosylation pattern. In some applications, modification to remove undesirable glycosylation sites may be useful, or an antibody lacking a fucose moiety present on the oligosaccharide chain, for example, to increase antibody dependent cellular cytotoxicity (ADCC) function (see Shield et al. (2002) JBC 277:26733). In other applications, modification of galactosylation can be made in order to modify complement dependent cytotoxicity (CDC).

In another aspect, the invention provides a pharmaceutical composition comprising a recombinant human antibody or fragment thereof which specifically binds CD48 and a pharmaceutically acceptable carrier. In a related aspect, the invention features a composition which is a combination of a CD48 inhibitor and a second therapeutic agent. In one embodiment, the CD48 inhibitor is an antibody or fragment thereof. In one embodiment, the second therapeutic agent is any agent that is advantageously combined with a CD48 inhibitor. Exemplary agents that may be advantageously combined with a CD48 inhibitor include, without limitation, other agents that inhibit CD48 activity (including other antibodies or antigen-binding fragments thereof, peptide inhibitors, small molecule antagonists, etc) and/or agents which interfere with CD48 upstream or downstream signaling.

In yet another aspect, the invention provides methods for inhibiting CD48 activity using an anti-CD48 antibody or antigen-binding portion of an antibody of the invention, wherein the therapeutic methods comprise administering a therapeutically effective amount of a pharmaceutical composition comprising an antibody or antigen-binding fragment of an antibody of the invention. The disorder treated is any disease or condition which is improved, ameliorated, inhibited or prevented by removal, inhibition or reduction of CD48 activity. The anti-CD48 antibody or antibody fragment of the invention may function to block the interaction between CD48 and a CD48 receptor (e.g., 2B4 and/or CD2), or otherwise inhibit the signaling activity of CD48.

The present invention also includes the use of an anti-CD48 antibody or antigen binding portion of an antibody of the invention in the manufacture of a medicament for the treatment of a disease or disorder related to or caused by CD48 activity in a patient.

Other embodiments will become apparent from a review of the ensuing detailed description.

DETAILED DESCRIPTION

Figure 1:
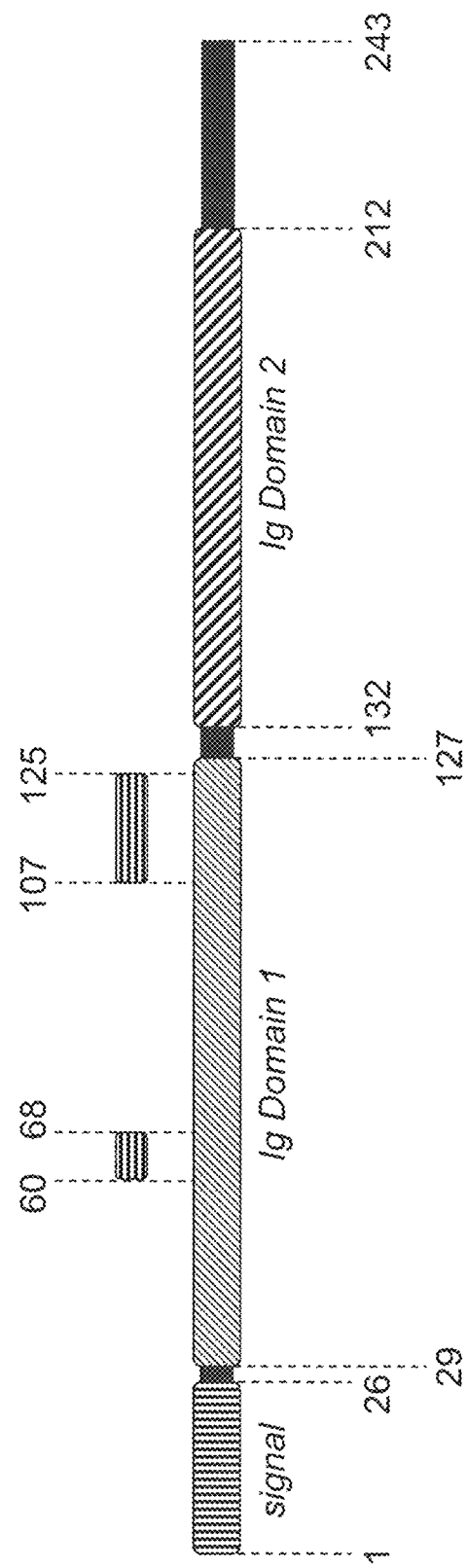
FIG. 1. Linear depiction of human CD48 polypeptide (SEQ ID NO:384). The portion represented by amino acids 1-26 is the signal sequence; The portion represented by amino acids 29-127 is Ig Domain 1; The portion represented by amino acids 132-212 is Ig Domain 2. The regions of SEQ ID NO:384 corresponding to amino acids 60-68 (YTFDQKIVE) and 107-125 (YIMRVLKKTGNEQEWKIKL) represent the epitope determined for the exemplary antibody designated H4H1789 Pa (see Example 4).

Before the present invention is described, it is to be understood that this invention is not limited to particular methods and experimental conditions described, as such methods and conditions may vary. It is also to be understood that the terminology used herein is for the purpose of describing particular embodiments only, and is not intended to be limiting, since the scope of the present invention will be limited only by the appended claims.

Unless defined otherwise, all technical and scientific terms used herein have the same meaning as commonly understood by one of ordinary skill in the art to which this invention belongs. As used herein, the term "about," when used in reference to a particular recited numerical value, means that the value may vary from the recited value by no more than 1%. For example, as used herein, the expression "about 100" includes 99 and 101 and all values in between (e.g., 99.1, 99.2, 99.3, 99.4, etc.).

Although any methods and materials similar or equivalent to those described herein can be used in the practice or testing of the present invention, the preferred methods and materials are now described. All patents, applications and non-patent publications mentioned in this specification are incorporated herein by reference in their entireties.

DEFINITIONS

The expressions "CD48" and "CD48 fragment," as used herein refer to the human CD48 protein or fragment unless specified as being from a non-human species (e.g., "mouse CD48," "mouse CD48 fragment," "monkey CD48," "monkey CD48 fragment," etc.). Human CD48 has the amino acid sequence of SEQ ID NO:384. Amino acid sequences of CD48 molecules from non-human species (e.g., mouse, monkey, rabbit, dog, pig, etc.) are available from public sources such as GenBank (e.g., GenBank accession numbers BAE96326.1 (mouse); DAA31966.1 (bovine); EDL94663.1 (rat); etc).

The term "CD48 receptor," as used herein, means a protein with which the human CD48 protein interacts to transmit a biological signal in vivo. The term "CD48 receptor" includes human 2B4 and human CD2. The term "human 2B4," as used herein, means a protein comprising the amino acid sequence of SEQ ID NO:390, or a portion thereof which is capable of interacting with CD48. The term "human CD2," as used herein, means a protein comprising the amino acid sequence of SEQ ID NO:392, or a portion thereof which is capable of interacting with CD48.

The term "antibody", as used herein, is intended to refer to immunoglobulin molecules comprising four polypeptide chains, two heavy (H) chains and two light (L) chains interconnected by disulfide bonds, as well as multimers thereof (e.g., IgM). Each heavy chain comprises a heavy chain variable region (abbreviated herein as HCVR or $V_H$) and a heavy chain constant region. The heavy chain constant region comprises three domains, $C_H1$, $C_H2$ and $C_H3$. Each light chain comprises a light chain variable region (abbreviated herein as LCVR or $V_L$) and a light chain constant region. The light chain constant region comprises one domain ($C_L1$). The $V_H$ and $V_L$ regions can be further subdivided into regions of hypervariability, termed complementarity determining regions (CDRs), interspersed with regions that are more conserved, termed framework regions (FR). Each $V_H$ and $V_L$ is composed of three CDRs and four FRs, arranged from amino-terminus to carboxy-terminus in the following order: FR1, CDR1, FR2, CDR2, FR3, CDR3, FR4. In different embodiments of the invention, the FRs of the anti-CD48 antibody (or antigen-binding portion thereof) may be identical to the human germline sequences, or may be naturally or artificially modified. An amino acid consensus sequence may be defined based on a side-by-side analysis of two or more CDRs.

The term "antibody," as used herein, also includes antigen-binding fragments of full antibody molecules. The terms "antigen-binding portion" of an antibody, "antigen-binding fragment" of an antibody, and the like, as used herein, include any naturally occurring, enzymatically obtainable, synthetic, or genetically engineered polypeptide or glycoprotein that specifically binds an antigen to form a complex. Antigen-binding fragments of an antibody may be derived, e.g., from full antibody molecules using any suitable standard techniques such as proteolytic digestion or recombinant genetic engineering techniques involving the manipulation and expression of DNA encoding antibody variable and optionally constant domains. Such DNA is known and/or is readily available from, e.g., commercial sources, DNA libraries (including, e.g., phage-antibody libraries), or can be synthesized. The DNA may be sequenced and manipulated chemically or by using molecular biology techniques, for example, to arrange one or more variable and/or constant domains into a suitable configuration, or to introduce codons, create cysteine residues, modify, add or delete amino acids, etc.

Non-limiting examples of antigen-binding fragments include: (i) Fab fragments; (ii) F(ab')2 fragments; (iii) Fd fragments; (iv) Fv fragments; (v) single-chain Fv (scFv) molecules; (vi) dAb fragments; and (vii) minimal recognition units consisting of the amino acid residues that mimic the hypervariable region of an antibody (e.g., an isolated complementarity determining region (CDR) such as a CDR3 peptide), or a constrained FR3-CDR3-FR4 peptide. Other engineered molecules, such as domain-specific antibodies, single domain antibodies, domain-deleted antibodies, chimeric antibodies, CDR-grafted antibodies, diabodies, triabodies, tetrabodies, minibodies, nanobodies (e.g. monovalent nanobodies, bivalent nanobodies, etc.), small modular immunopharmaceuticals (SMIPs), and shark variable IgNAR domains, are also encompassed within the expression "antigen-binding fragment," as used herein.

An antigen-binding fragment of an antibody will typically comprise at least one variable domain. The variable domain may be of any size or amino acid composition and will generally comprise at least one CDR which is adjacent to or in frame with one or more framework sequences. In antigen-binding fragments having a $V_H$ domain associated with a $V_L$ domain, the $V_H$ and $V_L$ domains may be situated relative to one another in any suitable arrangement. For example, the variable region may be dimeric and contain $V_H$-$V_H$, $V_H$-$V_L$ or $V_L$-$V_L$ dimers. Alternatively, the antigen-binding fragment of an antibody may contain a monomeric $V_H$ or $V_L$ domain.

In certain embodiments, an antigen-binding fragment of an antibody may contain at least one variable domain covalently linked to at least one constant domain. Non-limiting, exemplary configurations of variable and constant domains that may be found within an antigen-binding fragment of an antibody of the present invention include: (i) $V_H$-$C_H1$; (ii) $V_H$-$C_H2$; (iii) $V_H$-$C_H3$; (iv) $V_H$-$C_H1$-$C_H2$; (V) $V_H$-$C_H1$-$C_H2$-$C_H3$; (vi) $V_H$-$C_H2$-$C_H3$; (vii) $V_H$-$C_L$; (viii) $V_L$-$C_H1$; (ix) $V_L$-$C_H2$; (X) $V_L$-$C_H3$; (xi) $V_L$-$C_{H1}$-$C_H2$; (xii) $V_L$-$C_H1$-$C_H2$-$C_H3$; (xiii) $V_L$-$C_H2$-$C_H3$; and (xiv) $V_L$-$C_L$. In any configuration of variable and constant domains, including any of the exemplary configurations listed above, the variable and constant domains may be either directly linked to one another or may be linked by a full or partial hinge or linker region. A hinge region may consist of at least 2 (e.g., 5, 10, 15, 20, 40, 60 or more) amino acids which result in a flexible or semi-flexible linkage between adjacent variable and/or constant domains in a single polypeptide molecule. Moreover, an antigen-binding fragment of an antibody of the present invention may comprise a homo-dimer or hetero-dimer (or other multimer) of any of the variable and constant domain configurations listed above in non-covalent association with one another and/or with one or more monomeric $V_H$ or $V_L$ domain (e.g., by disulfide bond(s)).

As with full antibody molecules, antigen-binding fragments may be monospecific or multispecific (e.g., bispecific). A multispecific antigen-binding fragment of an antibody will typically comprise at least two different variable domains, wherein each variable domain is capable of specifically binding to a separate antigen or to a different epitope on the same antigen. Any multispecific antibody format, including the exemplary bispecific antibody formats disclosed herein, may be adapted for use in the context of an antigen-binding fragment of an antibody of the present invention using routine techniques available in the art.

The antibodies of the present invention may function through complement-dependent cytotoxicity (CDC) or antibody-dependent cell-mediated cytotoxicity (ADCC). "Complement-dependent cytotoxicity" (CDC) refers to lysis of antigen-expressing cells by an antibody of the invention in the presence of complement. "Antibody-dependent cell-mediated cytotoxicity" (ADCC) refers to a cell-mediated reaction in which nonspecific cytotoxic cells that express Fc receptors (FcRs) (e.g., Natural Killer (NK) cells, neutrophils, and macrophages) recognize bound antibody on a target cell and thereby lead to lysis of the target cell. CDC and ADCC can be measured using assays that are well known and available in the art. (See, e.g., U.S. Pat. Nos. 5,500,362 and 5,821,337, and Clynes et al. (1998) Proc. Natl. Acad. Sci. (USA) 95:652-656). The constant region of an antibody is important in the ability of an antibody to fix complement and mediate cell-dependent cytotoxicity. Thus, the isotype of an antibody may be selected on the basis of whether it is desirable for the antibody to mediate cytotoxicity.

The term "human antibody", as used herein, is intended to include antibodies having variable and constant regions derived from human germline immunoglobulin sequences. The human antibodies of the invention may include amino acid residues not encoded by human germline immunoglobulin sequences (e.g., mutations introduced by random or site-specific mutagenesis in vitro or by somatic mutation in vivo), for example in the CDRs and in particular CDR3. However, the term "human antibody", as used herein, is not intended to include antibodies in which CDR sequences derived from the germline of another mammalian species, such as a mouse, have been grafted onto human framework sequences.

The term "recombinant human antibody", as used herein, is intended to include all human antibodies that are prepared, expressed, created or isolated by recombinant means, such as antibodies expressed using a recombinant expression vector transfected into a host cell (described further below), antibodies isolated from a recombinant, combinatorial human antibody library (described further below), antibodies isolated from an animal (e.g., a mouse) that is transgenic for human immunoglobulin genes (see e.g., Taylor et al. (1992) Nucl. Acids Res. 20:6287-6295) or antibodies prepared, expressed, created or isolated by any other means that involves splicing of human immunoglobulin gene sequences to other DNA sequences. Such recombinant human antibodies have variable and constant regions derived from human germline immunoglobulin sequences. In certain embodiments, however, such recombinant human antibodies are subjected to in vitro mutagenesis (or, when an animal transgenic for human Ig sequences is used, in vivo somatic mutagenesis) and thus the amino acid sequences of the $V_H$ and $V_L$ regions of the recombinant antibodies are sequences that, while derived from and related to human germline $V_H$ and $V_L$ sequences, may not naturally exist within the human antibody germline repertoire in vivo.

Human antibodies can exist in two forms that are associated with hinge heterogeneity. In one form, an immunoglobulin molecule comprises a stable four chain construct of approximately 150-160 kDa in which the dimers are held together by an interchain heavy chain disulfide bond. In a second form, the dimers are not linked via inter-chain disulfide bonds and a molecule of about 75-80 kDa is formed composed of a covalently coupled light and heavy chain (half-antibody). These forms have been extremely difficult to separate, even after affinity purification.

The frequency of appearance of the second form in various intact IgG isotypes is due to, but not limited to, structural differences associated with the hinge region isotype of the antibody. A single amino acid substitution in the hinge region of the human IgG4 hinge can significantly reduce the appearance of the second form (Angal et al. (1993) Molecular Immunology 30:105) to levels typically observed using a human IgG1 hinge. The instant invention encompasses antibodies having one or more mutations in the hinge, $C_H2$ or $C_H3$ region which may be desirable, for example, in production, to improve the yield of the desired antibody form.

An "isolated antibody," as used herein, means an antibody that has been identified and separated and/or recovered from at least one component of its natural environment. For example, an antibody that has been separated or removed from at least one component of an organism, or from a tissue or cell in which the antibody naturally exists or is naturally produced, is an "isolated antibody" for purposes of the present invention. An isolated antibody also includes an antibody in situ within a recombinant cell. Isolated antibodies are antibodies that have been subjected to at least one purification or isolation step. According to certain embodiments, an isolated antibody may be substantially free of other cellular material and/or chemicals.

The term "specifically binds," or the like, means that an antibody or antigen-binding fragment thereof forms a complex with an antigen that is relatively stable under physiologic conditions. Methods for determining whether an antibody specifically binds to an antigen are well known in the art and include, for example, equilibrium dialysis, surface plasmon resonance, and the like. For example, an antibody that "specifically binds" human CD48, as used in the context of the present invention, includes antibodies that bind human CD48 or portion thereof with a $K_D$ of less than about 1000 nM, less than about 500 nM, less than about 300 nM, less than about 200 nM, less than about 100 nM, less than about 90 nM, less than about 80 nM, less than about 70 nM, less than about 60 nM, less than about 50 nM, less than about 40 nM, less than about 30 nM, less than about 20 nM, less than about 10 nM, less than about 5 nM, less than about 4 nM, less than about 3 nM, less than about 2 nM, less than about 1 nM or less than about 0.5 nM, as measured in a surface plasmon resonance assay. (See, e.g., Example 3, herein). An isolated antibody that specifically binds human CD48 may, however, have cross-reactivity to other antigens, such as CD48 molecules from other (non-human) species.

A "neutralizing" or "blocking" antibody, as used herein, is intended to refer to an antibody whose binding to CD48: (i) interferes with the interaction between CD48 or a CD48 fragment and a CD48 receptor (e.g., 2B4 and/or CD2), and/or (ii) results in inhibition of at least one biological function of CD48. The inhibition caused by a CD48 neutralizing or blocking antibody need not be complete so long as it is detectable using an appropriate assay. Exemplary assays for detecting CD48 inhibition are described herein.

The anti-CD48 antibodies disclosed herein may comprise one or more amino acid substitutions, insertions and/or deletions in the framework and/or CDR regions of the heavy and light chain variable domains as compared to the corresponding germline sequences from which the antibodies were derived. Such mutations can be readily ascertained by comparing the amino acid sequences disclosed herein to germline sequences available from, for example, public antibody sequence databases. The present invention includes antibodies, and antigen-binding fragments thereof, which are derived from any of the amino acid sequences disclosed herein, wherein one or more amino acids within one or more framework and/or CDR regions are mutated to the corresponding residue(s) of the germline sequence from which the antibody was derived, or to the corresponding residue(s) of another human germline sequence, or to a conservative amino acid substitution of the corresponding germline residue(s) (such sequence changes are referred to herein collectively as "germline mutations"). A person of ordinary skill in the art, starting with the heavy and light chain variable region sequences disclosed herein, can easily produce numerous antibodies and antigen-binding fragments which comprise one or more individual germline mutations or combinations thereof. In certain embodiments, all of the framework and/or CDR residues within the $V_H$ and/or $V_L$ domains are mutated back to the residues found in the original germline sequence from which the antibody was derived. In other embodiments, only certain residues are mutated back to the original germline sequence, e.g., only the mutated residues found within the first 8 amino acids of FR1 or within the last 8 amino acids of FR4, or only the mutated residues found within CDR1, CDR2 or CDR3. In other embodiments, one or more of the framework and/or CDR residue(s) are mutated to the corresponding residue(s) of a different germline sequence (i.e., a germline sequence that is different from the germline sequence from which the antibody was originally derived). Furthermore, the antibodies of the present invention may contain any combination of two or more germline mutations within the framework and/or CDR regions, e.g., wherein certain individual residues are mutated to the corresponding residue of a particular germline sequence while certain other residues that differ from the original germline sequence are maintained or are mutated to the corresponding residue of a different germline sequence. Once obtained, antibodies and antigen-binding fragments that contain one or more germline mutations can be easily tested for one or more desired property such as, improved binding specificity, increased binding affinity, improved or enhanced antagonistic or agonistic biological properties (as the case may be), reduced immunogenicity, etc. Antibodies and antigen-binding fragments obtained in this general manner are encompassed within the present invention.

The present invention also includes anti-CD48 antibodies comprising variants of any of the HCVR, LCVR, and/or CDR amino acid sequences disclosed herein having one or more conservative substitutions. For example, the present invention includes anti-CD48 antibodies having HCVR, LCVR, and/or CDR amino acid sequences with, e.g., 10 or fewer, 8 or fewer, 6 or fewer, 4 or fewer, etc. conservative amino acid substitutions relative to any of the HCVR, LCVR, and/or CDR amino acid sequences disclosed herein.

The term "surface plasmon resonance", as used herein, refers to an optical phenomenon that allows for the analysis of real-time interactions by detection of alterations in protein concentrations within a biosensor matrix, for example using the BIAcore™ system (Biacore Life Sciences division of GE Healthcare, Piscataway, N.J.).

The term "$K_D$", as used herein, is intended to refer to the equilibrium dissociation constant of a particular antibody-antigen interaction.

The term "epitope" refers to an antigenic determinant that interacts with a specific antigen binding site in the variable region of an antibody molecule known as a paratope. A single antigen may have more than one epitope. Thus, different antibodies may bind to different areas on an antigen and may have different biological effects. Epitopes may be either conformational or linear. A conformational epitope is produced by spatially juxtaposed amino acids from different segments of the linear polypeptide chain. A linear epitope is one produced by adjacent amino acid residues in a polypeptide chain. In certain circumstance, an epitope may include moieties of saccharides, phosphoryl groups, or sulfonyl groups on the antigen.

The term "substantial identity" or "substantially identical," when referring to a nucleic acid or fragment thereof, indicates that, when optimally aligned with appropriate nucleotide insertions or deletions with another nucleic acid (or its complementary strand), there is nucleotide sequence identity in at least about 95%, and more preferably at least about 96%, 97%, 98% or 99% of the nucleotide bases, as measured by any well-known algorithm of sequence identity, such as FASTA, BLAST or Gap, as discussed below. A nucleic acid molecule having substantial identity to a reference nucleic acid molecule may, in certain instances, encode a polypeptide having the same or substantially similar amino acid sequence as the polypeptide encoded by the reference nucleic acid molecule.

As applied to polypeptides, the term "substantial similarity" or "substantially similar" means that two peptide sequences, when optimally aligned, such as by the programs GAP or BESTFIT using default gap weights, share at least 95% sequence identity, even more preferably at least 98% or 99% sequence identity. Preferably, residue positions which are not identical differ by conservative amino acid substitutions. A "conservative amino acid substitution" is one in which an amino acid residue is substituted by another amino acid residue having a side chain (R group) with similar chemical properties (e.g., charge or hydrophobicity). In general, a conservative amino acid substitution will not substantially change the functional properties of a protein. In cases where two or more amino acid sequences differ from each other by conservative substitutions, the percent sequence identity or degree of similarity may be adjusted upwards to correct for the conservative nature of the substitution. Means for making this adjustment are well-known to those of skill in the art. See, e.g., Pearson (1994) Methods Mol. Biol. 24: 307-331, herein incorporated by reference. Examples of groups of amino acids that have side chains with similar chemical properties include (1) aliphatic side chains: glycine, alanine, valine, leucine and isoleucine; (2) aliphatic-hydroxyl side chains: serine and threonine; (3) amide-containing side chains: asparagine and glutamine; (4) aromatic side chains: phenylalanine, tyrosine, and tryptophan; (5) basic side chains: lysine, arginine, and histidine; (6) acidic side chains: aspartate and glutamate, and (7) sulfur-containing side chains are cysteine and methionine. Preferred conservative amino acids substitution groups are: valine-leucine-isoleucine, phenylalanine-tyrosine, lysine-arginine, alanine-valine, glutamate-aspartate, and asparagine-glutamine. Alternatively, a conservative replacement is any change having a positive value in the PAM250 log-likelihood matrix disclosed in Gonnet et al. (1992) Science 256: 1443-1445, herein incorporated by reference. A "moderately conservative" replacement is any change having a nonnegative value in the PAM250 log-likelihood matrix.

Sequence similarity for polypeptides, which is also referred to as sequence identity, is typically measured using sequence analysis software. Protein analysis software matches similar sequences using measures of similarity assigned to various substitutions, deletions and other modifications, including conservative amino acid substitutions. For instance, GCG software contains programs such as Gap and Bestfit which can be used with default parameters to determine sequence homology or sequence identity between closely related polypeptides, such as homologous polypeptides from different species of organisms or between a wild type protein and a mutein thereof. See, e.g., GCG Version 6.1. Polypeptide sequences also can be compared using FASTA using default or recommended parameters, a program in GCG Version 6.1. FASTA (e.g., FASTA2 and FASTA3) provides alignments and percent sequence identity of the regions of the best overlap between the query and search sequences (Pearson (2000) supra). Another preferred algorithm when comparing a sequence of the invention to a database containing a large number of sequences from different organisms is the computer program BLAST, especially BLASTP or TBLASTN, using default parameters. See, e.g., Altschul et al. (1990) J. Mol. Biol. 215:403-410 and Altschul et al., (1997) Nucleic Acids Res. 25:3389-402, each herein incorporated by reference.

Biological Characteristics of the Antibodies

The antibodies of the present invention block the interaction between human CD48 and at least one CD48 receptor. As used herein, the expression "blocks the interaction between human CD48 and at least one CD48 receptor" means that, in an assay in which the physical interaction between CD48 and a CD48 receptor (e.g., human 2B4 and/or human CD2) can be detected and/or quantified, the addition of an antibody of the invention reduces the interaction between CD48 and the receptor by at least 50%. A non-limiting, exemplary assay that can be used to determine if an antibody blocks the interaction between human CD48 and a CD48 receptor (e.g., human 2B4) is illustrated in Example 5, herein. In this Example, antibodies are mixed with CD48 protein, and then the antibody/CD48 mixture is applied to a surface coated with 2B4 protein. After washing away unbound molecules, the amount of CD48 bound to the 2B4-coated surface is measured. By using varying amounts of antibody in this assay format, the amount of antibody required to block 50% of CD48 binding to 2B4 can be calculated and expressed as an $IC_{50}$ value. The present invention includes anti-CD48 antibodies that exhibit an $IC_{50}$ of less than about 400 pM when tested in a CD48/CD48 receptor binding assay as described above, or a substantially similar assay. For example, the invention includes anti-CD48 antibodies that exhibit an $IC_{50}$ of less than about 400, 300, 290, 280, 270, 260, 250, 240, 230, 220, 210, 200, 190, 180, 170, 160, 150, 140, 130, 120, 110, 100, 90, 80, 70, 60, 50, 40, 30, 20, 10, 18, 16, 14, 12, 10, 9, 8, 7, 6, 5, 4, 3, 2, or 1 pM when tested in a CD48/CD48 receptor binding assay as described above, or a substantially similar assay.

The antibodies of the present invention are also able to inhibit activation of primary human peripheral blood mononuclear cells (PBMCs). As used herein, the expression "inhibits activation of primary human peripheral blood mononuclear cells" means that, in an assay in which the activation of PBMCs can be detected and/or quantified (e.g., by measuring release of IFN-gamma or other cytokine), the addition of an antibody of the invention reduces the amount of IFN-gamma (or other cytokine) that is released by at least 50%. Non-limiting, exemplary assays that can be used to determine if an antibody inhibits activation of PBMCs are illustrated in Examples 6 and 7, herein. In one example, anti-CD48 antibody is added to isolated human PBMCs prior to activation of the PBMCs with agonist anti-CD3 and anti-CD28 antibodies. After a period of incubation, the amount of IFN-gamma released is measured. By using varying amounts of antibody in this assay format, the amount of antibody required to inhibit 50% of maximal IFN-gamma release can be calculated and expressed as an $IC_{50}$ value. The present invention includes anti-CD48 antibodies that exhibit an $IC_{50}$ of less than about 500 pM when tested in a PBMC activation assay as described above, or a substantially similar assay. For example, the invention includes anti-CD48 antibodies that exhibit an $IC_{50}$ of less than about 500, 400, 300, 290, 280, 270, 260, 250, 240, 230, 220, 210, 200, 190, 180, 170, 160, 150, 140, 130, 120, 110, 100, 90, 80, 70, 60, 50, 40, 30, 20, 10, 18, 16, 14, 12, 10, 9, 8, 7, 6, 5, 4, 3, 2, or 1 pM when tested in a PBMC activation assay as described above, or a substantially similar assay.

Epitope Mapping and Related Technologies

The human CD48 protein contains two immunoglobulin-like domains, referred to herein as "Ig domain 1" and "Ig domain 2". Ig domain 1 is the sequence of amino acids represented by amino acids 29 through 127 of SEQ ID NO:384, and Ig domain 2 is the sequence of amino acids represented by amino acids 132 through 212 of SEQ ID NO:384 (see FIG. 1).

The present invention includes anti-CD48 antibodies which bind specifically to an epitope within Ig domain 1 of human CD48. The epitope may consist of a single contiguous sequence of 3 or more (e.g., 3, 4, 5, 6, 7, 8, 9, 10, 11, 12, 13, 14, 15, 16, 17, 18, 19, 20 or more) amino acids located within Ig domain 1 of CD48. Alternatively, the epitope may consist of a plurality of non-contiguous amino acids (or amino acid sequences) located within Ig domain 1 of CD48. According to certain embodiments of the present invention, anti-CD48 antibodies are provided which interact with one or more amino acids located within amino acids 60 to 125 of SEQ ID NO:384. For example, the present invention includes anti-CD48 antibodies which interact with one or more amino acids located within amino acids 60 to 68 and/or 107 to 125 of SEQ ID NO:384.

Various techniques known to persons of ordinary skill in the art can be used to determine whether an antibody "interacts with one or more amino acids" within a polypeptide or protein. Exemplary techniques include, e.g., routine cross-blocking assay such as that described *Antibodies*, Harlow and Lane (Cold Spring Harbor Press, Cold Spring Harb., N.Y.), alanine scanning mutational analysis, peptide blots analysis (Reineke, 2004, Methods Mol Biol 248:443-463), and peptide cleavage analysis. In addition, methods such as epitope excision, epitope extraction and chemical modification of antigens can be employed (Tomer, 2000, Protein Science 9:487-496). Another method that can be used to identify the amino acids within a polypeptide with which an antibody interacts is hydrogen/deuterium exchange detected by mass spectrometry. (See, e.g., Example 4 herein). In general terms, the hydrogen/deuterium exchange method involves deuterium-labeling the protein of interest, followed by binding the antibody to the deuterium-labeled protein. Next, the protein/antibody complex is transferred to water to allow hydrogen-deuterium exchange to occur at all residues except for the residues protected by the antibody (which remain deuterium-labeled). After dissociation of the antibody, the target protein is subjected to protease cleavage and mass spectrometry analysis, thereby revealing the deuterium-labeled residues which correspond to the specific amino acids with which the antibody interacts. See, e.g., Ehring (1999) *Analytical Biochemistry* 267(2):252-259; Engen and Smith (2001) *Anal. Chem.* 73:256A-265A.

The present invention further includes anti-CD48 antibodies that bind to the same epitope as any of the specific exemplary antibodies described herein (e.g., H4H1789 Pa, H4H1763N, H2M1707N, H2M1709N, H4H1770N, H4H1771N, etc.). Likewise, the present invention also includes anti-CD48 antibodies that compete for binding to CD48 or a CD48 fragment with any of the specific exemplary antibodies described herein (e.g., H4H1789 Pa, H4H1763N, H2M1707N, H2M1709N, H4H1770N, H4H1771N, etc.).

One can easily determine whether an antibody binds to the same epitope as, or competes for binding with, a reference anti-CD48 antibody by using routine methods known in the art. For example, to determine if a test antibody binds to the same epitope as a reference anti-CD48 antibody of the invention, the reference antibody is allowed to bind to a CD48 protein or peptide under saturating conditions. Next, the ability of a test antibody to bind to the CD48 molecule is assessed. If the test antibody is able to bind to CD48 following saturation binding with the reference anti-CD48 antibody, it can be concluded that the test antibody binds to a different epitope than the reference anti-CD48 antibody. On the other hand, if the test antibody is not able to bind to the CD48 molecule following saturation binding with the reference anti-CD48 antibody, then the test antibody may bind to the same epitope as the epitope bound by the reference anti-CD48 antibody of the invention. Additional routine experimentation (e.g., peptide mutation and binding analyses) can then be carried out to confirm whether the observed lack of binding of the test antibody is in fact due to binding to the same epitope as the reference antibody or if steric blocking (or another phenomenon) is responsible for the lack of observed binding. Experiments of this sort can be performed using ELISA, RIA, Biacore, flow cytometry or any other quantitative or qualitative antibody-binding assay available in the art. In accordance with certain embodiments of the present invention, two antibodies bind to the same (or overlapping) epitope if, e.g., a 1-, 5-, 10-, 20- or 100-fold excess of one antibody inhibits binding of the other by at least 50% but preferably 75%, 90% or even 99% as measured in a competitive binding assay (see, e.g., Junghans et al., Cancer Res. 1990:50:1495-1502). Alternatively, two antibodies are deemed to bind to the same epitope if essentially all amino acid mutations in the antigen that reduce or eliminate binding of one antibody reduce or eliminate binding of the other. Two antibodies are deemed to have "overlapping epitopes" if only a subset of the amino acid mutations that reduce or eliminate binding of one antibody reduce or eliminate binding of the other.

To determine if an antibody competes for binding with a reference anti-CD48 antibody, the above-described binding methodology is performed in two orientations: In a first orientation, the reference antibody is allowed to bind to a CD48 molecule under saturating conditions followed by assessment of binding of the test antibody to the CD48 molecule. In a second orientation, the test antibody is allowed to bind to a CD48 molecule under saturating conditions followed by assessment of binding of the reference antibody to the CD48 molecule. If, in both orientations, only the first (saturating) antibody is capable of binding to the CD48 molecule, then it is concluded that the test antibody and the reference antibody compete for binding to CD48. As will be appreciated by a person of ordinary skill in the art, an antibody that competes for binding with a reference antibody may not necessarily bind to the same epitope as the reference antibody, but may sterically block binding of the reference antibody by binding an overlapping or adjacent epitope.

Preparation of Human Antibodies

Methods for generating monoclonal antibodies, including fully human monoclonal antibodies are known in the art. Any such known methods can be used in the context of the present invention to make human antibodies that specifically bind to human CD48.

Using VELOCIMMUNE™ technology or any other known method for generating monoclonal antibodies, high affinity chimeric antibodies to CD48 are initially isolated having a human variable region and a mouse constant region. As in the experimental section below, the antibodies are characterized and selected for desirable characteristics, including affinity, selectivity, epitope, etc. The mouse constant regions are replaced with a desired human constant region to generate the fully human antibody of the invention, for example wild-type or modified IgG1 or IgG4. While the constant region selected may vary according to specific use, high affinity antigen-binding and target specificity characteristics reside in the variable region.

Bioequivalents

The anti-CD48 antibodies and antibody fragments of the present invention encompass proteins having amino acid sequences that vary from those of the described antibodies but that retain the ability to bind human CD48. Such variant antibodies and antibody fragments comprise one or more additions, deletions, or substitutions of amino acids when compared to parent sequence, but exhibit biological activity that is essentially equivalent to that of the described antibodies. Likewise, the anti-CD48 antibody-encoding DNA sequences of the present invention encompass sequences that comprise one or more additions, deletions, or substitutions of nucleotides when compared to the disclosed sequence, but that encode an anti-CD48 antibody or antibody fragment that is essentially bioequivalent to an anti-CD48 antibody or antibody fragment of the invention. Examples of such variant amino acid and DNA sequences are discussed above.

Two antigen-binding proteins, or antibodies, are considered bioequivalent if, for example, they are pharmaceutical equivalents or pharmaceutical alternatives whose rate and extent of absorption do not show a significant difference when administered at the same molar dose under similar experimental conditions, either single does or multiple dose. Some antibodies will be considered equivalents or pharmaceutical alternatives if they are equivalent in the extent of their absorption but not in their rate of absorption and yet may be considered bioequivalent because such differences in the rate of absorption are intentional and are reflected in the labeling, are not essential to the attainment of effective body drug concentrations on, e.g., chronic use, and are considered medically insignificant for the particular drug product studied.

In one embodiment, two antigen-binding proteins are bioequivalent if there are no clinically meaningful differences in their safety, purity, and potency.

In one embodiment, two antigen-binding proteins are bioequivalent if a patient can be switched one or more times between the reference product and the biological product without an expected increase in the risk of adverse effects, including a clinically significant change in immunogenicity, or diminished effectiveness, as compared to continued therapy without such switching.

In one embodiment, two antigen-binding proteins are bioequivalent if they both act by a common mechanism or mechanisms of action for the condition or conditions of use, to the extent that such mechanisms are known.

Bioequivalence may be demonstrated by in vivo and in vitro methods. Bioequivalence measures include, e.g., (a) an in vivo test in humans or other mammals, in which the concentration of the antibody or its metabolites is measured in blood, plasma, serum, or other biological fluid as a function of time; (b) an in vitro test that has been correlated with and is reasonably predictive of human in vivo bioavailability data; (c) an in vivo test in humans or other mammals in which the appropriate acute pharmacological effect of the antibody (or its target) is measured as a function of time; and (d) in a well-controlled clinical trial that establishes safety, efficacy, or bioavailability or bioequivalence of an antibody.

Bioequivalent variants of anti-CD48 antibodies of the invention may be constructed by, for example, making various substitutions of residues or sequences or deleting terminal or internal residues or sequences not needed for biological activity. For example, cysteine residues not essential for biological activity can be deleted or replaced with other amino acids to prevent formation of unnecessary or incorrect intramolecular disulfide bridges upon renaturation. In other contexts, bioequivalent antibodies may include anti-CD48 antibody variants comprising amino acid changes which modify the glycosylation characteristics of the antibodies, e.g., mutations which eliminate or remove glycosylation.

Species Selectivity and Species Cross-Reactivity

According to certain embodiments of the invention, the anti-CD48 antibodies bind to human CD48 but not to CD48 from other species. The present invention also includes anti-CD48 antibodies that bind to human CD48 and to CD48 from one or more non-human species. For example, the anti-CD48 antibodies of the invention may bind to human CD48 and may bind or not bind, as the case may be, to one or more of mouse, rat, guinea pig, hamster, gerbil, pig, cat, dog, rabbit, goat, sheep, cow, horse, camel, cynomologous, marmoset, rhesus or chimpanzee CD48.

Immunoconjugates

The invention encompasses anti-CD48 monoclonal antibodies conjugated to a therapeutic moiety ("immunoconjugate"), such as a cytotoxin, a chemotherapeutic drug, an immunosuppressant or a radioisotope. Cytotoxic agents include any agent that is detrimental to cells. Examples of suitable cytotoxic agents and chemotherapeutic agents for forming immunoconjugates are known in the art, (see for example, WO 05/103081).

Multispecific Antibodies

The antibodies of the present invention may be monospecific, bi-specific, or multispecific. Multispecific antibodies may be specific for different epitopes of one target polypeptide or may contain antigen-binding domains specific for more than one target polypeptide. See, e.g., Tutt et al., 1991, J. Immunol. 147:60-69; Kufer et al., 2004, Trends Biotechnol. 22:238-244. The anti-CD48 antibodies of the present invention can be linked to or co-expressed with another functional molecule, e.g., another peptide or protein. For example, an antibody or fragment thereof can be functionally linked (e.g., by chemical coupling, genetic fusion, noncovalent association or otherwise) to one or more other molecular entities, such as another antibody or antibody fragment to produce a bi-specific or a multispecific antibody with a second binding specificity. For example, the present invention includes bi-specific antibodies wherein one arm of an immunoglobulin is specific for human CD48 or a fragment thereof, and the other arm of the immunoglobulin is specific for a second therapeutic target or is conjugated to a therapeutic moiety such as a trypsin inhibitor.

An exemplary bi-specific antibody format that can be used in the context of the present invention involves the use of a first immunoglobulin (Ig) $C_H3$ domain and a second Ig $C_H3$ domain, wherein the first and second Ig $C_H3$ domains differ from one another by at least one amino acid, and wherein at least one amino acid difference reduces binding of the bispecific antibody to Protein A as compared to a bi-specific antibody lacking the amino acid difference. In one embodiment, the first Ig $C_H3$ domain binds Protein A and the second Ig $C_H3$ domain contains a mutation that reduces or abolishes Protein A binding such as an H95R modification (by IMGT exon numbering; H435R by EU numbering). The second $C_H3$ may further comprise a Y96F modification (by IMGT; Y436F by EU). Further modifications that may be found within the second $C_H3$ include: D16E, L18M, N44S, K52N, V57M, and V82I (by IMGT; D356E, L358M, N384S, K392N, V397M, and V422I by EU) in the case of IgG1 antibodies; N44S, K52N, and V82I (IMGT; N384S, K392N, and V422I by EU) in the case of IgG2 antibodies; and Q15R, N44S, K52N, V57M, R69K, E79Q, and V82I (by IMGT; Q355R, N384S, K392N, V397M, R409K, E419Q, and V422I by EU) in the case of IgG4 antibodies. Variations on the bi-specific antibody format described above are contemplated within the scope of the present invention.

Therapeutic Formulation and Administration

The invention provides pharmaceutical compositions comprising the anti-CD48 antibodies or antigen-binding fragments thereof of the present invention. The pharmaceutical compositions of the invention are formulated with suitable carriers, excipients, and other agents that provide improved transfer, delivery, tolerance, and the like. A multitude of appropriate formulations can be found in the formulary known to all pharmaceutical chemists: Remington's Pharmaceutical Sciences, Mack Publishing Company, Easton, Pa. These formulations include, for example, powders, pastes, ointments, jellies, waxes, oils, lipids, lipid (cationic or anionic) containing vesicles (such as LIPOFECTIN™), DNA conjugates, anhydrous absorption pastes, oil-in-water and water-in-oil emulsions, emulsions carbowax (polyethylene glycols of various molecular weights), semi-solid gels, and semi-solid mixtures containing carbowax. See also Powell et al. "Compendium of excipients for parenteral formulations" PDA (1998) J Pharm Sci Technol 52:238-311.

The dose of antibody administered to a patient may vary depending upon the age and the size of the patient, target disease, conditions, route of administration, and the like. The preferred dose is typically calculated according to body weight or body surface area. When an antibody of the present invention is used for treating a condition or disease associated with CD48 activity in an adult patient, it may be advantageous to intravenously administer the antibody of the present invention normally at a single dose of about 0.01 to about 20 mg/kg body weight, more preferably about 0.02 to about 7, about 0.03 to about 5, or about 0.05 to about 3 mg/kg body weight. Depending on the severity of the condition, the frequency and the duration of the treatment can be adjusted. Effective dosages and schedules for administering CD48 antibodies may be determined empirically; for example, patient progress can be monitored by periodic assessment, and the dose adjusted accordingly. Moreover, interspecies scaling of dosages can be performed using well-known methods in the art (e.g., Mordenti et al., 1991, *Pharmaceut. Res.* 8:1351).

Various delivery systems are known and can be used to administer the pharmaceutical composition of the invention, e.g., encapsulation in liposomes, microparticles, microcapsules, recombinant cells capable of expressing the mutant viruses, receptor mediated endocytosis (see, e.g., Wu et al., 1987, J. Biol. Chem. 262:4429-4432). Methods of introduction include, but are not limited to, intradermal, intramuscular, intraperitoneal, intravenous, subcutaneous, intranasal, epidural, and oral routes. The composition may be administered by any convenient route, for example by infusion or bolus injection, by absorption through epithelial or mucocutaneous linings (e.g., oral mucosa, rectal and intestinal mucosa, etc.) and may be administered together with other biologically active agents. Administration can be systemic or local.

A pharmaceutical composition of the present invention can be delivered subcutaneously or intravenously with a standard needle and syringe. In addition, with respect to subcutaneous delivery, a pen delivery device readily has applications in delivering a pharmaceutical composition of the present invention. Such a pen delivery device can be reusable or disposable. A reusable pen delivery device generally utilizes a replaceable cartridge that contains a pharmaceutical composition. Once all of the pharmaceutical composition within the cartridge has been administered and the cartridge is empty, the empty cartridge can readily be discarded and replaced with a new cartridge that contains the pharmaceutical composition. The pen delivery device can then be reused. In a disposable pen delivery device, there is no replaceable cartridge. Rather, the disposable pen delivery device comes prefilled with the pharmaceutical composition held in a reservoir within the device. Once the reservoir is emptied of the pharmaceutical composition, the entire device is discarded.

Numerous reusable pen and autoinjector delivery devices have applications in the subcutaneous delivery of a pharmaceutical composition of the present invention. Examples include, but are not limited to AUTOPEN™ (Owen Mumford, Inc., Woodstock, UK), DISETRONIC™ pen (Disetronic Medical Systems, Bergdorf, Switzerland), HUMALOG MIX 75/25™ pen, HUMALOG™ pen, HUMALIN 70/30™ pen (Eli Lilly and Co., Indianapolis, Ind.), NOVOPEN™ I, II and III (Novo Nordisk, Copenhagen, Denmark), NOVOPEN JUNIOR™ (Novo Nordisk, Copenhagen, Denmark), BD™ pen (Becton Dickinson, Franklin Lakes, N.J.), OPTIPEN™, OPTIPEN PRO™, OPTIPEN STARLETT™, and OPTICLIK™ (sanofi-aventis, Frankfurt, Germany), to name only a few. Examples of disposable pen delivery devices having applications in subcutaneous delivery of a pharmaceutical composition of the present invention include, but are not limited to the SOLOSTAR™ pen (sanofi-aventis), the FLEXPEN™ (Novo Nordisk), and the KWIKPEN™ (Eli Lilly), the SURECLICK™ Autoinjector (Amgen, Thousand Oaks, Calif.), the PENLET™ (Haselmeier, Stuttgart, Germany), the EPIPEN (Dey, L. P.), and the HUMIRA™ Pen (Abbott Labs, Abbott Park Ill.), to name only a few.

In certain situations, the pharmaceutical composition can be delivered in a controlled release system. In one embodiment, a pump may be used (see Langer, supra; Sefton, 1987, CRC Crit. Ref. Biomed. Eng. 14:201). In another embodiment, polymeric materials can be used; see, Medical Applications of Controlled Release, Langer and Wise (eds.), 1974, CRC Pres., Boca Raton, Fla. In yet another embodiment, a controlled release system can be placed in proximity of the composition's target, thus requiring only a fraction of the systemic dose (see, e.g., Goodson, 1984, in Medical Applications of Controlled Release, supra, vol. 2, pp. 115-138). Other controlled release systems are discussed in the review by Langer, 1990, Science 249:1527-1533.

The injectable preparations may include dosage forms for intravenous, subcutaneous, intracutaneous and intramuscular injections, drip infusions, etc. These injectable preparations may be prepared by methods publicly known. For example, the injectable preparations may be prepared, e.g., by dissolving, suspending or emulsifying the antibody or its salt described above in a sterile aqueous medium or an oily medium conventionally used for injections. As the aqueous medium for injections, there are, for example, physiological saline, an isotonic solution containing glucose and other auxiliary agents, etc., which may be used in combination with an appropriate solubilizing agent such as an alcohol (e.g., ethanol), a polyalcohol (e.g., propylene glycol, polyethylene glycol), a nonionic surfactant [e.g., polysorbate 80, HCO-50 (polyoxyethylene (50 mol) adduct of hydrogenated castor oil)], etc. As the oily medium, there are employed, e.g., sesame oil, soybean oil, etc., which may be used in combination with a solubilizing agent such as benzyl benzoate, benzyl alcohol, etc. The injection thus prepared is preferably filled in an appropriate ampoule.

Advantageously, the pharmaceutical compositions for oral or parenteral use described above are prepared into dosage forms in a unit dose suited to fit a dose of the active ingredients. Such dosage forms in a unit dose include, for example, tablets, pills, capsules, injections (ampoules), suppositories, etc. The amount of the aforesaid antibody contained is generally about 5 to about 500 mg per dosage form in a unit dose; especially in the form of injection, it is preferred that the aforesaid antibody is contained in about 5 to about 100 mg and in about 10 to about 250 mg for the other dosage forms.

Therapeutic Uses of the Antibodies

The antibodies of the invention are useful, inter alia, for the treatment, prevention and/or amelioration of any disease or disorder associated with or mediated by CD48 activity or treatable by blocking the interaction between CD48 and a CD48 receptor. Exemplary diseases and disorders that can be treated with the anti-CD48 antibodies of the present invention include, e.g., asthma, allergy, atopic dermatitis, conjunctivitis, inflammatory bowel disease (e.g., ulcerative colitis), celiac disease, and cancer (e.g., blood cell cancer, brain cancer, breast cancer, colon cancer, head and neck cancer, liver cancer, lung cancer, ovarian cancer, pancreatic cancer, prostate cancer, skin cancer, stomach cancer, etc.). The anti-CD48 antibodies of the present invention can also be administered to patients to treat psoriasis. Other diseases and disorders that can be treated with the anti-CD48 antibodies of the present invention include, e.g., systemic lupus erythematosis (SLE), rheumatoid arthritis, graft-versus-host disease (GvHD) (e.g., chronic GvHD or acute GvHD), and transplant rejection.

Combination Therapies

The present invention includes therapeutic administration regimens which comprise administering an anti-CD48 antibody of the present invention in combination with at least one additional therapeutically active component. Non-limiting examples of such additional therapeutically active components include other CD48 antagonists (e.g., a second anti-CD48 antibody or small molecule inhibitor of CD48), cytokine inhibitors (e.g., an interleukin-1 (IL-1) inhibitor (such as rilonacept or anakinra, a small molecule IL-1 antagonist, or an anti-IL-1 antibody); IL-18 inhibitor (such as a small molecule IL-18 antagonist or an anti-IL-18 antibody); IL-4 inhibitor (such as a small molecule IL-4 antagonist, an anti-IL-4 antibody or an anti-IL-4 receptor antibody); IL-6 inhibitor (such as a small molecule IL-6 antagonist, an anti-IL-6 antibody or an anti-IL-6 receptor antibody); aspirin; NSAIDs; steroids (e.g., prednisone, methotrexate, etc.); low dose cyclosporine A; tumor necrosis factor (TNF) or TNF receptor inhibitors (e.g., a small molecule TNF or TNFR antagonist or an anti-TNF or TNFR antibody); uric acid synthesis inhibitors (e.g., allopurinol); uric acid excretion promoters (e.g., probenecid, sulfinpyrazone, benzbromarone, etc.); other inflammatory inhibitors (e.g., inhibitors of caspase-1, p38, IKK1/2, CTLA-4Ig, etc.); and/or corticosteroids. The additional therapeutically active component(s) may be administered prior to, concurrent with, or after the administration of an anti-CD48 antibody of the present invention (for purposes of the present disclosure, such administration regimens are considered the administration of an anti-CD48 antibody "in combination with" a therapeutically active component of the invention).

Diagnostic Uses of the Antibodies

The anti-CD48 antibodies of the present invention may also be used to detect and/or measure CD48 in a sample, e.g., for diagnostic purposes. For example, an anti-CD48 antibody, or fragment thereof, may be used to diagnose a condition or disease characterized by aberrant expression (e.g., over-expression, under-expression, lack of expression, etc.) of CD48. Exemplary diagnostic assays for CD48 may comprise, e.g., contacting a sample, obtained from a patient, with an anti-CD48 antibody of the invention, wherein the anti-CD48 antibody is labeled with a detectable label or reporter molecule. Alternatively, an unlabeled anti-CD48 antibody can be used in diagnostic applications in combination with a secondary antibody which is itself detectably labeled. The detectable label or reporter molecule can be a radioisotope, such as $^{3}$H, $^{14}$C, $^{32}$P, $^{35}$S, or $^{125}$I; a fluorescent or chemiluminescent moiety such as fluorescein isothiocyanate, or rhodamine; or an enzyme such as alkaline phosphatase, beta-galactosidase, horseradish peroxidase, or luciferase. Specific exemplary assays that can be used to detect or measure CD48 in a sample include enzyme-linked immunosorbent assay (ELISA), radioimmunoassay (RIA), and fluorescence-activated cell sorting (FACS).

Samples that can be used in CD48 diagnostic assays according to the present invention include any tissue or fluid sample obtainable from a patient which contains detectable quantities of CD48 protein, or fragments thereof, under normal or pathological conditions. Generally, levels of CD48 in a particular sample obtained from a healthy patient (e.g., a patient not afflicted with a disease or condition associated with abnormal CD48 levels or activity) will be measured to initially establish a baseline, or standard, level of CD48. This baseline level of CD48 can then be compared against the levels of CD48 measured in samples obtained from individuals suspected of having a CD48 related disease or condition.

EXAMPLES

The following examples are put forth so as to provide those of ordinary skill in the art with a complete disclosure and description of how to make and use the methods and compositions of the invention, and are not intended to limit the scope of what the inventors regard as their invention. Efforts have been made to ensure accuracy with respect to numbers used (e.g., amounts, temperature, etc.) but some experimental errors and deviations should be accounted for. Unless indicated otherwise, parts are parts by weight, molecular weight is average molecular weight, temperature is in degrees Centigrade, and pressure is at or near atmospheric.

Example 1

Generation of Human Antibodies to Human CD48

An immunogen comprising the ecto-domain of human CD48 (amino acids 27-220 of SEQ ID NO:384) was administered directly, with an adjuvant to stimulate the immune response, to a VELOCIMMUNE® mouse comprising DNA encoding human Immunoglobulin heavy and kappa light chain variable regions. The antibody immune response was monitored by a CD48-specific immunoassay. When a desired immune response was achieved splenocytes were harvested and fused with mouse myeloma cells to preserve their viability and form hybridoma cell lines. The hybridoma cell lines were screened and selected to identify cell lines that produce CD48-specific antibodies. Using this technique several anti-CD48 chimeric antibodies (i.e., antibodies possessing human variable domains and mouse constant domains) were obtained; exemplary antibodies generated in this manner were designated as follows: H2M1707N, H2M1709N, H2M1710N, H2M1712N, H2M1713N, H2M1763N, H2M1811N, H3M1766N, H2M1798N, and H2M1711N.

Anti-CD48 antibodies were also isolated directly from antigen-positive B cells without fusion to myeloma cells, as described in U.S. 2007/0280945A1, herein specifically incorporated by reference in its entirety. Using this method, several fully human anti-CD48 antibodies (i.e., antibodies possessing human variable domains and human constant domains) were obtained; exemplary antibodies generated in this manner were designated as follows: H4H1769Na, H4H1769 Pa, H4H1769Nb, H4H1769Pb, H4H1770N, H4H1770P, H4H1771N, H4H1771P, H4H1772N, H4H1772P, H4H1774N, H4H1774P, H4H1775N, H4H1775P, H4H1778N, H4H1778P, H4H1779N, H4H1779P, H4H1781N, H4H1781P, H4H1789Na, H4H1789 Pa, H4H1789Nb, H4H1789Pb.

The biological properties of the exemplary anti-CD48 antibodies generated in accordance with the methods of this Example are described in detail in the Examples set forth below.

Example 2

Heavy and Light Chain Variable Region Amino Acid Sequences

Table 1 sets forth the heavy and light chain variable region amino acid sequence pairs of selected anti-CD48 antibodies and their corresponding antibody identifiers. The N, P and G designations refer to antibodies having heavy and light chains with identical CDR sequences but with sequence variations in regions that fall outside of the CDR sequences (i.e., in the framework regions). Thus, N, P and G variants of a particular antibody have identical CDR sequences within their heavy and light chain variable regions but differ from one another within their framework regions. The H2M, H3M, H4H, etc. prefixes on the antibody designations used herein indicate the particular Fc region of the antibody. For example, an "H2M" antibody has a mouse IgG2 Fc, whereas an "H4H" antibody has a human IgG4 Fc. As will be appreciated by a person of ordinary skill in the art, an H2M or H3M antibody can be converted to an H4H antibody, and vice versa, but the variable domains (including the CDRs) will remain the same.

TABLE 1

| Antibody Designation | SEQ ID NOs: | | | | | | | |
| --- | --- | --- | --- | --- | --- | --- | --- | --- |
| | HCVR | HCDR1 | HCDR2 | HCDR3 | LCVR | LCDR1 | LCDR2 | LCDR3 |
| H2M1707N | 2 | 4 | 6 | 8 | 10 | 12 | 14 | 16 |
| H2M1709N | 18 | 20 | 22 | 24 | 26 | 28 | 30 | 32 |
| H2M1710N | 34 | 36 | 38 | 40 | 42 | 44 | 46 | 48 |
| H2M1712N | 50 | 52 | 54 | 56 | 58 | 60 | 62 | 64 |
| H2M1713N | 66 | 68 | 70 | 72 | 74 | 76 | 78 | 80 |
| H2M1763N | 82 | 84 | 86 | 88 | 90 | 92 | 94 | 96 |
| H2M1764N | 98 | 100 | 102 | 104 | 106 | 108 | 110 | 112 |
| H2M1811N | 114 | 116 | 118 | 120 | 122 | 124 | 126 | 128 |
| H3M1766N | 130 | 132 | 134 | 136 | 138 | 140 | 142 | 144 |
| H4H1769Na | 162 | 164 | 166 | 168 | 170 | 172 | 174 | 176 |
| H4H1769Pa | 178 | 164 | 166 | 168 | 180 | 172 | 174 | 176 |
| H4H1769Nb | 162 | 164 | 166 | 168 | 182 | 184 | 186 | 188 |
| H4H1769Pb | 178 | 164 | 166 | 168 | 190 | 184 | 186 | 188 |
| H4H1770N | 192 | 194 | 196 | 198 | 200 | 202 | 204 | 206 |
| H4H1770P | 208 | 194 | 196 | 198 | 210 | 202 | 204 | 206 |
| H4H1771N | 212 | 214 | 216 | 218 | 220 | 222 | 224 | 226 |
| H4H1771P | 228 | 214 | 216 | 218 | 230 | 222 | 224 | 226 |
| H4H1772N | 232 | 234 | 236 | 238 | 240 | 242 | 244 | 246 |
| H4H1772P | 248 | 234 | 236 | 238 | 250 | 242 | 244 | 246 |
| H4H1774N | 252 | 254 | 256 | 258 | 260 | 262 | 264 | 266 |
| H4H1774P | 268 | 254 | 256 | 258 | 270 | 262 | 264 | 266 |
| H4H1775N | 272 | 274 | 276 | 278 | 280 | 282 | 284 | 286 |
| H4H1775P | 288 | 274 | 276 | 278 | 290 | 282 | 284 | 286 |
| H4H1778N | 292 | 294 | 296 | 298 | 300 | 302 | 304 | 306 |
| H4H1778P | 308 | 294 | 296 | 298 | 310 | 302 | 304 | 306 |
| H4H1779N | 312 | 314 | 316 | 318 | 320 | 322 | 324 | 326 |
| H4H1779P | 328 | 314 | 316 | 318 | 330 | 322 | 324 | 326 |
| H4H1781N | 332 | 334 | 336 | 338 | 340 | 342 | 344 | 346 |
| H4H1781P | 348 | 334 | 336 | 338 | 350 | 342 | 344 | 346 |
| H4H1789Na | 352 | 354 | 356 | 358 | 360 | 362 | 364 | 366 |

TABLE 1-continued

| Antibody Designation | SEQ ID NOs: | | | | | | | |
|---|---|---|---|---|---|---|---|---|
| | HCVR | HCDR1 | HCDR2 | HCDR3 | LCVR | LCDR1 | LCDR2 | LCDR3 |
| H4H1789Pa | 368 | 354 | 356 | 358 | 370 | 362 | 364 | 366 |
| H4H1789Nb | 352 | 354 | 356 | 358 | 372 | 374 | 376 | 378 |
| H4H1789Pb | 368 | 354 | 356 | 358 | 380 | 374 | 376 | 378 |

Example 3

Antibody Binding to Soluble CD48 Determined by Surface Plasmon Resonance

Binding affinities and kinetic constants of human monoclonal anti-hCD48 antibodies binding to human and monkey soluble recombinant CD48 were determined by surface plasmon resonance at both 25° C. and 37° C. and for both monomeric and dimeric configurations of CD48. Measurements were conducted on a T100-2 BIACORE™ instrument (Biacore Life Sciences division of GE Healthcare, Piscataway, N.J.). Antibodies (either with mouse Fc [designated "H2M" or "H3M"] or human IgG4 Fc [designated "H4H"] were captured through an anti-Fc chip surface, and CD48 was flowed over the surface either in a monomeric (soluble CD48 expressed with a myc-myc-hexa-histidine C-terminal tag [mmH]) or dimeric (soluble CD48 expressed with a C-terminal Fc fusion [mFc]) format. The amino acid sequence identifiers of the reagents used in this Example are set forth in Table 2.

TABLE 2

| Construct | SEQ ID NO: |
|---|---|
| Monomeric human CD48-mmH | 385 |
| Monomeric monkey CD48-mmH | 386 |
| Dimeric human CD48-mFc | 387 |
| Dimeric monkey CD48-mFc | 388 |

The soluble CD48 was applied to the flow cell in separate injections at different concentrations, and kinetic association ($k_a$) and dissociation ($k_d$) rate constants were determined by fits to the kinetic binding data using Biacore software. Binding dissociation equilibrium constants and dissociation half-times were calculated from the kinetic rate constants as: $K_D = k_d/k_a$; $t_{1/2} = (\ln 2/k_d)$ (units: $ka = M^{-1} * s^{-1}$; $kd = s^{-1}$; $K_D = M$; $T\frac{1}{2} = min$) (Tables 3-6).

TABLE 3

| | (25° C.) | | | | | | | |
|---|---|---|---|---|---|---|---|---|
| | monomeric human CD48 | | | | dimeric human CD48 | | | |
| Antibody | ka | kd | $K_D$ | T½ | ka | kd | $K_D$ | T½ |
| H2M1707N | 1.31E+05 | 6.42E−04 | 4.92E−09 | 18 | 7.14E+05 | 6.59E−05 | 9.23E−11 | 175 |
| H4H1707N | 1.68E+05 | 6.01E−04 | 3.57E−09 | 19 | 3.85E+05 | 2.83E−05 | 7.36E−11 | 408 |
| H2M1709N | 2.92E+05 | 5.80E−03 | 1.98E−08 | 2 | 9.28E+05 | 2.88E−04 | 3.11E−10 | 40 |
| H2M1710N | 3.73E+04 | 1.46E−03 | 3.91E−08 | 8 | 1.12E+05 | 9.38E−05 | 8.41E−10 | 123 |
| H2M1711N | 6.92E+05 | 1.13E−03 | 1.64E−09 | 10 | 1.64E+06 | 1.02E−04 | 6.23E−11 | 113 |
| H2M1712N | 5.24E+05 | 6.19E−03 | 1.18E−08 | 2 | 1.84E+06 | 5.30E−04 | 2.88E−10 | 22 |
| H2M1713N | 1.61E+05 | 2.17E−04 | 1.35E−09 | 53 | 8.26E+05 | 1.11E−05 | 1.34E−11 | 1043 |
| H4H1713N | 1.94E+05 | 1.74E−04 | 8.93E−10 | 67 | 8.94E+05 | 1.90E−05 | 2.12E−11 | 609 |
| H2M1763N | 5.48E+05 | 6.48E−03 | 1.18E−08 | 2 | 1.95E+06 | 4.99E−04 | 2.56E−10 | 23 |
| H4H1763N | 7.69E+05 | 6.31E−03 | 8.20E−09 | 2 | 2.05E+06 | 5.48E−05 | 2.68E−11 | 211 |
| H2M1764N | 1.21E+05 | 2.85E−03 | 2.35E−08 | 4 | 2.59E+05 | 2.66E−04 | 1.03E−09 | 43 |
| H4H1764N | 1.05E+05 | 2.48E−03 | 2.36E−08 | 5 | 2.68E+05 | 6.05E−05 | 2.26E−10 | 191 |
| H3M1766N | 6.34E+04 | 1.77E−04 | 2.79E−09 | 65 | 1.29E+05 | 6.57E−05 | 5.10E−10 | 176 |
| H4H1769P | 1.93E+05 | 7.79E−05 | 4.03E−10 | 148 | 9.69E+05 | 1.08E−05 | 1.11E−11 | 1071 |
| H4H1770P | 5.89E+05 | 1.53E−04 | 2.59E−10 | 76 | 1.71E+06 | 5.54E−06 | 3.25E−12 | 2084 |
| H4H1771P | 8.05E+05 | 2.09E−04 | 2.60E−10 | 55 | 2.07E+06 | 1.52E−05 | 7.36E−12 | 759 |
| H4H1772P | 1.27E+05 | 1.76E−04 | 1.38E−09 | 66 | 3.76E+05 | 1.29E−05 | 3.44E−11 | 894 |
| H4H1774P | 1.04E+05 | 4.72E−05 | 4.54E−10 | 245 | 3.11E+05 | 4.65E−06 | 1.49E−11 | 2486 |
| H4H1775P | 1.45E+05 | 4.92E−05 | 3.40E−10 | 235 | 7.34E+05 | 1.31E−05 | 1.79E−11 | 881 |
| H4H1778P | 9.86E+04 | 4.69E−05 | 4.76E−10 | 246 | 2.94E+05 | 8.95E−06 | 3.04E−11 | 1291 |
| H4H1779P | 1.58E+05 | 3.90E−05 | 2.46E−10 | 296 | 7.74E+05 | 1.17E−05 | 1.51E−11 | 990 |
| H4H1781P | 1.70E+05 | 3.30E−05 | 1.94E−10 | 351 | 8.54E+05 | 1.23E−05 | 1.44E−11 | 940 |
| H4H1789Pa | 1.43E+05 | 4.58E−04 | 3.20E−09 | 25 | 3.82E+05 | 3.66E−05 | 9.58E−11 | 315 |
| H2M1798N | 9.14E+05 | 2.47E−03 | 2.70E−09 | 5 | 2.05E+06 | 2.71E−04 | 1.32E−10 | 43 |
| H2M1811N | 5.00E+04 | 8.49E−04 | 1.70E−08 | 14 | 1.44E+05 | 2.30E−04 | 1.60E−09 | 50 |

TABLE 4

(37° C.)

| Antibody | monomeric human CD48 | | | | dimeric human CD48 | | | |
|---|---|---|---|---|---|---|---|---|
| | ka | kd | $K_D$ | T½ | ka | kd | $K_D$ | T½ |
| H2M1707N | 2.14E+05 | 3.14E−03 | 1.47E−08 | 4 | 9.20E+05 | 2.27E−04 | 2.47E−10 | 51 |
| H4H1707N | 2.84E+05 | 2.73E−03 | 9.63E−09 | 4 | 9.81E+05 | 6.42E−05 | 6.54E−11 | 180 |
| H2M1709N | 1.14E+06 | 4.00E−02 | 3.51E−08 | 0 | 1.52E+06 | 3.77E−04 | 2.48E−10 | 31 |
| H2M1710N | 3.40E+04 | 5.20E−03 | 1.53E−07 | 2 | 4.81E+05 | 4.26E−04 | 8.85E−10 | 27 |
| H2M1711N | 9.26E+05 | 3.02E−03 | 3.26E−09 | 4 | 2.08E+06 | 2.39E−04 | 1.15E−10 | 48 |
| H2M1712N | 8.46E+05 | 1.40E−02 | 1.66E−08 | 1 | 2.72E+06 | 6.85E−04 | 2.52E−10 | 17 |
| H2M1713N | 2.35E+05 | 6.44E−04 | 2.74E−09 | 18 | 1.25E+06 | 8.27E−05 | 6.63E−11 | 140 |
| H4H1713N | 2.86E+05 | 6.36E−04 | 2.23E−09 | 18 | 1.26E+06 | 4.53E−05 | 3.60E−11 | 255 |
| H2M1763N | 1.49E+06 | 2.01E−02 | 1.35E−08 | 1 | 3.02E+06 | 8.83E−04 | 2.93E−10 | 13 |
| H4H1763N | 1.33E+06 | 1.69E−02 | 1.27E−08 | 1 | 2.35E+06 | 6.28E−05 | 2.67E−11 | 184 |
| H2M1764N | 1.69E+05 | 1.60E−02 | 9.47E−08 | 1 | 7.02E+05 | 4.12E−04 | 5.86E−10 | 28 |
| H4H1764N | 1.05E+05 | 1.14E−02 | 1.09E−07 | 1 | 3.01E+05 | 9.94E−05 | 3.30E−10 | 116 |
| H3M1766N | 1.61E+05 | 6.20E−04 | 3.84E−09 | 19 | 9.49E+05 | 3.24E−04 | 3.42E−10 | 36 |
| H4H1769P | 2.25E+05 | 3.14E−04 | 1.40E−09 | 37 | 1.21E+06 | 3.63E−05 | 3.01E−11 | 319 |
| H4H1770P | 8.04E+05 | 5.33E−04 | 6.62E−10 | 22 | 2.23E+06 | 1.33E−04 | 1.38E−11 | 375 |
| H4H1771P | 1.12E+06 | 5.47E−04 | 4.88E−10 | 21 | 2.89E+06 | 4.81E−05 | 1.66E−11 | 240 |
| H4H1772P | 1.72E+05 | 1.02E−03 | 5.94E−09 | 11 | 9.20E+05 | 5.98E−05 | 6.50E−11 | 193 |
| H4H1774P | 1.30E+05 | 1.07E−04 | 8.24E−10 | 108 | 3.63E+05 | 1.60E−05 | 4.39E−11 | 724 |
| H4H1775P | 1.77E+05 | 9.48E−05 | 5.36E−10 | 122 | 5.22E+05 | 2.27E−05 | 4.34E−11 | 509 |
| H4H1778P | 1.35E+05 | 1.13E−04 | 8.37E−10 | 102 | 4.73E+05 | 3.53E−05 | 7.46E−11 | 327 |
| H4H1779P | 2.07E+05 | 1.02E−04 | 4.95E−10 | 113 | 7.72E+05 | 4.59E−05 | 5.94E−11 | 252 |
| H4H1781P | 2.26E+05 | 1.01E−04 | 4.48E−10 | 114 | 8.12E+05 | 4.89E−05 | 6.03E−11 | 236 |
| H4H1789Pa | 1.99E+05 | 1.79E−03 | 8.97E−09 | 6 | 2.21E+05 | 3.57E−04 | 1.61E−10 | 324 |
| H2M1798N | 1.41E+06 | 8.35E−03 | 5.94E−09 | 1 | 2.91E+06 | 2.17E−04 | 7.47E−11 | 53 |
| H2M1811N | 1.30E+05 | 2.95E−03 | 2.27E−08 | 4 | 2.65E+05 | 2.56E−04 | 9.66E−10 | 45 |

TABLE 5

(25° C.)

| Antibody | monomeric monkey CD48 | | | | dimeric monkey CD48 | | | |
|---|---|---|---|---|---|---|---|---|
| | ka | kd | $K_D$ | T½ | ka | kd | $K_D$ | T½ |
| H4H1707N | 2.89E+05 | 3.62E−04 | 1.25E−09 | 32 | 8.05E+05 | 1.19E−03 | 1.48E−09 | 10 |
| H4H1713N | 3.15E+05 | 2.65E−04 | 8.43E−10 | 44 | 8.61E+05 | 2.42E−04 | 2.81E−10 | 48 |
| H4H1763N | 5.27E+05 | 1.24E−03 | 2.34E−09 | 9 | 1.33E+06 | 6.88E−05 | 5.19E−11 | 168 |
| H4H1764N | 8.77E+04 | 2.06E−04 | 2.34E−09 | 56 | 2.51E+05 | 1.32E−04 | 5.25E−10 | 88 |
| H4H1769P | 5.88E+05 | 3.93E−04 | 6.69E−10 | 29 | 4.82E+05 | 2.56E−05 | 5.31E−11 | 451 |
| H4H1770P | 7.20E+05 | 2.15E−04 | 2.98E−10 | 54 | 8.58E+05 | 1.13E−04 | 1.31E−10 | 103 |
| H4H1771P | 1.05E+06 | 4.77E−04 | 4.53E−10 | 24 | 9.39E+05 | 5.51E−05 | 5.87E−11 | 210 |
| H4H1772P | 4.61E+05 | 5.08E−04 | 1.10E−09 | 23 | 5.19E+05 | 5.02E−05 | 9.68E−11 | 230 |
| H4H1774P | 2.63E+05 | 7.63E−05 | 2.89E−10 | 151 | 3.95E+05 | 2.07E−05 | 5.25E−11 | 558 |
| H4H1775P | 2.91E+05 | 4.07E−05 | 1.40E−10 | 284 | 4.88E+05 | 6.60E−06 | 1.35E−11 | 1750 |
| H4H1778P | 2.76E+05 | 8.98E−05 | 3.25E−10 | 129 | 3.84E+05 | 1.77E−05 | 4.60E−11 | 654 |
| H4H1779P | 3.01E+05 | 1.13E−04 | 3.75E−10 | 102 | 5.22E+05 | 3.17E−05 | 6.06E−11 | 364 |
| H4H1781P | 2.98E+05 | 7.80E−05 | 2.62E−10 | 148 | 5.99E+05 | 2.13E−05 | 3.56E−11 | 542 |
| H4H1789Pa | 4.16E+05 | 1.38E−03 | 3.31E−09 | 8 | 6.51E+05 | 2.76E−04 | 4.23E−10 | 42 |

TABLE 6

(37° C.)

| Antibody | monomeric monkey CD48 | | | | dimeric monkey CD48 | | | |
|---|---|---|---|---|---|---|---|---|
| | ka | kd | $K_D$ | T½ | ka | kd | $K_D$ | T½ |
| H4H1707N | 3.27E+05 | 1.22E−03 | 3.72E−09 | 9 | 1.64E+06 | 5.24E−03 | 3.20E−09 | 2 |
| H4H1713N | 3.20E+05 | 3.82E−04 | 1.19E−09 | 30 | 1.72E+06 | 5.16E−04 | 3.00E−10 | 22 |
| H4H1763N | 5.34E+05 | 1.33E−03 | 2.49E−09 | 9 | 2.42E+06 | 1.14E−04 | 4.70E−11 | 101 |
| H4H1764N | 2.13E+05 | 6.20E−04 | 2.91E−09 | 19 | 1.92E+05 | 1.42E−03 | 7.40E−09 | 8 |
| H4H1769P | 2.80E+05 | 1.10E−03 | 3.92E−09 | 11 | 6.97E+05 | 9.80E−05 | 1.41E−10 | 118 |
| H4H1770P | 3.96E+05 | 1.74E−04 | 4.40E−10 | 66 | 1.53E+06 | 1.39E−04 | 9.11E−11 | 83 |
| H4H1771P | 6.57E+05 | 8.77E−04 | 1.34E−09 | 13 | 1.64E+06 | 1.02E−04 | 6.21E−11 | 113 |
| H4H1772P | 3.20E+05 | 1.45E−03 | 4.53E−09 | 8 | 7.72E+05 | 7.31E−05 | 9.47E−11 | 158 |

TABLE 6-continued (37° C.)

| | monomeric monkey CD48 | | | | dimeric monkey CD48 | | | |
|---|---|---|---|---|---|---|---|---|
| Antibody | ka | kd | $K_D$ | T½ | ka | kd | $K_D$ | T½ |
| H4H1774P | 1.97E+05 | 2.67E−04 | 1.36E−09 | 43 | 5.08E+05 | 5.40E−05 | 1.07E−10 | 214 |
| H4H1775P | 2.60E+05 | 1.29E−04 | 4.98E−10 | 90 | 6.69E+05 | 3.97E−05 | 5.93E−11 | 291 |
| H4H1778P | 1.89E+05 | 2.53E−04 | 1.34E−09 | 46 | 5.25E+05 | 3.60E−05 | 6.86E−11 | 321 |
| H4H1779P | 2.77E+05 | 2.89E−04 | 1.04E−09 | 40 | 7.21E+05 | 5.98E−05 | 8.29E−11 | 193 |
| H4H1781P | 3.50E+05 | 3.07E−04 | 8.75E−10 | 38 | 8.75E+05 | 6.61E−05 | 7.55E−11 | 175 |
| H4H1789Pa | 4.37E+05 | 2.06E−03 | 4.71E−09 | 6 | 9.90E+05 | 7.68E−04 | 7.76E−10 | 15 |

As shown in Tables 3-6, the exemplary antibodies tested in this Example exhibited high affinity binding to both human and monkey CD48 soluble protein. A significant increase in binding affinity was observed when bivalent CD48 was used as the solution-phase analyte in comparison to monovalent CD48.

Example 4

Epitope Mapping of H4H1789 Pa Binding to CD48 by H/D Exchange

Experiments were conducted to determine the amino acid residues of CD48 with which H4H1789 Pa interacts. For this purpose H/D exchange epitope mapping was carried out. A general description of the H/D exchange method is set forth in e.g., Ehring (1999) *Analytical Biochemistry* 267(2):252-259; and Engen and Smith (2001) *Anal. Chem.* 73:256A-265A.

To map the epitope of CD48 for binding H4H1789 Pa via H/D exchange, a recombinant human CD48-myc-myc-his fusion construct was used ("hCD48-mmH"; SEQ ID NO:391). hCD48-mmH was first deglycosylated with PNGase F (New. England BioLabs) under native conditions. H4H1789 Pa was then covalently attached to anti-human IgG-agarose beads (Sigma) by crosslinker BS³ (Thermo Scientific).

In the 'on-solution/off-beads' (on-exchange in solution followed by off-exchange on beads) experiment, the ligand (deglycosylated hCD48-mmH) was deuterated for 5 min or 10 min in PBS buffer prepared with $D_2O$, and then bound to H4H1789Pa beads during a 2 min incubation. The CD48-bound beads were washed with PBS aqueous buffer (prepared with $H_2O$) and incubated for half of the on-exchange time. After the off-exchange, the bound CD48 was eluted from beads with an ice-cold low pH TFA solution. The eluted CD48 was then digested with immobilized pepsin (Thermo Scientific) for 5 min. The resulting peptides were isolated using ZIPTIP® chromatographic pipette tips and immediately analyzed by UTRAFLEXTREME™ matrix assisted laser desorption ionization time of flight (MALDI-TOF)-TOF mass spectrometry (MS).

In the 'on-beads/off-beads' (on-exchange on beads followed by off-exchange on beads) experiment, CD48 was first bound to H4H1789 Pa beads and then incubated for 5 min or 10 min in $D_2O$ for on-exchange. The following steps (off-exchange, pepsin digestion, and MS analysis) were carried out as described for the 'on-solution/off-beads' procedure. The centroid values of all the detected peptides were calculated and compared between these two sets of experiments.

The results are summarized in Table 7a which provides a quantitative comparison of the centroid mass-to-charge ratios for all the detected peptides identified by liquid chromatography-matrix assisted laser desorption ionization (LC-MALDI) MS following the H/D exchange and peptic digest procedure. While the majority of the observed peptic peptides gave similar centroid mass-to-charge ratios for both the on-solution/off-beads and on-beads/off-beads experiments, three different peptic peptides corresponding to residues 60-76 of SEQ ID NO:384 and seven peptides corresponding to residues 107-125 of SEQ ID NO:384 gave consistently higher centroid values, (i.e., higher deuterium retention) in the 'on-solution/off-beads' experiment. For purposes of the present Example, a positive difference (Δ) of at least 0.20 indicates amino acids protected by antibody binding. Such residues are indicated by bold text and an asterisk (*) in Table 7a.

TABLE 7a

| | H4H1789Pa Binding to hCD48-mmH | | | | | |
|---|---|---|---|---|---|---|
| Residues | 5 min on-/2.5 min off-exchange | | | 10 min on-/5 min off-exchange | | |
| (of SEQ ID NO: 384) | On-solution/ Off Beads | On-Beads/ Off-Beads | Δ | On-solution/ Off Beads | On-Beads/ Off-Beads | Δ |
| 27-33 | 804.97 | 804.95 | 0.03 | 804.93 | 804.98 | −0.05 |
| 32-50 | 2001.88 | 2001.78 | 0.11 | 2001.68 | 2001.77 | −0.09 |
| 45-59 | 1856.18 | 1856.19 | −0.01 | 1856.37 | 1856.32 | 0.04 |
| 53-59 | 986.77 | 986.75 | 0.02 | 986.26 | 986.15 | 0.12 |
| 60-68* | 1143.72 | 1143.33 | 0.39 | 1143.78 | 1143.41 | 0.37 |
| 60-76* | 2195.08 | 2194.74 | 0.34 | 2195.13 | 2194.82 | 0.31 |
| 63-76* | 1783.45 | 1783.24 | 0.21 | 1783.51 | 1783.26 | 0.25 |
| 69-76 | 1070.35 | 1070.29 | 0.06 | 1070.30 | 1070.29 | 0.01 |
| 77-94 | 2036.78 | 2036.65 | 0.13 | 2036.73 | 2036.87 | −0.13 |
| 95-106 | 1413.74 | 1413.70 | 0.03 | 1413.64 | 1413.65 | −0.01 |
| 95-107 | 1576.79 | 1576.86 | −0.07 | 1576.83 | 1576.84 | −0.02 |
| 107-120* | 1711.01 | 1710.73 | 0.28 | 1710.97 | 1710.73 | 0.24 |
| 107-125* | 2379.65 | 2379.19 | 0.47 | 2379.64 | 2379.33 | 0.31 |
| 108-120* | 1547.48 | 1547.04 | 0.44 | 1547.38 | 1547.12 | 0.26 |

TABLE 7a-continued

H4H1789Pa Binding to hCD48-mmH

| Residues (of SEQ ID NO: 384) | 5 min on-/2.5 min off-exchange | | | 10 min on-/5 min off-exchange | | |
|---|---|---|---|---|---|---|
| | On-solution/ Off Beads | On-Beads/ Off-Beads | Δ | On-solution/ Off Beads | On-Beads/ Off-Beads | Δ |
| 108-125* | 2216.50 | 2216.02 | 0.48 | 2216.54 | 2216.15 | 0.39 |
| 110-120* | 1303.49 | 1303.23 | 0.26 | 1303.46 | 1303.24 | 0.22 |
| 110-121* | 1489.25 | 1488.79 | 0.46 | 1489.22 | 1488.89 | 0.34 |
| 110-125* | 1972.12 | 1971.70 | 0.42 | 1972.10 | 1971.77 | 0.33 |
| 161-175 | 1902.09 | 1902.05 | 0.04 | 1902.07 | 1902.05 | 0.02 |
| 161-178 | 2257.67 | 2257.70 | −0.02 | 2257.70 | 2257.92 | −0.22 |
| 161-181 | 2557.23 | 2557.13 | 0.10 | 2557.09 | 2557.35 | −0.27 |
| 163-175 | 1688.45 | 1688.40 | 0.05 | 1688.31 | 1688.29 | 0.01 |
| 163-181 | 2343.05 | 2343.03 | 0.02 | 2342.94 | 2343.22 | −0.28 |
| 166-181 | 1893.07 | 1892.97 | 0.10 | 1892.89 | 1893.21 | −0.33 |
| 168-181 | 1672.12 | 1672.13 | −0.02 | 1672.14 | 1672.21 | −0.07 |
| 225-236 | 1318.53 | 1318.53 | −0.01 | 1318.51 | 1318.63 | −0.12 |
| 225-248 | 2828.26 | 2828.14 | 0.12 | 2828.09 | 2828.30 | −0.21 |
| 228-248 | 2498.76 | 2498.69 | 0.07 | 2498.71 | 2498.83 | −0.12 |
| 237-248 | 1528.63 | 1528.56 | 0.07 | 1528.49 | 1528.58 | −0.08 |

The H/D exchange results summarized in Table 7a demonstrate that the two regions (corresponding to amino acids 60-76 and 107-125 of SEQ ID NO:384) are protected from proton off-exchange by H4H1789 Pa binding to these specific epitopes on CD48 after on-exchange. Since the peptides corresponding to residues 69-76 did not show significant mass difference, the N-terminal epitope region can be reduced to residues 60-68 of SEQ ID NO:384. Therefore, the two segments (corresponding to amino acids 60-76 and 107-125 of SEQ ID NO:384) on CD48 are defined by the H/D exchange method as a discontinuous epitope for antibody H4H1789 Pa binding to the soluble human CD48 protein. These areas of antibody interaction are located within Ig Domain 1 of CD48 and are depicted diagrammatically in FIG. 1.

To confirm the validity and accuracy of the aforementioned epitope mapping assay, additional experiments were conducted using a control antibody having a previously defined epitope. In particular, H/D exchange experiments were performed using the CD48-mmH construct described above (SEQ ID NO:391) and the anti-Myc antibody 9E10. The Myc epitope corresponds to amino acids 195-216 of SEQ ID NO:391.

All the experimental procedures for these confirmatory experiments were the same as for the H4H1789 Pa experiments described above except that the anti-Myc antibody 9E10 was used as the test antibody. The results of the confirmatory anti-Myc experiments are summarized in Table 7b. (Note that the residue numbering shown in the first column of Table 7b corresponds to the actual amino acid numbering of the hCD48-mmH construct [SEQ ID NO:391], whereas the residue numbering shown in the first column of Table 7a has been adjusted to correspond to the amino acid number of the full length human CD48 polypeptide [SEQ ID NO:384]). As before, a positive difference (Δ) of at least 0.20 indicates amino acids protected by antibody binding. Such residues are indicated by bold text and an asterisk (*) in Table 7b.

TABLE 7b

9E10 Binding to hCD48-mmH

| Residues (of SEQ ID NO: 391) | 5 min on-/2.5 min off-exchange | | | 10 min on-/5 min off-exchange | | |
|---|---|---|---|---|---|---|
| | On-solution/ Off Beads | On-Beads/ Off-Beads | Δ | On-solution/ Off Beads | On-Beads/ Off-Beads | Δ |
| 1-7 | 804.93 | 804.91 | 0.02 | 804.99 | 804.95 | 0.04 |
| 19-33 | 1856.16 | 1856.24 | −0.09 | *** | *** | |
| 34-50 | 2194.74 | 2194.68 | 0.06 | 2194.75 | 2194.64 | 0.10 |
| 37-50 | 1783.23 | 1783.21 | 0.02 | 1783.27 | 1783.19 | 0.08 |
| 43-50 | 1070.04 | 1070.07 | −0.03 | 1070.09 | 1070.08 | 0.01 |
| 51-68 | 2036.51 | 2036.52 | 0.00 | 2036.53 | 2036.50 | 0.02 |
| 69-80 | 1413.96 | 1413.89 | 0.07 | 1413.78 | 1413.80 | −0.02 |
| 69-81 | 1576.94 | 1577.07 | −0.13 | 1577.05 | 1577.09 | −0.04 |
| 81-94 | 1710.59 | 1710.62 | −0.02 | 1710.59 | 1710.57 | 0.03 |
| 81-99 | 2379.16 | 2379.23 | −0.07 | 2379.26 | 2379.24 | 0.02 |
| 82-94 | 1546.91 | 1546.84 | 0.07 | 1546.90 | 1546.84 | 0.06 |
| 82-99 | 2215.89 | 2215.89 | 0.00 | 2215.88 | 2215.87 | 0.00 |
| 84-94 | 1303.32 | 1303.34 | −0.02 | 1303.29 | 1303.20 | 0.09 |
| 84-99 | 1972.13 | 1972.14 | −0.02 | 1972.21 | 1972.11 | 0.10 |
| 135-155 | 2556.75 | 2556.64 | 0.12 | 2556.71 | 2556.66 | 0.05 |
| 137-145 | 1186.27 | 1186.33 | −0.06 | 1186.27 | 1186.29 | −0.02 |
| 137-155 | 2342.71 | 2342.93 | −0.22 | 2342.99 | 2342.94 | 0.05 |
| 140-155 | 1891.85 | 1891.90 | −0.05 | 1891.90 | 1891.92 | −0.02 |
| 199-210 | 1318.80 | 1318.57 | 0.22 | 1318.59 | 1318.61 | −0.02 |
| 199-222* | 2830.27 | 2828.66 | 1.61 | 2829.99 | 2828.63 | 1.36 |

TABLE 7b-continued

| | 9E10 Binding to hCD48-mmH | | | | | |
|---|---|---|---|---|---|---|
| | 5 min on-/2.5 min off-exchange | | | 10 min on-/5 min off-exchange | | |
| Residues (of SEQ ID NO: 391) | On-solution/ Off Beads | On-Beads/ Off-Beads | Δ | On-solution/ Off Beads | On-Beads/ Off-Beads | Δ |
| 202-222* | 2500.60 | 2499.30 | 1.30 | 2500.31 | 2499.28 | 1.03 |
| 211-220* | 1255.00 | 1254.38 | 0.62 | 1254.86 | 1254.38 | 0.48 |
| 211-222* | 1529.30 | 1528.69 | 0.60 | 1529.21 | 1528.76 | 0.45 |

As expected, the epitope recognized by 9E10 is identified as being in the region defined by amino acids 199-222 of SEQ ID NO:391. The results summarized in Table 7b thus confirm that the H/D methodology used in this Example can be used to reliably and accurately identify the amino acid residues on a polypeptide antigen with which an antibody interacts.

Example 5

Antibody Blocking of CD48-2B4 Interaction Measured by ELISA

The ability of human anti-CD48 monoclonal antibodies to block human CD48 and monkey CD48 binding to the human cognate ligand, human 2B4, was measured using a competition sandwich ELISA (Table 8). Constant amounts of biotinylated dimeric human CD48 protein expressed as a fusion with mouse IgG2a Fc ("bio-hCD48-mFc" [SEQ ID NO:387]) or monomeric monkey CD48 expressed with a tag consisting of 2 myc and one 6-His epitopes ("mfCD48-mmH" [SEQ ID NO:386]) were separately titrated with varying amounts of antibodies. These antibody-protein complexes were incubated (1 hr, 25° C.) before being transferred to microtiter plates coated with a dimeric construct expressing the human 2B4 receptor fused to a either human IgG1 (h2B4-hFc [R&D Systems, Inc., Minneapolis, Minn., Cat. No. 1039-2B]) or mouse IgG2a Fc (h2B4-mFc [SEQ ID NO:389]). After a 1 hr at 25° C. the wells were washed and bound human CD48 was detected with streptavidin conjugated with horse-radish peroxidase (HRP), and monkey CD48 was detected with an HRP conjugated anti-myc polyclonal antibody. The ELISA was developed with a TMB solution to produce a colorimetric reaction and quenched with sulfuric acid before reading absorbance at 450 nm on a Victor X5 plate reader. Sigmoidal dose response curves were fit to the data using Prism™ software. The calculated $IC_{50}$ value, defined as the concentration of antibody required to block 50% of hCD48 or mfCD48 binding to 2B4, was used as an indicator of blocking potency. (Tables 8 and 9, NB=no binding observed)

TABLE 8

| Antibody | h2B4-hFc + bio-hCD48-mFc $IC_{50}$ (molar) | h2B4-hFc + mfCD48-mmH $IC_{50}$ (molar) |
|---|---|---|
| H2M1707N | 2.2E-11 | 2.3E-11 |
| H2M1709N | 4.5E-11 | 1.2E-10 |
| H2M1710N | 5.8E-11 | 3.7E-10 |
| H2M1711N | 5.9E-12 | 2.9E-11 |
| H2M1712N | 1.4E-11 | 1.7E-11 |
| H2M1713N | 2.6E-11 | 2.4E-11 |
| H2M1763N | 8.8E-12 | 1.3E-11 |
| H2M1764N | 6.4E-11 | 2.4E-10 |
| H3M1766N | NB | NB |
| H2M1798N | 5.0E-12 | NB |
| H2M1811N | 4.9E-10 | 2.2E-10 |

TABLE 9

| Antibody | h2B4-mFc + bio-hCD48-mFc $IC_{50}$ (molar) | h2B4-mFc + mfCD48-mmH $IC_{50}$ (molar) |
|---|---|---|
| H2M1707N | 8.6E-12 | 4.9E-12 |
| H4H1707N | 2.2E-11 | 4.5E-11 |
| H2M1710N | 4.9E-10 | 2.6E-10 |
| H2M1711N | 4.1E-12 | 7.7E-13 |
| H2M1713N | 2.2E-11 | 2.5E-12 |
| H4H1713N | 1.8E-11 | 3.4E-12 |
| H2M1763N | 5.5E-12 | 2.3E-12 |
| H4H1763N | 7.4E-12 | 7.2E-12 |
| H2M1764N | 2.9E-11 | 6.2E-11 |
| H4H1764N | 7.6E-11 | 1.6E-10 |
| H4H1769P | 1.5E-11 | 1.8E-11 |
| H4H1770P | 2.0E-11 | 2.2E-11 |
| H4H1771P | 9.9E-12 | 2.2E-12 |
| H4H1772P | 1.4E-11 | 4.4E-12 |
| H4H1774P | 2.5E-11 | 1.6E-11 |
| H4H1775P | 4.4E-11 | 4.3E-11 |
| H4H1778P | 5.6E-11 | 8.4E-12 |
| H4H1779P | 1.6E-11 | 5.7E-12 |
| H4H1781P | 1.8E-11 | 8.1E-12 |
| H4H1789Pa | 5.3E-11 | 3.8E-11 |

As shown in Tables 8 and 9, all tested antibodies effectively blocked the interaction between CD48 and 2B4.

Example 6

Antibody Blocking of IFN-gamma Release in Primary Human PBMCs

The ability of human anti-CD48 monoclonal antibodies of the present invention to block activation of primary human peripheral blood mononuclear cells (PBMC) was measured using an IFNγ release assay. Human PBMC were isolated from white blood cell concentrate of several donors (Leukopak, New York Blood Center, New York, N.Y.) by centrifugation on Ficoll-Hypaque gradient. Cells were re-suspended in RPMI-1640 medium supplemented with 10% fetal bovine serum at final concentration of 1 million/ml and plated in 96-well microtiter plates (2000 per well). Cells were incubated with varying amounts of CD48-specific antibodies (1 hr, 37° C.) prior to addition of agonist anti-CD3 (B&D Pharmingen, San Jose, Calif., Cat #555336) and anti-CD28 (B&D Pharmingen, San Jose, Calif., Cat #555725) antibodies (both at final concentration of 40 ng/ml) pre-mixed with protein G (at final concentration of 0.8 mg/ml, Sigma-Aldrich, St. Louis, Mo., Cat #P4689). After 48 h at 37° C. and 5% $CO_2$, supernatants were collected and IFNγ concentration was determined using ELISA kit (B&D Biosciences, San Jose, Calif., Cat #555142) per manufacturer's protocol. Sigmoidal dose response curves were fit to the data using Prism™ software. The calculated $IC_{50}$ values, defined as the concentration of antibody required to block 50% of maximal IFNγ release, was used as an indicator of blocking potency.

(Tables 10-12; NB=no binding observed; ND=not determined; NC=data not convergent).

TABLE 10

| | Inhibition of IFN-gamma Release $IC_{50}$ (Molar) | | | | |
|---|---|---|---|---|---|
| Antibody | Donor 1 | Donor 2 | Donor 3 | Donor 4 | Donor 5 |
| H2M1707N | 4.9E−11 | 3.0E−11 | 1.1E−10 | 1.7E−10 | 1.5E−11 |
| H2M1709N | 4.8E−11 | 5.7E−11 | 1.2E−10 | 1.1E−10 | 3.2E−11 |
| H2M1763N | 4.9E−11 | 3.4E−11 | 1.3E−10 | 7.5E−11 | 1.9E−11 |
| H2M1798N | 4.3E−11 | 3.4E−11 | 9.5E−11 | 5.7E−10 | 6.0E−11 |
| H2M1764N | 2.7E−11 | 1.1E−10 | 1.9E−10 | 9.5E−11 | 1.9E−11 |
| H2M1711N | NB | NB | NB | NB | NB |
| H2M1710N | 7.8E−10 | 1.9E−10 | 1.1E−06 | 1.5E−09 | 2.7E−10 |
| H2M1712N | 2.0E−11 | 2.8E−11 | 7.2E−11 | 4.8E−11 | 1.1E−11 |
| H3M1766N | NB | NB | NB | NB | NB |
| H2M1811N | 9.1E−11 | 4.6E−10 | 8.3E−11 | 4.8E−10 | 9.4E−11 |
| H2M1713N | 2.1E−11 | 7.6E−11 | NB | 1.1E−10 | 1.1E−11 |

TABLE 11

| | Inhibition of IFN-gamma Release $IC_{50}$ (Molar) | |
|---|---|---|
| Antibody | Donor 6 | Donor 7 |
| H2M1707N | 9.3E−12 | 1.9E−11 |
| H2M1763N | 2.6E−11 | 1.8E−11 |
| H2M1764N | 1.0E−10 | not tested |
| H2M1710N | 5.0E−11 | 1.4E−10 |
| H2M1713N | 2.2E−11 | 1.0E−10 |
| H4H1769Pa | NB | NC |
| H4H1770P | NB | NB |
| H4H1771P | NB | NB |
| H4H1772P | 2.0E−12 | 2.2E−11 |
| H4H1774P | 2.5E−11 | 9.5E−12 |
| H4H1775P | NC | 5.1E−12 |
| H4H1778P | 9.8E−12 | NC |
| H4H1779P | 1.7E−12 | 1.5E−11 |
| H4H1781P | 3.6E−12 | 1.5E−11 |
| H4H1789Pa | 1.2E−11 | 1.8E−11 |

TABLE 12

| | Inhibition of IFN-gamma Release $IC_{50}$ (Molar) | | | |
|---|---|---|---|---|
| Antibody | Donor 8 | Donor 9 | Donor 10 | Donor 11 |
| H4H1707N | NC | 5.10E−11 | NC | NC |
| H4H1763N | 8.60E−12 | 9.30E−12 | 1.00E−12 | 3.40E−12 |
| H4H1764N | 5.30E−12 | 3.10E−12 | 5.10E−12 | 2.30E−11 |
| H4H1769Pa | NB | 5.70E−12 | NB | 1.90E−11 |
| H4H1771P | NC | NB | NB | 1.50E−11 |
| H4H1772P | NB | NC | 1.40E−12 | 8.60E−11 |
| H4H1775P | 3.10E−12 | 2.30E−12 | 2.00E−11 | NC |
| H4H1789Pa | 3.70E−11 | 1.60E−11 | 1.30E−11 | 1.30E−11 |

As shown in Tables 10, 11, and 12, majority of the tested antibodies effectively blocked the IFNγ release in primary human PBMC.

Example 7

Antibody Blocking of IFN-gamma Release in Primary Human Mixed Lymphocyte Reaction (MLR) Assays The ability of human anti-CD48 monoclonal antibodies to block activation of primary human peripheral blood mononuclear cells (PBMC) was measured using a mixed lymphocyte reaction assay (Tables 13 and 14). Human PBMC were isolated from white blood cell concentrate (Leukopak, New York Blood Center, New York, N.Y.) or whole blood samples (obtained through an in-house blood collection program) by centrifugation on Ficoll-Hypaque gradient. Cells were resuspended in RPMI-1640 medium supplemented with 10% fetal bovine serum to a final concentration of 1 million/ml. Freshly isolated cells were mixed with previously irradiated cells from a different donor at 10:1 ratio and plated in 96-well microtiter plates (200 μl per well). Immediately after plating cells, antibodies were added to final concentrations ranging from 0.01 nM to 10 nM. Cells were incubated for 7 days at 37° C. and 5% $CO_2$. Supernatants were collected and IFNγ concentration was determined using ELISA kit (B&D Biosciences, San Jose, Calif., Cat #555142) per the manufacturer's protocol. Sigmoidal dose response curves were fit to the data using Prism™ software. The IFNγ blockade level was defined as the difference between the maximum and minimum values of the curves fitted through the dose-response data, normalized by the maximum value ("% blockade" in Tables 13 and 14; "nb"=no binding observed; NC=data not convergent). The calculated $IC_{50}$ value, defined as the concentration of antibody required to block 50% of maximal IFNγ release, was used as an indicator of blocking potency (Table 14).

TABLE 13

| | % Blockade for nine individual donors (D1-D9) | | | | | | | | |
|---|---|---|---|---|---|---|---|---|---|
| Antibody | D1 | D2 | D3 | D4 | D5 | D6 | D7 | D8 | D9 |
| H4H1769Pa | nb | 60 | 39 | nb | 43 | 60 | 51 | 40 | nb |
| H4H1771P | 78 | 79 | 88 | nb | 47 | 50 | 36 | nb | 32 |
| H4H1772P | nb | 65 | 62 | 39 | 62 | 63 | 58 | 25 | 59 |
| H4H1775P | 42 | 77 | 87 | 37 | 70 | 72 | 69 | 22 | 60 |
| H4H1789Pa | 65 | 66 | 88 | 36 | 89 | 82 | 75 | 65 | 66 |
| H4H1707N | 66 | 87 | 78 | 20 | 62 | 77 | 62 | 42 | 60 |
| H4H1763N | 59 | 89 | 68 | 52 | 63 | 75 | 48 | 30 | 53 |
| H4H1764N | 69 | 46 | 80 | nb | 75 | 59 | 48 | nb | nb |
| Orencia ® | nb | 52 | nb | nb | 68 | 80 | 53 | 58 | 75 |
| Amevive ® | 54 | 53 | 76 | 66 | 78 | 40 | 79 | nb | nb |
| belatacept | 81 | 77 | 74 | 90 | 82 | 83 | 80 | 64 | 66 |

TABLE 14

| | H4H1763N | | H4H1789Pa | |
|---|---|---|---|---|
| Donor | % Blockade | $IC_{50}$ (M) | % Blockade | $IC_{50}$ (M) |
| D1 | 59 | ~1.0 × $10^{-11}$ | 65 | ~1.4 × $10^{-12}$ |
| D2 | 89 | NC | 66 | ~9.3 × $10^{-12}$ |
| D3 | 68 | ~6.4 × $10^{-12}$ | 88 | NC |
| D4 | 52 | 2.1 × $10^{-10}$ | 36 | 2.3 × $10^{-10}$ |
| D5 | 63 | ~2.7 × $10^{-11}$ | 89 | ~9.0 × $10^{-11}$ |
| D6 | 75 | 2.3 × $10^{-11}$ | 82 | 2.8 × $10^{-12}$ |
| D7 | 48 | NC | 75 | NC |
| D8 | 30 | ~3.7 × $10^{-9}$ | 65 | 2.9 × $10^{-11}$ |
| D9 | 53 | ~4.1 × $10^{-9}$ | 66 | 1.8 × $10^{-10}$ |
| D10 | 79 | ~8.4 × $10^{-11}$ | 77 | ~5.0 × $10^{-11}$ |
| D11 | 72 | 7.3 × $10^{-11}$ | 80 | ~9.2 × $10^{-11}$ |
| D12 | 79 | ~5.6 × $10^{-11}$ | 55 | ~3.0 × $10^{-10}$ |
| D13 | 72 | 9.2 × $10^{-11}$ | 64 | ~9.6 × $10^{-11}$ |
| D14 | 90 | 6.3 × $10^{-11}$ | 83 | 2.0 × $10^{-10}$ |
| D15 | 82 | ~5.9 × $10^{-14}$ | 95 | ~2.7 × $10^{-12}$ |
| D16 | 90 | 7.6 × $10^{-12}$ | 85 | ~1.2 × $10^{-11}$ |

As shown in Tables 13 and 14, all tested antibodies effectively blocked the IFNγ release in primary human mixed lymphocyte reaction (PBMC MLR). The ability of the candidate anti-CD48 antibodies to effectively block IFNγ release in primary human PBMCs, as demonstrated in Examples 6 and 7, suggests that these antibodies are useful in blocking inappropriate autoimmune reactions in diseases and conditions such as systemic lupus erythematosus, rheumatoid arthritis, graft-versus-host disease, inflammatory bowel disease, allergy, celiac disease, psoriasis, asthma, etc.

Example 8

Antibody Blocking of Human Cytokine Release in Rag2$^{-/-}$γ$_c$$^{-/-}$ Mice Reconstituted with Human Hematopoietic Stem Cells

The ability of human anti-CD48 monoclonal antibodies to block activation of human immune cells in vivo was measured using a chimeric animal model consisting of immunodeficient Rag2$^{-/-}$γ$_c$$^{-/-}$ mice reconstituted with human hematopoietic stem cells. Animals were reconstituted with human stem cells shortly after birth and reconstitution was confirmed by flow cytometry. Fully reconstituted animals (12-16 weeks old) were intraperitoneally injected with 5 mg/kg of CD48-specific antibodies or appropriate isotype control (in-house produced human IgG4(S108P) antibody) 24 h prior to treatment with an agonist mouse anti-human CD3 antibody (OKT3, 1 µg/animal, IP injection, BioLegend, San Diego, Calif., Cat#317315) or the isotype control (in-house produced mouse IgG2a antibody). Blood samples were obtained 24 h after stimulation and serum levels of nine human cytokines were measured using MSD multiplex kit (Human Proinflammatory 9-Plex Ultra-Sensitive Kit, MesoScale Discovery, Gaithersburg, Md., Cat #K15007C-2) per manufacturer's protocol. Both antibodies tested inhibited production of human cytokines (Tables 15 and 16).

TABLE 15

| Treatment Group | Serum cytokine level (pg/ml) | | | | |
|---|---|---|---|---|---|
| | IFNγ | IL-6 | IL-10 | TNFα | IL-2 |
| IgG2a + hIgG4mut | 206.5 ± 30.1 | 145.9 ± 18.5 | 394.0 ± 37.8 | 261.0 ± 25.6 | 173.2 ± 21.4 |
| IgG2a + H4H1763N | 166.3 ± 9.8 | 153.9 ± 13.7 | 343.8 ± 15.0 | 301.2 ± 16.8 | 194.7 ± 11.5 |
| IgG2a + H4H1789Pa | 185.6 ± 14.5 | 169.1 ± 13.1 | 380.1 ± 11.5 | 326.3 ± 27.3 | 184.9 ± 15.5 |
| OKT3 | 8383.1 ± 425.8 | 1144.1 ± 120.6 | 21128.3 ± 1276.0 | 1457.4 ± 69.4 | 2900.6 ± 209.7 |
| OKT3 + hIgG4mut | 5967.7 ± 1659.4 | 1124.4 ± 190.1 | 3853.8 ± 742.3 | 2668.4 ± 555.6 | 521.6 ± 85.9 |
| OKT3 + H4H1763N | 493.9 ± 55.4 | 180.2 ± 12.4 | 536.2 ± 34.0 | 497.1 ± 56.6 | 295.1 ± 35.3 |
| OKT3 + H4H1789Pa | 617.0 ± 116.9 | 249.0 ± 38.8 | 460.9 ± 30.2 | 339.4 ± 20.7 | 244.4 ± 15.3 |

TABLE 16

| Treatment Group | Serum cytokine level (pg/ml) | | | |
|---|---|---|---|---|
| | IL-8 | IL-12 p70 | IL-1β | GM-CSF |
| IgG2a + hIgG4mut | 2186.8 ± 885.4 | 202.7 ± 7.3 | 490.7 ± 37.7 | 177.7 ± 14.8 |
| IgG2a + H4H1763N | 5808.0 ± 926.0 | 217.9 ± 10.4 | 437.4 ± 26.7 | 175.6 ± 10.3 |
| IgG2a + H4H1789Pa | 2740 ± 651 | 213.4 ± 11.4 | 408.8 ± 15.9 | 172.3 ± 7.7 |
| OKT3 | 5241.8 ± 1237.0 | 225.6 ± 13.0 | 445.0 ± 8.8 | 1107.7 ± 90.9 |
| OKT3 + hIgG4mut | 19899.0 ± 3138.1 | 279.0 ± 18.2 | 603.9 ± 41.4 | 676.3 ± 59.2 |
| OKT3 + H4H1763N | 3381.0 ± 1169.0 | 182.1 ± 10.5 | 410.4 ± 22.4 | 243.3 ± 10.4 |
| OKT3 + H4H1789Pa | 1585.7 ± 269.2 | 206.3 ± 4.2 | 395.0 ± 16.4 | 559.3 ± 76.8 |

As shown in Tables 15 and 16, both tested antibodies effectively blocked cytokine release induced by polyclonal stimulation of human immune cells in a chimeric in vivo system (Rag2$^{-/-}$γ$_c$$^{-/-}$ mice reconstituted with human hematopoietic stem cells).

Example 9

Antibody Inhibition of Weight Loss and Prolonged Survival in a Xenogenic Model of Graft-versus-Host Disease (GvHD)

The ability of a human anti-CD48 monoclonal antibody, H4H1789 Pa, to block activation of human immune cells in vivo was determined using a xenogeneic animal model of Graft-versus-Host Disease (GvHD) established in the immunodeficient NOD/scid/$^{-/-}$γ$_c$$^{-/-}$ (NSG) mice engrafted with human peripheral blood mononuclear cells (PBMC). Eight week-old mice were injected intravenously with freshly isolated PBMC from healthy normal volunteers (Day0). The engraftment success rate was evaluated as percentage of cells positive for human CD45 cell surface marker (detected by flow cytometry) in the peripheral blood three days after the PBMC injection. A single intraperitoneal dose of H4H1789 Pa (10 mg/kg) administered 24 h prior to induction with human PBMC fully inhibited engraftment of human cells (<10% of the cells in lymphocyte gate compared to ~99% in the blood from mice treated with isotype control).

Figure 2:
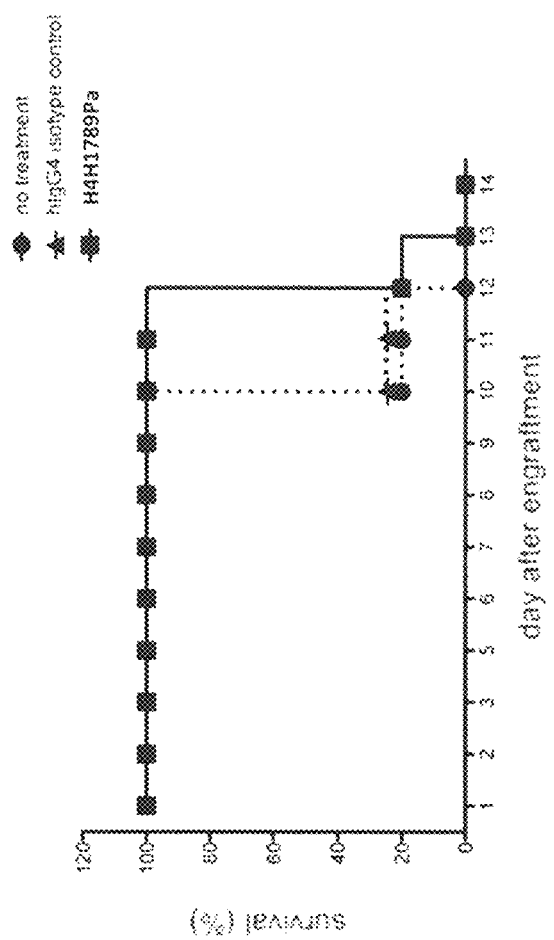
FIG. 2. Graphical representations of the effects of anti-CD48 antibody treatment in a mouse model of graft-versus-host disease. (see Example 9). Panel A shows the weight loss observed in treated and control animals; Panel B shows the percent survival of treated and control animals. For both Panels (●) indicates no treatment; (▲) indicates hIgG4 isotype control treatment; and (■) indicates treatment with the exemplary anti-CD48 antibody H4H1789 Pa.
Figure 2:
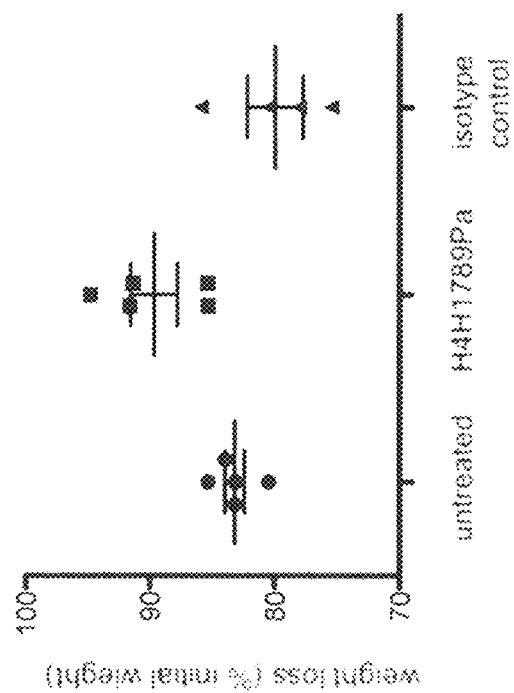

In 100% of untreated animals, successful engraftment of human cells was observed leading to development of GvHD symptoms (weight loss, hunched position, ruffled fur, weakness, etc.) 7-8 days after the PBMC injection. Mice treated with a single intraperitoneal dose of H4H1789 Pa (10 mg/kg) on Day3, showed delayed weight loss (statistically significant on Day10) and a trend towards prolonged survival (FIG. 2). Further, human cytokine levels were measured in the sera obtained from terminal bleeds (Day 13 or earlier) using MSD multiplex kit (Human Proinflammatory 9-Plex Ultra-Sensitive Kit, MesoScale Discovery, Gaithersburg, Md., Cat. No. K15007C-2) per manufacturer's protocol. Treatment with H4H1789 Pa resulted in reduced levels of human IL-8 (55.2±21.3 pg/ml compared to 142.7±22.2 pg/ml in the isotype control group), IL-10 (85.4±2.6 pg/ml vs 171.8±44.2 pg/ml), IL-6 (20.5±12.3 pg/ml vs 30.0±8.9 pg/ml), and TNFα (35.3±4.5 pg/ml vs 51.6±1.1 pg/ml). No reduction in levels of human GM-CSF (554.9±131.8 pg/ml vs 348.9±20.7 pg/ml) and IFNγ (4.8±0.9 ng/ml vs 5.0±0.5 ng/ml) were observed. Levels of human IL-1β, IL-2 and IL-12p70 were below detection.

As shown in FIG. 2, anti-CD48 antibody, H4H1789 Pa, delayed weight loss (p<0.05, Dunnett's multiple comparison test) and prolonged survival in a xenogeneic model of GvHD (NSG mice engrafted with human PBMC). These results confirm the utility of anti-CD48 therapy in the treatment of GvHD.

Example 10

Clinical Trial of an Anti-CD48 Antibody for the Treatment of Celiac Disease

Celiac disease is a chronic HLA-DQ2 or DQ8 restricted CD4+ T cell mediated enteropathy resulting from the secretion of interferon-γ in response to specific dietary deamidated gluten peptides from wheat, barley and rye which have a high binding affinity to these specific HLA class II molecules.

A 6-week, double-blind, placebo-controlled, proof-of-mechanism study is conducted to evaluate the efficacy, safety, and tolerability of treatment with an anti-CD48 antibody in biopsy-proven quiescent celiac disease challenged with oral gluten. Twelve patients receive (3:1 randomization) a single intravenous infusion of 12 mg/kg of an anti-CD48 antibody of the invention (e.g., H4H1789 Pa) or placebo.

Patients included in this study will have been on a gluten free diet for at least 2 years (daily gluten intake≤5 mg), lack gluten intolerance for 8 weeks, have a positive HLA-DQ2 genotype, have negative anti-transglutaminase antibodies (anti-TGA) and negative PBMC interferon-γ ELISpot response to gliadin incubation.

Two weeks after placebo controlled treatment all patients receive a gluten dose of 16 g per day (equivalent to approximately four slices of bread per day) for 3 days consumed as a flour slurry mixed with orange juice or soy milk.

Celiac disease symptoms are recorded by means of a daily symptom diary beginning two weeks prior, during, and up to two weeks after gluten challenge, recording the presence and severity (on a three-point scale) of nausea, bloating, abdominal pain, lethargy, vomiting, diarrhea or other symptoms.

Small bowel biopsies will be taken from the second part of the duodenum for mRNA, histology, immunohistochemistry, determination of villous height/crypt depth (Vh/Cd) and counting of intraepithelial lymphocytes (IEL), two weeks post-randomization and 2 weeks post oral gluten challenge. Overall architecture of the small intestinal mucosa will be evaluated by the modified Marsh classification. Normal mucosa (Marsh 0), low grade inflammation with intraepithelial lymphocytosis (Marsh I), low grade inflammation with intraepithelial lymphocytosis and crypthyperplasia (Marsh II), and gold standard to establish a celiac disease diagnosis with intraepithelial lymphocytosis and crypthyperplasia and villous atrophy (Marsh III).

Prior to oral gluten challenge and one and 2 weeks after challenge, peripheral blood will be sampled from patients (all HLA-DQ2 or DQ8) and purified T lymphocytes will be incubated with the deamidated and control gliadin peptides (α-gliadin$_{57-73}$ native and the Q65E variant). T cell responses in these subjects will be quantitated by measuring the differential IFN-γ ELISpot response to the deamidated versus native α-gliadin$_{57-73}$ peptide and normalized to the IFN-γ ELISpot response to the pan-HLA-DR influenza peptide hemaglutinin peptide HA$_{307-319}$ which is not expected to be altered following gluten challenge.

Safety and tolerability will be assessed by physical examination, clinical laboratory testing, and adverse event reporting.

Primary endpoint, at 2 weeks post-gluten challenge, would be improvement in the median Vh/Cd index. Secondary endpoints would include improvement in overall Marsh intestinal biopsy histologic score, reduction of daily celiac symptom score, and reduction of PBMC interferon-γ ELISpot response to α-gliadin$_{57-73}$ peptide challenge. Exploratory endpoints would include change in tissue and WB mRNA, peripheral T cell phenotypes, tissue median IEL count, and serum cytokines measured by ELISA.

Example 11

Clinical Trial of an Anti-CD48 Antibody for the Treatment of Systemic Lupus Erythematosus (SLE)

SLE is an autoimmune disease characterized by multiple immune system abnormalities including production of autoantibodies against endogenous nucleic acids of apoptosis that can lead to inflammation and tissue damage. Both humoral and cellular immune systems are activated. Autoantibody containing immune complexes and chronic viral infections stimulate Type I interferons which regulate both innate and adaptive immune systems including T cells, B cells, dendritic cells and NK cells creating a self-perpetuating cycle of autoimmunity.

A 12-week, double-blind, placebo-controlled, proof-of-mechanism study is conducted to evaluate the efficacy, safety, and tolerability of treatment with anti-CD48 antibody in stable mild-to-moderate to severe SLE. Twenty patients receive (4:1 randomization) a single intravenous infusion of 12 mg/kg of an anti-CD48 antibody of the invention (e.g., H4H1789 Pa) or placebo. Patients are evaluated on a regular basis with Safety of Estrogens and Lupus Erythematosus National Assessment (SELENA)-Systemic Lupus Erythematosus Disease Activity Index (SLEDAI), SLE Flare Index and the Physician's Global Disease Assessment (PGA). Biologic marker assessments include: (i) CD20+ B cells and CD138+ plasmacytoid cells, CD40L$^+$ T cells, anti-dsDNA, ANA, Immunoglobulins (IgG, IgM, IgE, and IgA) and complement components C1q, C3, C4, and C5a; (ii) levels of cytokines including interferon-α and interferon-γ, IL-10, IL-6, IL-15, IL-21 and BLyS by ELISA; (iii) total numbers of circulating T, B, NK and T-regulatory cells with surface marker analysis by FACS; and/or (iv) measurement of changes in leukocyte numbers in whole blood (e.g. normalization of leukopenia) and involved skin mRNA gene regulation. Laboratory measurements may also include serial PK and anti-drug antibodies.

Key study inclusion/exclusion criteria include: (i) adults age 18 to 70; (ii) stable SLE disease activity for at least two months before screening; and (iii) maintenance with no medication or with a stable treatment regimen of low-dose prednisone, antimalarials, NSAIDs, azathioprine or myclopnolate mofetil.

Patients selected for this study will have measurable anti-dsDNA, anti-Smith, anti-RNP, or anti-Sjogren's antibodies. Patients are excluded with active lupus nephritis requiring hemodialysis, cyclophosphamide or high dose prednisone. Patients are excluded with a history of serious infection within four weeks.

Efficacy is assessed by the reduction in anti-dsDNA antibodies and increase in complement C3 and C4 between baseline and week 4 of anti-CD48 treatment. Exploratory endpoints of improvement include SELENA-SLEDAI, PGA,

Example 12

Clinical Trial of an Anti-CD48 Antibody for the Treatment of Psoriasis

The pathophysiology of psoriasis is related to aberrant immune mediated Th1 and Th17 lymphocyte inflammatory responses which lead to the secretion of cytokines, chemokines and growth factors that can activate and proliferate keratinocytes. These processes lead to the substantial leukocytic infiltration and epidermal thickening which characterize the hallmark pathology of psoriatic plaques.

A 12-week, double-blind, placebo-controlled, proof-of-concept study is conducted to evaluate the efficacy, safety, and tolerability of treatment with an anti-CD48 antibody of the invention (e.g., H4H1789 Pa) in moderate to severe psoriasis. Twenty patients receive (4:1 randomization) a single intravenous infusion of 12 mg/kg of anti-CD48 antibody or placebo. Patients are evaluated on a regular basis with Psoriasis Area and Severity Index (PASI) scores, Physician Global Assessment (PGA) scores, DLQ, photography, clinical observations, and laboratory measurements including PK and anti-drug antibodies.

Efficacy is assessed by the change in PASI between baseline and week 8 of anti-CD48 treatment. The primary endpoint is 75% improvement in PASI score from baseline to week 8. Secondary endpoints include 50% improvement of PASI, PGA, and DLQ between baseline and week 8. Safety and tolerability are assessed by physical examination, clinical laboratory testing, and adverse event reporting.

Key study inclusion/exclusion criteria include: (i) adults age 18 to 70; (ii) chronic plaque psoriasis of at least six month's duration; (iii) BSA involvement of ≥10%; (iv) PASI of ≥12; (v) candidate for systemic or phototherapy; (vi) no current use of systemic therapies or use within the specified washout periods; and/or (vii) no previous discontinuation of a biologic therapy for psoriasis due to lack of efficacy.

Example 13

Clinical Trial of an Anti-CD48 Antibody for the Treatment of Ulcerative Colitis The pathophysiology of ulcerative colitis is characterized by a hyper-reactive CD4+ T cell adaptive immune response in the gut wall directed against the intestinal commensal florae. Activated Th1 and Th17 lymphocytes release pro-inflammatory chemokines and cytokines which cause neutrophils and monocytes to be recruited to the intestine. Costimulation blockade by anti-CD48 has the potential to prevent microbially activated APCs from interacting with naïve T helper cells, which potentiates and sustains the chronic mucosal inflammatory response.

A 12-week, double-blind, placebo-controlled, proof-of-concept study is conducted to evaluate the efficacy, safety, and tolerability of 4 weeks of treatment with an anti-CD48 antibody in patients with moderate-to-severe symptoms of ulcerative colitis. Seventy patients will receive (1:1 randomization) an anti-CD48 antibody of the invention (e.g., H4H1789 Pa) or placebo as a single intravenous infusion at baseline. Patients included in this study are 18-70 years of age, and will have been diagnosed with ulcerative colitis with a Disease Activity Index score (12-point scale) of 6-10, inclusive, at screening. Patients will have been taking an aminosalicylate medication for at least 1 month prior to screening, with a stable dose for at least 2 weeks prior to randomization. If the patient is taking any other medications for ulcerative colitis prior to the study, the doses of such medications will be stable for at least 1 month prior to randomization. With regard to patients taking azathioprine or 6-mercaptopurine, only patients that have been taking these medication(s) for at least 3 months prior to screening are included in the study.

The primary efficacy analysis will evaluate the mean change in Ulcerative Colitis Disease Activity Index Score from baseline to Week 4 as a function of treatment group assignment. A sample size of 35 patients per treatment group (29 per group with evaluable data at week 4) has at least 80% power at the 5% level of significance to detect a difference between the placebo group and active treatment group, assuming a mean difference between treatment groups of at least 3 points, with a common SD of 4 or less.

A secondary efficacy analysis will evaluate the proportion of patients who have a reduction in Disease Activity Index score of 3 points or more from baseline to week 4 (responder). Assuming that the placebo response rate is no more than 60% and the rate of response in the active group is at least 40% more than in the placebo group (e.g., 30% placebo group responders vs. ≥70% active group responders), the sample size of 35 subjects per group (29 per group with evaluable data at week 4) has at least 80% power at the 5% level of significance to detect a difference between the placebo group and the active treatment group.

The secondary efficacy endpoints (change in stool frequency, rectal bleeding, fecal continence, endoscopic appearance, Investigator's Global Assessment, and Patient's Global Assessment) are also compared as a function of treatment group from baseline to week 4. In addition, intestinal tissue biopsies are harvested for quantitation of leukocytic infiltration (T cells, activated macrophages) and confirmed by cellular phenotyping using immunohistochemical surface marker analysis.

The present invention is not to be limited in scope by the specific embodiments describe herein. Indeed, various modifications of the invention in addition to those described herein will become apparent to those skilled in the art from the foregoing description and the accompanying figures. Such modifications are intended to fall within the scope of the appended claims.

and SLE Flare Index. Safety and tolerability is assessed by physical examination, clinical laboratory testing, and adverse event reporting.

What is claimed is:

1. An isolated antibody, or antigen-binding fragment thereof, that specifically binds human CD48 (SEQ ID NO:384) and blocks the interaction between human CD48 and a CD48 receptor with an $IC_{50}$ of less than about 400 pM in a CD48/CD48 receptor binding assay and comprises the complementarity determining regions (CDRs) of a heavy chain variable region (HCVR) having the amino acid sequence of SEQ ID NO:368 and the CDRs of a light chain variable region (LCVR) having the amino acid sequence of SEQ ID NO:370, wherein the CD48 receptor is human CD2 (SEQ ID NO:392) or human 2B4 (SEQ ID NO:390), and wherein the antibody or antigen-binding fragment binds an epitope within Ig domain 1 of human CD48 (amino acids 29 to 127 of SEQ ID NO:384).

2. The antibody or antigen-binding fragment of claim 1, wherein the antibody or antigen-binding fragment interacts with one or more amino acids located within amino acids 60 to 125 of SEQ ID NO:384.

3. The antibody or antigen-binding fragment of claim 2, wherein the antibody or antigen-binding fragment interacts with one or more amino acids located within amino acids 60 to 68 of SEQ ID NO:384 and/or amino acids 107 to 125 of SEQ ID NO:384.

4. The antibody or antigen-binding fragment of claim 3, wherein the antibody or antigen-binding fragment interacts with one or more amino acids located within amino acids 60 to 68 of SEQ ID NO:384 and with one or more amino acids located within amino acids 107 to 125 of SEQ ID NO:384.

5. The antibody or antigen-binding fragment of claim 4, wherein the antibody or antigen-binding fragment comprises heavy and light chain CDRs having the amino acid sequences of SEQ ID NOs: 354, 356, 358, 362, 364 and 366.

6. The antibody or antigen-binding fragment of claim 5, wherein the antibody or antigen-binding fragment comprises an HCVR having the amino acid sequence of SEQ ID NO:368, and an LCVR having the amino acid sequence of SEQ ID NO:370.

7. The isolated antibody, or antigen-binding fragment thereof of claim 1, wherein the antibody or antigen-binding fragment thereof inhibits activation of primary human peripheral blood mononuclear cells (PBMCs) in vitro.

8. The antibody or antigen-binding fragment of claim 7, wherein the antibody or antigen-binding fragment interacts with one or more amino acids located within amino acids 60 to 125 of SEQ ID NO:384.

9. The antibody or antigen-binding fragment of claim 8, wherein the antibody or antigen-binding fragment interacts with one or more amino acids located within amino acids 60 to 68 of SEQ ID NO:384 and/or amino acids 107 to 125 of SEQ ID NO:384.

10. The antibody or antigen-binding fragment of claim 9, wherein the antibody or antigen-binding fragment interacts with one or more amino acids located within amino acids 60 to 68 of SEQ ID NO:384 and with one or more amino acids located within amino acids 107 to 125 of SEQ ID NO:384.

11. The antibody or antigen-binding fragment of claim 10, wherein the antibody or antigen-binding fragment comprises the complementarity determining regions (CDRs) of a heavy chain variable region (HCVR) having the amino acid sequence of SEQ ID NO:368 and the CDRs of a light chain variable region (LCVR) having the amino acid sequence of SEQ ID NO:370.

12. The antibody or antigen-binding fragment of claim 11, wherein the antibody or antigen-binding fragment comprises heavy and light chain CDRs having the amino acid sequences of SEQ ID NOs: 354, 356, 358, 362, 364 and 366.

13. The antibody or antigen-binding fragment of claim 12, wherein the antibody or antigen-binding fragment comprises an HCVR having the amino acid sequence of SEQ ID NO:368, and an LCVR having the amino acid sequence of SEQ ID NO:370.

14. The antibody or antigen-binding fragment of claim 1, wherein the antibody or antigen-binding fragment thereof blocks the interaction between human CD48 and human 2B4 with an $IC_{50}$ of less than about 300 pM in a CD48/2B4 binding assay.

15. The antibody or antigen-binding fragment of claim 14, wherein the antibody or antigen-binding fragment thereof blocks the interaction between human CD48 and human 2B4 with an $IC_{50}$ of less than about 200 pM in a CD48/2B4 binding assay.

16. The antibody or antigen-binding fragment of claim 15, wherein the antibody or antigen-binding fragment thereof blocks the interaction between human CD48 and human 2B4 with an $IC_{50}$ of less than about 100 pM in a CD48/2B4 binding assay.

17. The antibody or antigen-binding fragment of claim 16, wherein the antibody or antigen-binding fragment thereof blocks the interaction between human CD48 and human 2B4 with an $IC_{50}$ of less than about 60 pM in a CD48/2B4 binding assay.

18. The antibody or antigen-binding fragment of claim 7, wherein the antibody or antigen-binding fragment thereof blocks the interaction between human CD48 and human 2B4 with an $IC_{50}$ of less than about 300 pM in a CD48/2B4 binding assay.

19. The antibody or antigen-binding fragment of claim 18, wherein the antibody or antigen-binding fragment thereof blocks the interaction between human CD48 and human 2B4 with an $IC_{50}$ of less than about 200 pM in a CD48/2B4 binding assay.

20. The antibody or antigen-binding fragment of claim 19, wherein the antibody or antigen-binding fragment thereof blocks the interaction between human CD48 and human 2B4 with an $IC_{50}$ of less than about 100 pM in a CD48/2B4 binding assay.

21. The antibody or antigen-binding fragment of claim 20, wherein the antibody or antigen-binding fragment thereof blocks the interaction between human CD48 and human 2B4 with an $IC_{50}$ of less than about 60 pM in a CD48/2B4 binding assay.

* * * * *